US008604179B2

(12) United States Patent
Akazawa et al.

(10) Patent No.: US 8,604,179 B2
(45) Date of Patent: Dec. 10, 2013

(54) NUCLEIC ACID COMPRISING CHIMERIC GENE DERIVED FROM HEPATITIS C VIRUS

(75) Inventors: Daisuke Akazawa, Kanagawa (JP); Takaji Wakita, Tokyo (JP)

(73) Assignees: Toray Industries, Inc., Tokyo (JP); Japan As Represented by Director-General of National Institute of Infectious Diseases, Tokyo (JP); Tokyo Metropolitan Organization for Medical Research, Tokyo (JP)

( * ) Notice: Subject to any disclaimer, the term of this patent is extended or adjusted under 35 U.S.C. 154(b) by 429 days.

(21) Appl. No.: 12/989,592

(22) PCT Filed: Apr. 24, 2009

(86) PCT No.: PCT/JP2009/058130
§ 371 (c)(1), (2), (4) Date: Oct. 25, 2010

(87) PCT Pub. No.: WO2009/131203
PCT Pub. Date: Oct. 29, 2009

(65) Prior Publication Data

US 2011/0045020 A1 Feb. 24, 2011

(30) Foreign Application Priority Data

Apr. 25, 2008 (JP) ................................ 2008-116193

(51) Int. Cl.
*A61K 39/29* (2006.01)
*C07K 14/005* (2006.01)
*C12N 7/00* (2006.01)

(52) U.S. Cl.
USPC .................. 536/23.72; 424/205.1; 435/235.1; 435/320.1; 435/5; 530/389.4

(58) Field of Classification Search
None
See application file for complete search history.

(56) References Cited

U.S. PATENT DOCUMENTS

| | | | | |
|---|---|---|---|---|
| 5,753,430 | A * | 5/1998 | Mehta et al. | 435/5 |
| 8,143,022 | B2 * | 3/2012 | Tanabe et al. | 435/69.1 |
| 2008/0220019 | A1 | 9/2008 | Wakita et al. | |
| 2010/0035345 | A1 | 2/2010 | Tanabe et al. | |

FOREIGN PATENT DOCUMENTS

| | | | |
|---|---|---|---|
| EP | 1801209 | A1 | 6/2007 |
| WO | 2005/080575 | A1 | 9/2005 |
| WO | 2006/022422 | A1 | 3/2006 |
| WO | 2006/096459 | A2 | 9/2006 |
| WO | WO 2007/037428 | A1 | 5/2007 |

OTHER PUBLICATIONS

Halliday et al. (Expert Review in Vaccines, 2011, vol. 10, p. 1-25).*
International Search Report, dated May 26, 2009, issued in corresponding International Application PCT/JP2009/058130.
Choo et al., "Isolation of a cDNA Clone Derived from a Blood-Borne Non-A, Non-B Viral Hepatitis Genome", Science, vol. 244, Apr. 21, 1989, pp. 359-362.
Gottwein et al., "Robust Hepatitis C Genotype 3a Cell Culture Releasing Adapted Intergenotypic 3a/2a (S52/JFH1) Viruses", Gastroenterology, Nov. 2007, vol. 133, No. 5, pp. 1614-1626.
Kato et al., "Hepatitis C Virus JFH-1 Strain Infection in Chimpanzees Is Associated With Low Pathogenicity and Emergence of an Adaptive Mutation", Hepatology, vol. 48, No. 3, 2008, pp. 732-740.
Kato et al., "Infection experiment of HCV JFH-1 strain in chimpanzee: functional analysis of in vivo adaptive mutation", Abstracts of the 44th Annual Meeting of the Japan Society of Hepatology, vol. 49, Suppl. 1, Apr. 30, 2008, p. A70 (WS7-10).
Lindenbach et al., "Cell culture-grown hepatitis C virus is infectious in vivo and can be recultured in vitro", PNAS Early Edition, pp. 1-5, publication date Feb. 16, 2006.
Lindenbach et al., "Complete Replication of Hepatitis C Virus in Cell Culture", Science, vol. 309, Jul. 22, 2005, pp. 623-626.
Lohmann et al., "Replication of Subgenomic Hepatitis C Virus RNAs in a Hepatoma Cell Line", Science, vol. 285, Jul. 2, 1999, pp. 110-113.
Pietschmann et al., "Construction and characterization of infectious intragenotypic and intergenotypic hepatitis C virus chimeras", PNAS, vol. 103, No. 19, May 9, 2006, pp. 7408-7413.
Pietschmann et al., "Persistent and Transient Replication of Full-Length Hepatitis C Virus Genomes in Cell Culture", Journal of Virology, vol. 76, No. 8, Apr. 2002, pp. 4008-4021.
Wakita et al., "Production of infectious hepatitis C virus in tissue culture from a cloned viral genome", Nature Medicine, 2005, pp. 1-6.
Yi et al., "Compensatory Mutations in E1, p7, NS2, and NS3 Enhance Yields of Cell Culture-Infectious Intergenotypic Chimeric Hepatitis C Virus", Journal of Virology, vol. 81, No. 2, Jan. 2007, pp. 629-638.

* cited by examiner

*Primary Examiner* — Agnieszka Boesen
(74) *Attorney, Agent, or Firm* — Birch, Stewart, Kolasch & Birch, LLP

(57) ABSTRACT

This invention provides infectious chimeric HCV particles that can be used for vaccines. This invention further provides a nucleic acid comprising a chimeric gene derived from the hepatitis C virus comprising regions each encoding Core protein, E1 protein, E2 protein and p7 protein derived from a hepatitis C virus strain other than JFH-1 strain; NS2 protein derived from JFH-1 strain or a hepatitis C virus strain other than JFH-1 strain, or a chimeric NS2 protein of NS2 protein derived from JFH-1 strain and NS2 protein derived from a hepatitis C virus strain other than JFH-1 strain; and NS3 protein, NS4A protein, NS4B protein, NS5A protein, and NS5B protein derived from JFH-1 strain in that order in 5' to 3' direction, wherein the 328th proline residue from the amino acid residue at N-terminus of the Core protein is substituted with an amino acid residue other than proline. This invention further provides chimeric HCV particles comprising such nucleic acid, and use of such HCV particles for vaccines.

15 Claims, 8 Drawing Sheets

* Primer/primer (PCR template)

1. ▬▬▬▬▬▬▬▬▬▬  MS151 / MS163 (pTH/JFH1)

2. ▬▬▬▬▬▬▬▬▬▬  MS162 / MS156 (pTH/JFH1)

3. ▬▬▬▬▬▬▬▬▬▬▬▬▬▬▬
   ↑ Acc65I       ↑ Acc65I
   MS151/ MS156 (PCR products 1 and 2)
   ↓
   Ligation with pTH/JFH1 cleaved with Acc65I

Fig. 6

| RNA | Culture supernatant | | In cell | | | Core secretion (%) | Infection titer of 96-hr culture supernatant (FFU/ml) | FFU/core |
|---|---|---|---|---|---|---|---|---|
| | 4 hr | 96 hr | 4 hr | 96 hr | Core ratio (96 hr/4 hr) | | | |
| TH/JFH-1 | - | 53.55 | 1.33 | 1187.40 | 892.78 | 4.32 | $1.0 \times 10^3$ | $1.5 \times 10^2$ |
| TH/JFH-1 (PA) | - | 190.15 | 0.93 | 679.80 | 730.97 | 21.86 | $2.8 \times 10^3$ | $1.2 \times 10^2$ |

(fmol/dish) (fmol/dish) (fmol/dish)

SEQUENCE LISTING

<160> NUMBER OF SEQ ID NOS: 19

<210> SEQ ID NO 1
<211> LENGTH: 9669
<212> TYPE: DNA
<213> ORGANISM: Artificial
<220> FEATURE:
<223> OTHER INFORMATION: pTH/JFH1(PA)

<400> SEQUENCE: 1

```
acctgcccct aatagggggcg acactccgcc atgaatcact cccctgtgag gaactactgt     60
cttcacgcag aaagcgccta gccatggcgt tagtatgagt gtcgtacagc ctccaggccc    120
ccccctcccg ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttgggttg cgaaaggcct tgtggtactg cctgataggg    300
cgcttgcgag tgccccggga ggtctcgtag accgtgcacc atgagcacga atcctaaacc    360
tcaaagaaaa accaaacgta acaccaaccg ccgcccacag gacgtcaagt tcccgggcgg    420
tggccagatc gttggtggag tttacctgtt gccgcgcagg ggccccaggt tgggtgtgcg    480
cgcgactagg aagacttccg agcggtcgca acctcgtgga aggcgacaac ctatccccaa    540
ggatcgccga cccgagggca gggcctgggc tcagcctggg taccccttggc ccctctatgg    600
caacgagggc atggggtggg caggatggct cctgtcaccc cgtggctccc ggcctagttg    660
gggccccaat gacccccggc gcaggtcgcg taatttgggt aaagtcatcg ataccccttac    720
atgcggcttc gccgacctca tggggtacat tccgctcgtc ggcgctccct tgggggggcgc    780
tgccagggcc ttggcgcatg gcgtccgggt tctggaggac ggcgtgaact atgcaacagg    840
gaatctgccc ggttgctctt tctctatctt cctcttggct ctgctgtcct gtctaaccat    900
cccagcttcc gcttatgaag tgcgcaacgt gtccggggtg taccatgtca cgaacgactg    960
ctccaactcg agcattgtgt acgagacagg ggacatgatt atgcacaccc ctgggtgcgt   1020
gccctgtgtt cgggagaaca actcctcccg ctgctgggca gcgctcactc ccacgctcgc   1080
ggccaggaac gccagcgtcc ccaccacgac aatacggcgc cacgtcgatt tgctcgttgg   1140
ggcggctgct ttctgctccg ctatgtacgt gggggatctc tgcggatctg ttttcctcgt   1200
ctcccagttg ttcaccttct cgcctcgccg gcatgagaca gtgcaggact gcaattgttc   1260
aatctatccc ggccacgtat caggtcaccg catggcttgg gatatgatga tgaactggtc   1320
agctacaaca gccctactgg tatcgcagtt actccggatc ccacaagccg tcgtggacat   1380
ggtggcgggg gcccactggg gagtcctggc gggccttgcc tactattcca tggcggggaa   1440
ctgggctaag gttttgattg tgctgctact ctttgccggc gttgatgggg cgacctacgt   1500
gacgggggggg tcggaagcca gaggggcctc tggcttagca aacctctttt catttggggc   1560
gtctcagaag atccagctca taaataccaa cggcagttgg cacatcaata gaactgccct   1620
gaactgcaat gactccctcc acactgggtt tcttgccgcg ctattctaca cacacaaatt   1680
caacgcgtcc ggatgtccag agcgcatggc cagctgccgc cccattgaag agttcgctca   1740
ggggtatggt cccatcactt atgctgagcc ctccccctcg gaccagaggc cctattgctg   1800
gcactacgcg cctcgaccgt gtggtatcat acccgcgtcg caggtgtgtg gtccagtgta   1860
ctgcttcacc ccaagccctg ttgtggtggg gacgaccgat cgctccggtg cccccacgta   1920
taattggggg gcgaatgaga cggacgtgct gtatctcaac aacacgcggc cgccgcaagg   1980
```

-continued

```
caactggttc ggctgcacat ggatgaatgg caccgggttc accaagacgt gcgggggccc   2040
cccgtgcaac atcggggggg gcggcaacaa caacaccttg acctgcccca cggactgttt   2100
ccggaaacac cccgaggcca cctacaccaa atgtggttcg ggaccttggt tgacacctag   2160
gtgcatggtc gactacccat acaggctctg gcactacccc tgcaccgtta actttaccat   2220
ctttaaggtt aggatgtacg tgggaggtgt ggagcacagg ctcaacgccg catgcaattg   2280
gacccgagga gagcgttgta acttagagga cagggataga tcagagctta gcccgctgct   2340
gctgtcaaca acagagtggc aggtgctacc ttgttccttc accaccctac cggctctgtc   2400
cactggtttg atccatctcc accagaacat cgtggacgtg caatacctgt acggtatagg   2460
gtcggcggtt gtctcctatg caatcaaatg ggaatatgtc ttgttgctct tcctcctcct   2520
ggcagacgcg cgcgtctgcg cctgcttgtg gatgatgctg ctgatagctc aagctgaggc   2580
cgccttagag aacctggtgg tcctcaatgc ggcgtccctg gctggagcgc atggccttct   2640
ctctttcctt gtgttcttct gtgccgcttg gtacatcaag ggcaggttga tccccggggc   2700
ggcgtatgct tttacggcg tatggccgct gctcctactc ctgctggcgt taccaccacg   2760
agcatacgcc atggaccggg agatggctgc atcgtgcgga ggcgcggttt ttgtaggtct   2820
ggcattcctg accttgtcac cacactataa ggcattcctc gccaagctcc tgtggtggtt   2880
gtgctatctc ctgaccctgg gggaagccat gattcaggag tgggtaccac ccatgcaggt   2940
gcgcggcggc cgcgatggca tcgcgtgggc cgtcactata ttctgcccgg gtgtggtgtt   3000
tgacattacc aaatggcttt tggcgttgct tgggcctgct tacctcttaa gggccgcttt   3060
gacacatgtg ccgtacttcg tcagagctca cgctctgata agggtatgcg ctttggtgaa   3120
gcagctcgcg gggggtaggt atgttcaggt ggcgctattg gcccttggca ggtggactgg   3180
cacctacatc tatgaccacc tcacacctat gtcggactgg gccgctagcg gcctgcgcga   3240
cttagcggtc gccgtggaac ccatcatctt cagtccgatg gagaagaagg tcatcgtctg   3300
gggagcggag acggctgcat gtggggacat tctacatgga cttcccgtgt ccgcccgact   3360
cggccaggag atcctcctcg gcccagctga tggctacacc tccaaggggt ggaagctcct   3420
tgctcccatc actgcttatg cccagcaaac acgaggcctc ctgggcgcca tagtggtgag   3480
tatgacgggg cgtgacagga cagaacaggc cggggaagtc caaatcctgt ccacagtctc   3540
tcagtccttc ctcggaacaa ccatctcggg ggttttgtgg actgtttacc acggagctgg   3600
caacaagact ctagccggct tacggggtcc ggtcacgcag atgtactcga gtgctgaggg   3660
ggacttggta ggctggccca gcccccctgg gaccaagtct ttggagccgt gcaagtgtgg   3720
agccgtcgac ctatatctgg tcacgcggaa cgctgatgtc atcccggctc ggagacgcgg   3780
ggacaagcgg ggagcattgc tctccccgag acccatttcg accttgaagg ggtcctcggg   3840
ggggccggtg ctctgcccta ggggccacgt cgttgggctc ttccgagcag ctgtgtgctc   3900
tcggggcgtg gccaaatcca tcgatttcat ccccgttgag acactcgacg ttgttacaag   3960
gtctcccact ttcagtgaca acagcacgcc accggctgtg ccccagacct atcaggtcgg   4020
gtacttgcat gctccaactg gcagtggaaa gagcaccaag gtccctgtcg cgtatgccgc   4080
ccaggggtac aaagtactag tgcttaaccc ctcggtagct gccaccctgg ggtttggggc   4140
gtacctatcc aaggcacatg gcatcaatcc caacattagg actggagtca ggaccgtgat   4200
gaccggggag gccatcacgt actccacata tggcaaattt ctcgccgatg gggggctgcgc   4260
tagcggcgcc tatgacatca tcatatgcga tgaatgccac gctgtggatg ctacctccat   4320
tctcggcatc ggaacggtcc ttgatcaagc agagacagcc ggggtcagac taactgtgct   4380
```

-continued

```
ggctacggcc acaccccccg ggtcagtgac aaccccccat cccgatatag aagaggtagg   4440
cctcgggcgg gagggtgaga tccccttcta tgggagggcg attcccctat cctgcatcaa   4500
gggagggaga cacctgattt tctgccactc aaagaaaaag tgtgacgagc tcgcggcggc   4560
ccttcggggc atgggcttga atgccgtggc atactataga gggttggacg tctccataat   4620
accagctcag ggagatgtgg tggtcgtcgc caccgacgcc ctcatgacgg ggtacactgg   4680
agactttgac tccgtgatcg actgcaatgt agcggtcacc caagctgtcg acttcagcct   4740
ggaccccacc ttcactataa ccacacagac tgtcccacaa gacgctgtct cacgcagtca   4800
gcgccgcggg cgcacaggta gaggaagaca gggcacttat aggtatgttt ccactggtga   4860
acgagcctca ggaatgtttg acagtgtagt gctttgtgag tgctacgacg caggggctgc   4920
gtggtacgat ctcacaccag cggagaccac cgtcaggctt agagcgtatt tcaacacgcc   4980
cggcctaccc gtgtgtcaag accatcttga attttgggag gcagttttca ccggcctcac   5040
acacatagac gcccacttcc tctcccaaac aaagcaagcg gggggagaact tcgcgtacct   5100
agtagcctac caagctacgg tgtgcgccag agccaaggcc cctcccccgt cctgggacgc   5160
catgtggaag tgcctggccc gactcaagcc tacgcttgcg ggccccacac ctctcctgta   5220
ccgtttgggc cctattacca atgaggtcac cctcacacac cctgggacga agtacatcgc   5280
cacatgcatg caagctgacc ttgaggtcat gaccagcacg tgggtcctag ctggaggagt   5340
cctggcagcc gtcgccgcat attgcctggc gactggatgc gtttccatca tcggccgctt   5400
gcacgtcaac cagcgagtcg tcgttgcgcc ggataaggag gtcctgtatg aggcttttga   5460
tgagatggag gaatgcgcct ctagggcggc tctcatcgaa gaggggcagc ggatagccga   5520
gatgttgaag tccaagatcc aaggcttgct gcagcaggcc tctaagcagg cccaggacat   5580
acaacccgct atgcaggctt catggcccaa agtggaacaa ttttgggcca gacacatgtg   5640
gaacttcatt agcggcatcc aatacctcgc aggattgtca acactgccag ggaacccccgc   5700
ggtggcttcc atgatggcat tcagtgccgc cctcaccagt ccgttgtcga ccagtaccac   5760
catccttctc aacatcatgg gaggctggtt agcgtcccag atcgcaccac ccgcgggggc   5820
caccggcttt gtcgtcagtg gcctggtggg ggctgccgtg ggcagcatag gcctgggtaa   5880
ggtgctggtg gacatcctgg caggatatgg tgcgggcatt tcgggggccc tcgtcgcatt   5940
caagatcatg tctggcgaga agccctctat ggaagatgtc atcaatctac tgcctgggat   6000
cctgtctccg ggagccctgg tggtgggggt catctgcgcg gccattctgc gccgccacgt   6060
gggaccgggg gagggcgcgg tccaatggat gaacaggctt attgcctttg cttccagagg   6120
aaaccacgtc gcccctactc actacgtgac ggagtcggat gcgtcgcagc gtgtgaccca   6180
actacttggc tctcttacta taaccagcct actcagaaga ctccacaatt ggataactga   6240
ggactgcccc atcccatgct ccggatcctg gctccgcgac gtgtgggact gggtttgcac   6300
catcttgaca gacttcaaaa attggctgac ctctaaattg ttccccaagc tgcccggcct   6360
ccccttcatc tcttgtcaaa aggggtacaa gggtgtgtgg gccggcactg gcatcatgac   6420
cacgcgctgc ccttgcggcg ccaacatctc tggcaatgtc cgcctgggct ctatgaggat   6480
cacagggcct aaaacctgca tgaacacctg gcaggggacc tttcctatca attgctacac   6540
ggagggccag tgcgcgccga aaccccccac gaactacaag accgccatct ggagggtggc   6600
ggcctcggag tacgcggagg tgacgcagca tgggtcgtac tcctatgtaa caggactgac   6660
cactgacaat ctgaaaattc cttgccaact accttctcca gagtttttct cctgggtgga   6720
cggtgtgcag atccataggt ttgcacccac accaaagccg tttttccggg atgaggtctc   6780
```

-continued gttctgcgtt gggcttaatt cctatgctgt cgggtcccag cttccctgtg aacctgagcc 6840
cgacgcagac gtattgaggt ccatgctaac agatccgccc cacatcacgg cggagactgc 6900
ggcgcggcgc ttggcacggg gatcacctcc atctgaggcg agctcctcag tgagccagct 6960
atcagcaccg tcgctgcggg ccacctgcac cacccacagc aacacctatg acgtggacat 7020
ggtcgatgcc aacctgctca tggagggcgg tgtggctcag acagagcctg agtccagggt 7080
gcccgttctg gactttctcg agccaatggc cgaggaagag agcgaccttg agccctcaat 7140
accatcggag tgcatgctcc ccaggagcgg gtttccacgg gccttaccgg cttgggcacg 7200
gcctgactac aacccgccgc tcgtggaatc gtggaggagg ccagattacc aaccgcccac 7260
cgttgctggt tgtgctctcc cccccccaa gaaggccccg acgcctcccc caaggagacg 7320
ccggacagtg ggtctgagcg agagcaccat atcagaagcc ctccagcaac tggccatcaa 7380
gacctttggc cagccccct cgagcggtga tgcaggctcg tccacggggg cgggcgccgc 7440
cgaatccggc ggtccgacgt cccctggtga gccggccccc tcagagacag gttccgcctc 7500
ctctatgccc cccctcgagg gggagcctgg agatccggac ctggagtctg atcaggtaga 7560
gcttcaacct ccccccagg ggggggggt agctcccggt tcgggctcgg ggtcttggtc 7620
tacttgctcc gaggaggacg ataccaccgt gtgctgctcc atgtcatact cctggaccgg 7680
ggctctaata actccctgta gccccgaaga ggaaaagttg ccaatcaacc ctttgagtaa 7740
ctcgctgttg cgataccata acaaggtgta ctgtacaaca tcaaagagcg cctcacagag 7800
ggctaaaaag gtaacttttg acaggacgca agtgctcgac gcccattatg actcagtctt 7860
aaaggacatc aagctagcgg cttccaaggt cagcgcaagg ctcctcacct tggaggaggc 7920
gtgccagttg actccacccc attctgcaag atccaagtat ggattcgggg ccaaggaggt 7980
ccgcagcttg tccgggaggg ccgttaacca catcaagtcc gtgtggaagg acctcctgga 8040
agacccacaa acaccaattc ccacaaccat catggccaaa aatgaggtgt tctgcgtgga 8100
ccccgccaag gggggtaaga aaccagctcg cctcatcgtt taccctgacc tcggcgtccg 8160
ggtctgcgag aaaatggccc tctatgacat tacacaaaag cttcctcagg cggtaatggg 8220
agcttcctat ggcttccagt actcccctgc ccaacgggtg gagtatctct tgaaagcatg 8280
ggcggaaaag aaggacccca tgggtttttc gtatgatacc cgatgcttcg actcaaccgt 8340
cactgagaga gacatcagga ccgaggagtc catataccag gcctgctccc tgcccgagga 8400
ggcccgcact gccatacact cgctgactga gagactttac gtaggagggc ccatgttcaa 8460
cagcaagggt caaacctgcg gttacagacg ttgccgcgcc agcggggtgc taaccactag 8520
catgggtaac accatcacat gctatgtgaa agccctagcg gcctgcaagg ctgcggggat 8580
agttgcgccc acaatgctgg tatgcggcga tgacctagta gtcatctcag aaagccaggg 8640
gactgaggag gacgagcgga acctgagagc cttcacggag gccatgacca ggtactctgc 8700
ccctcctggt gatcccccca gaccggaata tgacctggag ctaataacat cctgttcctc 8760
aaatgtgtct gtggcgttgg gcccgcgggg ccgccgcaga tactacctga ccagagaccc 8820
aaccactcca ctcgcccggg ctgcctggga aacagttaga cactccccta tcaattcatg 8880
gctgggaaac atcatccagt atgctccaac catatgggtt cgcatggtcc taatgacaca 8940
cttcttctcc attctcatgg tccaagacac cctggaccag aacctcaact ttgagatgta 9000
tggatcagta tactccgtga atcctttgga ccttccagcc ataattgaga ggttacacgg 9060
gcttgacgcc ttttctatgc acacatactc tcaccacgaa ctgacgcggg tggcttcagc 9120
cctcagaaaa cttggggcgc caccctcag ggtgtggaag agtcgggctc gcgcagtcag 9180
ggcgtccctc atctcccgtg gagggaaagc ggccgtttgc ggccgatatc tcttcaattg 9240
ggcggtgaag accaagctca aactcactcc attgccggag gcgcgcctac tggacttatc 9300
cagttggttc accgtcggcg ccggcggggg cgacattttt cacagcgtgt cgcgcgcccg 9360
accccgctca ttactcttcg gcctactcct acttttcgta ggggtaggcc tcttcctact 9420
ccccgctcgg tagagcggca cacactaggt acactccata gctaactgtt cctttttttt 9480
tttttttttt tttttttttt tttttttttt tttttctttt tttttttttt ccctctttct 9540
tcccttctca tcttattcta ctttctttct tggtggctcc atcttagccc tagtcacggc 9600
tagctgtgaa aggtccgtga gccgcatgac tgcagagagt gccgtaactg gtctctctgc 9660
agatcatgt 9669

<210> SEQ ID NO 2
<211> LENGTH: 9669
<212> TYPE: DNA
<213> ORGANISM: Artificial
<220> FEATURE:
<223> OTHER INFORMATION: pTH/JFH1(PT)

<400> SEQUENCE: 2
acctgcccct aataggggcg acactccgcc atgaatcact cccctgtgag gaactactgt 60
cttcacgcag aaagcgccta gccatggcgt tagtatgagt gtcgtacagc ctccaggccc 120
ccccctcccg ggagagccat agtggtctgc ggaaccggtg agtacaccgg aattgccggg 180
aagactgggt cctttcttgg ataaacccac tctatgcccg gccatttggg cgtgcccccg 240
caagactgct agccgagtag cgttgggttg cgaaaggcct tgtggtactg cctgataggg 300
cgcttgcgag tgccccggga ggtctcgtag accgtgcacc atgagcacga atcctaaacc 360
tcaaagaaaa accaaacgta acaccaaccg ccgcccacag gacgtcaagt tcccgggcgg 420
tggccagatc gttggtggag tttacctgtt gccgcgcagg ggccccaggt tgggtgtgcg 480
cgcgactagg aagacttccg agcggtcgca acctcgtgga aggcgacaac ctatccccaa 540
ggatcgccga cccgagggca gggcctgggc tcagcctggg taccettggc ccctctatgg 600 caacgagggc atggggtggg caggatggct cctgtcaccc cgtggctccc ggcctagttg 660
gggccccaat gacccccggc gcaggtcgcg taatttgggt aaagtcatcg ataccettac 720 atgcggcttc gccgacctca tggggtacat tccgctcgtc ggcgctccct tgggggggcgc 780 tgccagggcc ttggcgcatg gcgtccgggt tctggaggac ggcgtgaact atgcaacagg 840
gaatctgccc ggttgctctt tctctatctt cctcttggct ctgctgtcct gtctaaccat 900
cccagcttcc gcttatgaag tgcgcaacgt gtccggggtg taccatgtca cgaacgactg 960
ctccaactcg agcattgtgt acgagacagg ggacatgatt atgcacaccc ctgggtgcgt 1020
gccctgtgtt cgggagaaca actcctcccg ctgctgggca gcgctcactc ccacgctcgc 1080
ggccaggaac gccagcgtcc ccaccacgac aatacggcgc cacgtcgatt tgctcgttgg 1140
ggcggctgct ttctgctccg ctatgtacgt gggggatctc tgcggatctg ttttcctcgt 1200
ctcccagttg ttcaccttct cgcctcgccg gcatgagaca gtgcaggact gcaattgttc 1260
aatctatccc ggccacgtat caggtcaccg catggcttgg gatatgatga tgaactggtc 1320
aactacaaca gccctactgg tatcgcagtt actccggatc ccacaagccg tcgtggacat 1380
ggtggcgggg gcccactggg gagtcctggc gggccttgcc tactattcca tggcggggaa 1440
ctgggctaag gttttgattg tgctgctact ctttgccggc gttgatgggg cgacctacgt 1500
gacggggggg tcggaagcca gaggggcctc tggcttagca aacctctttt catttggggc 1560

-continued

```
gtctcagaag atccagctca taaataccaa cggcagttgg cacatcaata gaactgccct   1620
gaactgcaat gactccctcc acactgggtt tcttgccgcg ctattctaca cacacaaatt   1680
caacgcgtcc ggatgtccag agcgcatggc cagctgccgc cccattgaag agttcgctca   1740
ggggtatggt cccatcactt atgctgagcc ctccccctcg gaccagaggc cctattgctg   1800
gcactacgcg cctcgaccgt gtggtatcat acccgcgtcg caggtgtgtg gtccagtgta   1860
ctgcttcacc ccaagccctg ttgtggtggg gacgaccgat cgctccggtg cccccacgta   1920
taattggggg gcgaatgaga cggacgtgct gtatctcaac aacacgcggc cgccgcaagg   1980
caactggttc ggctgcacat ggatgaatgg caccgggttc accaagacgt gcgggggccc   2040
cccgtgcaac atcggggggg gcggcaacaa caacaccttg acctgcccca cggactgttt   2100
ccggaaacac cccgaggcca cctacaccaa atgtggttcg ggaccttggt tgacacctag   2160
gtgcatggtc gactacccat acaggctctg gcactacccc tgcaccgtta actttaccat   2220
ctttaaggtt aggatgtacg tgggaggtgt ggagcacagg ctcaacgccg catgcaattg   2280
gacccgagga gagcgttgta acttagagga cagggataga tcagagctta gcccgctgct   2340
gctgtcaaca acagagtggc aggtgctacc ttgttccttc accaccctac cggctctgtc   2400
cactggtttg atccatctcc accagaacat cgtggacgtg caatacctgt acggtatagg   2460
gtcggcggtt gtctcctatg caatcaaatg ggaatatgtc ttgttgctct tcctcctcct   2520
ggcagacgcg cgcgtctgcg cctgcttgtg gatgatgctg ctgatagctc aagctgaggc   2580
cgccttagag aacctggtgg tcctcaatgc ggcgtccctg gctggagcgc atggccttct   2640
ctctttcctt gtgttcttct gtgccgcttg gtacatcaag ggcaggttga tccccggggc   2700
ggcgtatgct ttttacggcg tatggccgct gctcctactc ctgctggcgt taccaccacg   2760
agcatacgcc atggaccggg agatggctgc atcgtgcgga ggcgcggttt ttgtaggtct   2820
ggcattcctg accttgtcac cacactataa ggcattcctc gccaagctcc tgtggtggtt   2880
gtgctatctc ctgaccctgg gggaagccat gattcaggag tgggtaccac ccatgcaggt   2940
gcgcggcggc cgcgatggca tcgcgtgggc cgtcactata ttctgcccgg gtgtggtgtt   3000
tgacattacc aaatggcttt tggcgttgct tgggcctgct tacctcttaa gggccgcttt   3060
gacacatgtg ccgtacttcg tcagagctca cgctctgata agggtatgcg ctttggtgaa   3120
gcagctcgcg gggggtaggt atgttcaggt ggcgctattg gcccttggca ggtggactgg   3180
cacctacatc tatgaccacc tcacacctat gtcggactgg gccgctagcg gcctgcgcga   3240
cttagcggtc gccgtggaac ccatcatctt cagtccgatg gagaagaagg tcatcgtctg   3300
gggagcggag acggctgcat gtggggacat tctacatgga cttcccgtgt ccgcccgact   3360
cggccaggag atcctcctcg gcccagctga tggctacacc tccaaggggt ggaagctcct   3420
tgctcccatc actgcttatg cccagcaaac acgaggcctc ctgggcgcca tagtggtgag   3480
tatgacgggg cgtgacagga cagaacaggc cggggaagtc caaatcctgt ccacagtctc   3540
tcagtccttc ctcggaacaa ccatctcggg ggttttgtgg actgtttacc acggagctgg   3600
caacaagact ctagccggct tacggggtcc ggtcacgcag atgtactcga gtgctgaggg   3660
ggacttggta ggctggccca gcccccctgg gaccaagtct ttggagccgt gcaagtgtgg   3720
agccgtcgac ctatatctgg tcacgcggaa cgctgatgtc atcccggctc ggagacgcgg   3780
ggacaagcgg ggagcattgc tctccccgag acccatttcg accttgaagg ggtcctcggg   3840
ggggccggtg ctctgcccta ggggccacgt cgttgggctc ttccgagcag ctgtgtgctc   3900
tcggggcgtg gccaaatcca tcgatttcat ccccgttgag acactcgacg ttgttacaag   3960
```

-continued

```
gtctcccact ttcagtgaca acagcacgcc accggctgtg ccccagacct atcaggtcgg   4020
gtacttgcat gctccaactg gcagtggaaa gagcaccaag gtccctgtcg cgtatgccgc   4080
ccaggggtac aaagtactag tgcttaaccc ctcggtagct gccaccctgg ggtttggggc   4140
gtacctatcc aaggcacatg gcatcaatcc caacattagg actggagtca ggaccgtgat   4200
gaccggggag gccatcacgt actccacata tggcaaattt ctcgccgatg gggctgcgc    4260
tagcggcgcc tatgacatca tcatatgcga tgaatgccac gctgtggatg ctacctccat   4320
tctcggcatc ggaacggtcc ttgatcaagc agagacagcc ggggtcagac taactgtgct   4380
ggctacggcc acacccccg ggtcagtgac aacccccat cccgatatag aagaggtagg     4440
cctcgggcgg gagggtgaga tccccttcta tgggagggcg attcccctat cctgcatcaa   4500
gggagggaga cacctgattt tctgccactc aaagaaaaag tgtgacgagc tcgcggcggc   4560
ccttcggggc atgggcttga atgccgtggc atactataga gggttggacg tctccataat   4620
accagctcag ggagatgtgg tggtcgtcgc caccgacgcc ctcatgacgg ggtacactgg   4680
agactttgac tccgtgatcg actgcaatgt agcggtcacc caagctgtcg acttcagcct   4740
ggaccccacc ttcactataa ccacacagac tgtcccacaa gacgctgtct cacgcagtca   4800
gcgccgcggg cgcacaggta gaggaagaca gggcacttat aggtatgttt ccactggtga   4860
acgagcctca ggaatgtttg acagtgtagt gctttgtgag tgctacgacg caggggctgc   4920
gtggtacgat ctcacaccag cggagaccac cgtcaggctt agagcgtatt tcaacacgcc   4980
cggcctaccc gtgtgtcaag accatcttga attttgggag gcagttttca ccggcctcac   5040
acacatagac gcccacttcc tctcccaaac aaagcaagcg gggagaaact tcgcgtacct   5100
agtagcctac caagctacgg tgtgcgccag agccaaggcc cctcccccgt cctgggacgc   5160
catgtggaag tgcctggccc gactcaagcc tacgcttgcg ggccccacac ctctcctgta   5220
ccgtttgggc cctattacca atgaggtcac cctcacacac cctgggacga agtacatcgc   5280
cacatgcatg caagctgacc ttgaggtcat gaccagcacg tgggtcctag ctggaggagt   5340
cctggcagcc gtcgccgcat attgcctggc gactggatgc gtttccatca tcggccgctt   5400
gcacgtcaac cagcgagtcg tcgttgcgcc ggataaggag gtcctgtatg aggcttttga   5460
tgagatggag gaatgcgcct ctagggcggc tctcatcgaa gaggggcagc ggatagccga   5520
gatgttgaag tccaagatcc aaggcttgct gcagcaggcc tctaagcagg cccaggacat   5580
acaacccgct atgcaggctt catggcccaa agtggaacaa ttttgggcca gacacatgtg   5640
gaacttcatt agcggcatcc aatacctcgc aggattgtca acactgccag ggaacccgc    5700
ggtggcttcc atgatggcat tcagtgccgc cctcaccagt ccgttgtcga ccagtaccac   5760
catccttctc aacatcatgg gaggctggtt agcgtcccag atcgcaccac ccgcgggggc   5820
caccggcttt gtcgtcagtg gcctggtggg ggctgccgtg ggcagcatag gcctgggtaa   5880
ggtgctggtg gacatcctgg caggatatgg tgcgggcatt tcgggggccc tcgtcgcatt   5940
caagatcatg tctggcgaga agccctctat ggaagatgtc atcaatctac tgcctgggat   6000
cctgtctccg ggagccctgg tggtgggggt catctgcgcg gccattctgc gccgccacgt   6060
gggaccgggg gagggcgcgg tccaatggat gaacaggctt attgcctttg cttccagagg   6120
aaaccacgtc gcccctactc actacgtgac ggagtcggat gcgtcgcagc gtgtgaccca   6180
actacttggc tctcttacta taaccagcct actcagaaga ctccacaatt ggataactga   6240
ggactgcccc atcccatgct ccggatcctg gctccgcgac gtgtgggact gggtttgcac   6300
catcttgaca gacttcaaaa attggctgac ctctaaattg ttccccaagc tgcccggcct   6360
```

-continued

```
ccccttcatc tcttgtcaaa aggggtacaa gggtgtgtgg gccggcactg gcatcatgac   6420
cacgcgctgc ccttgcggcg ccaacatctc tggcaatgtc cgcctgggct ctatgaggat   6480
cacagggcct aaaacctgca tgaacacctg gcaggggacc tttcctatca attgctacac   6540
ggagggccag tgcgcgccga aaccccccac gaactacaag accgccatct ggagggtggc   6600
ggcctcggag tacgcggagg tgacgcagca tgggtcgtac tcctatgtaa caggactgac   6660
cactgacaat ctgaaaattc cttgccaact accttctcca gagtttttct cctgggtgga   6720
cggtgtgcag atccataggt ttgcacccac accaaagccg tttttccggg atgaggtctc   6780
gttctgcgtt gggcttaatt cctatgctgt cgggtcccag cttccctgtg aacctgagcc   6840
cgacgcagac gtattgaggt ccatgctaac agatccgccc cacatcacgg cggagactgc   6900
ggcgcggcgc ttggcacggg gatcacctcc atctgaggcg agctcctcag tgagccagct   6960
atcagcaccg tcgctgcggg ccacctgcac cacccacagc aacacctatg acgtggacat   7020
ggtcgatgcc aacctgctca tggagggcgg tgtggctcag acagagcctg agtccagggt   7080
gcccgttctg gactttctcg agccaatggc cgaggaagag agcgaccttg agccctcaat   7140
accatcggag tgcatgctcc ccaggagcgg gtttccacgg gccttaccgg cttgggcacg   7200
gcctgactac aacccgccgc tcgtggaatc gtggaggagg ccagattacc aaccgcccac   7260
cgttgctggt tgtgctctcc cccccccaa gaaggccccg acgcctcccc caaggagacg    7320
ccggacagtg ggtctgagcg agagcaccat atcagaagcc ctccagcaac tggccatcaa   7380
gacctttggc cagcccccct cgagcggtga tgcaggctcg tccacggggg cgggcgccgc   7440
cgaatccggc ggtccgacgt cccctggtga gccggccccc tcagagacag gttccgcctc   7500
ctctatgccc cccctcgagg gggagcctgg agatccggac ctggagtctg atcaggtaga   7560
gcttcaacct cccccccagg gggggggggt agctcccggt tcgggctcgg ggtcttggtc   7620
tacttgctcc gaggaggacg ataccaccgt gtgctgctcc atgtcatact cctggaccgg   7680
ggctctaata actccctgta gccccgaaga ggaaaagttg ccaatcaacc ctttgagtaa   7740
ctcgctgttg cgataccata acaaggtgta ctgtacaaca tcaaagagcg cctcacagag   7800
ggctaaaaag gtaacttttg acaggacgca agtgctcgac gcccattatg actcagtctt   7860
aaaggacatc aagctagcgg cttccaaggt cagcgcaagg ctcctcacct tggaggaggc   7920
gtgccagttg actccacccc attctgcaag atccaagtat ggattcgggg ccaaggaggt   7980
ccgcagcttg tccgggaggg ccgttaacca catcaagtcc gtgtggaagg acctcctgga   8040
agacccacaa acaccaattc ccacaaccat catggccaaa aatgaggtgt tctgcgtgga   8100
ccccgccaag gggggtaaga aaccagctcg cctcatcgtt taccctgacc tcggcgtccg   8160
ggtctgcgag aaaatggccc tctatgacat tacacaaaag cttcctcagg cggtaatggg   8220
agcttcctat ggcttccagt actcccctgc ccaacgggtg gagtatctct tgaaagcatg   8280
ggcggaaaag aaggacccca tgggtttttc gtatgatacc cgatgcttcg actcaaccgt   8340
cactgagaga gacatcagga ccgaggagtc catataccag gcctgctccc tgcccgagga   8400
ggcccgcact gccatacact cgctgactga gagactttac gtaggagggc ccatgttcaa   8460
cagcaagggt caaacctgcg gttacagacg ttgccgcgcc agcggggtgc taaccactag   8520
catgggtaac accatcacat gctatgtgaa agccctagcg gcctgcaagg ctgcggggat   8580
agttgcgccc acaatgctgg tatgcggcga tgacctagta gtcatctcag aaagccaggg   8640
gactgaggag gacgagcgga acctgagagc cttcacggag gccatgacca ggtactctgc   8700
ccctcctggt gatcccccca gaccggaata tgacctggag ctaataacat cctgttcctc   8760
```

-continued aaatgtgtct gtggcgttgg gcccgcgggg ccgccgcaga tactacctga ccagagaccc 8820
aaccactcca ctcgcccggg ctgcctggga aacagttaga cactccccta tcaattcatg 8880
gctgggaaac atcatccagt atgctccaac catatgggtt cgcatggtcc taatgacaca 8940
cttcttctcc attctcatgg tccaagacac cctggaccag aacctcaact ttgagatgta 9000
tggatcagta tactccgtga atcctttgga ccttccagcc ataattgaga ggttacacgg 9060
gcttgacgcc ttttctatgc acacatactc tcaccacgaa ctgacgcggg tggcttcagc 9120
cctcagaaaa cttggggcgc caccccctcag ggtgtggaag agtcgggctc gcgcagtcag 9180
ggcgtccctc atctcccgtg gagggaaagc ggccgtttgc ggccgatatc tcttcaattg 9240
ggcggtgaag accaagctca aactcactcc attgccggag gcgcgcctac tggacttatc 9300
cagttggttc accgtcggcg ccggcggggg cgacattttt cacagcgtgt cgcgcgcccg 9360
accccgctca ttactcttcg gcctactcct acttttcgta ggggtaggcc tcttcctact 9420
ccccgctcgg tagagcggca cacactaggt acactccata gctaactgtt cctttttttt 9480
tttttttttt tttttttttt tttttttttt tttttctttt tttttttttt ccctctttct 9540
tcccttctca tcttattcta ctttctttct tggtggctcc atcttagccc tagtcacggc 9600
tagctgtgaa aggtccgtga gccgcatgac tgcagagagt gccgtaactg gtctctctgc 9660
agatcatgt 9669

<210> SEQ ID NO 3
<211> LENGTH: 9669
<212> TYPE: RNA
<213> ORGANISM: Artificial
<220> FEATURE:
<223> OTHER INFORMATION: pTH/JFH1(PA)

<400> SEQUENCE: 3
accugccccu aauaggggcg acacuccgcc augaaucacu ccccugugag gaacuacugu 60
cuucacgcag aaagcgccua gccauggcgu uaguaugagu gucguacagc cuccaggccc 120
cccccucccg ggagagccau aguggucugc ggaaccggug aguacaccgg aauugccggg 180
aagacugggu ccuuucuugg auaaacccac ucuaugcccg gccauuuggg cgugcccccg 240
caagacugcu agccgaguag cguuggguug cgaaaggccu ugugguacug ccugauaggg 300
cgcuugcgag ugccccggga ggucucguag accgugcacc augagcacga auccuaaacc 360
ucaaagaaaa accaaacgua acaccaaccg ccgcccacag gacgucaagu ucccgggcgg 420
uggccagauc guugguggag uuuaccuguu gccgcgcagg ggccccaggu ugggugugcg 480
cgcgacuagg aagacuuccg agcggucgca accucgugga aggcgacaac cuauccccaa 540
ggaucgccga cccgagggca gggccugggc ucagccuggg uacccuuggc cccucuaugg 600
caacgagggc augggguggg caggauggcu ccugucaccc cguggcuccc ggccuaguug 660
gggccccaau gacccccggc gcaggucgcg uaauuugggu aaagucaucg auacccuuac 720
augcggcuuc gccgaccuca uggggguacau uccgcucguc ggcgcucccu ugggggggcgc 780 ugccagggcc uuggcgcaug gcguccgggu ucuggaggac ggcgugaacu augcaacagg 840
gaaucugccc gguugcucuu ucucuaucuu ccucuuggcu cugcuguccu gucuaaccau 900
cccagcuucc gcuuaugaag ugcgcaacgu guccggggug uaccauguca cgaacgacug 960
cuccaacucg agcauugugu acgagacagg ggacaugauu augcacaccc cugggugcgu 1020
gcccuguguu cgggagaaca acuccucccg cugcugggca gcgcucacuc ccacgcucgc 1080
ggccaggaac gccagcgucc ccaccacgac aauacggcgc cacgucgauu ugcucguugg 1140

-continued ggcggcugcu uucugcuccg cuauguacgu gggggaucuc ugcggaucug uuuuccucgu 1200
cucccaguug uucaccuucu cgccucgccg gcaugagaca gugcaggacu gcaauuguuc 1260
aaucuauccc ggccacguau caggucaccg cauggcuugg gauaugauga ugaacugguc 1320
agcuacaaca gcccuacugg uaucgcaguu acuccggauc ccacaagccg ucguggacau 1380
gguggcgggg gcccacuggg gaguccuggc gggccuugcc uacuauucca uggcggggaa 1440
cugggcuaag guuuugauug ugcugcuacu cuuugccggc guugaugggg cgaccuacgu 1500 gacgggggg ucggaagcca gaggggccuc uggcuuagca aaccucuuuu cauuuggggc 1560
gucucagaag auccagcuca uaaauaccaa cggcaguugg cacaucaaua gaacugcccu 1620
gaacugcaau gacucccucc acacugggu ucuugccgcg cuauucuaca cacacaaauu 1680
caacgcgucc ggauguccag agcgcauggc cagcugccgc cccauugaag aguucgcuca 1740
gggguauggu cccaucacuu augcugagcc cucccccucg gaccagaggc ccuauugcug 1800
gcacuacgcg ccucgaccgu gugguaucau acccgcgucg caggugugug guccagugua 1860
cugcuucacc ccaagcccug uuguggugg gacgaccgau cgcuccggug cccccacgua 1920
uaauuggggg gcgaaugaga cggacgugcu guaucucaac aacacgcggc cgccgcaagg 1980
caacugguuc ggcugcacau ggaugaaugg caccggguuc accaagacgu gcgggggccc 2040
cccgugcaac aucgggggg gcggcaacaa caacaccuug accugcccca cggacuguuu 2100
ccggaaacac cccgaggcca ccuacaccaa augugguucg ggaccuuggu ugacaccuag 2160 gugcauggu gacuacccau acaggcucug gcacuacccc ugcaccguua acuuuaccau 2220
cuuuaagguu aggauguacg ugggaggugu ggagcacagg cucaacgccg caugcaauug 2280
gacccgagga gagcguugua acuuagagga cagggauaga ucagagcuua gcccgcugcu 2340
gcugucaaca acagaguggc aggugcuacc uuguuccuuc accacccuac cggcucuguc 2400
cacugguuug auccaucucc accagaacau cguggacgug caauaccugu acgguauagg 2460
gucggcgguu gucuccuaug caaucaaaug ggaauauguc uuguugcucu uccuccuccu 2520
ggcagacgcg cgcgucugcg ccugcuugug gaugaugcug cugauagcuc aagcugaggc 2580
cgccuuagag aaccuggugg uccucaaugc ggcgucccug gcuggagcgc auggccuucu 2640
cucuuuccuu guguucuucu gugccgcuug guacaucaag ggcagguuga uccccggggc 2700
ggcguaugcu uuuuacggcg uauggccgcu gcuccuacuc cugcuggcgu uaccaccacg 2760
agcauacgcc auggaccggg agauggcugc aucgugcgga ggcgcgguuu uuguaggucu 2820
ggcauuccug accuugucac cacacuauaa ggcauuccuc gccaagcucc ugugguggu 2880 gugcuaucuc cugacccugg gggaagccau gauucaggag uggguaccac ccaugcaggu 2940
gcgcggcggc cgcgauggca ucgcgugggc cgucacuaua uucugcccgg guguggugu 3000 ugacauuacc aaauggcuuu uggcguugcu ugggccugcu uaccucuuaa gggccgcuuu 3060
gacacaugug ccguacuucg ucagagcuca cgcucugaua aggguaugcg cuuuggugaa 3120
gcagcucgcg ggggguaggu auguucaggu ggcgcuauug gcccuuggca gguggacugg 3180
caccuacauc uaugaccacc ucacaccuau gucggacugg gccgcuagcg gccugcgcga 3240
cuuagcgguc gccguggaac ccaucaucuu caguccgaug gagaagaagg ucaucgucug 3300
gggagcggag acggcugcau guggggacau ucuacaugga cuucccgugu ccgcccgacu 3360
cggccaggag auccuccucg gcccagcuga uggcuacacc uccaaggggu ggaagcuccu 3420
ugcucccauc acugcuuaug cccagcaaac acgaggccuc cugggcgcca uaguggugag 3480
uaugacgggg cgugacagga cagaacaggc cggggaaguc caaauccugu ccacagucuc 3540

-continued ucaguccuuc cucggaacaa ccaucucggg gguuuugugg acuguuuacc acggagcugg 3600
caacaagacu cuagccggcu uacggggucc ggucacgcag auguacucga gugcugaggg 3660
ggacuuggua ggcuggccca gcccccccugg gaccaagucu uuggagccgu gcaagugugg 3720
agccgucgac cuauaucugg ucacgcggaa cgcugauguc aucccggcuc ggagacgcgg 3780
ggacaagcgg ggagcauugc ucuccccgag acccauuucg accuugaagg gguccucggg 3840
ggggccggug cucugcccua ggggccacgu cguugggcuc uuccgagcag cugugugcuc 3900
ucggggcgug gccaaaucca ucgauuucau ccccguugag acacucgacg uuguuacaag 3960
gucucccacu uucagugaca acagcacgcc accggcugug ccccagaccu aucaggucgg 4020
guacuugcau gcuccaacug gcaguggaaa gagcaccaag gucccugucg cguaugccgc 4080 ccaggggguac aaaguacuag ugcuuaaccc cucgguagcu gccacccugg gguuuggggc 4140
guaccuaucc aaggcacaug gcaucaaucc caacauuagg acuggaguca ggaccgugau 4200
gaccggggag gccaucacgu acuccacaua uggcaaauuu cucgccgaug ggggcugcgc 4260
uagcggcgcc uaugacauca ucauaugcga ugaaugccac gcuguggaug cuaccuccau 4320
ucucggcauc ggaacggucc uugaucaagc agagacagcc ggggucagac uaacugugcu 4380
ggcuacggcc acacccccccg ggucagugac aacccccccau cccgauauag aagagguagg 4440
ccucgggcgg gagggugaga uccccuucua ugggagggcg auuccccuau ccugcaucaa 4500
gggagggaga caccugauuu ucugccacuc aaagaaaaag ugugacgagc ucgcggcggc 4560
ccuucggggc augggcuuga augccguggc auacuauaga ggguuggacg ucuccauaau 4620
accagcucag ggagaugugg uggucgucgc caccgacgcc cucaugacgg gguacacugg 4680
agacuuugac uccgugaucg acugcaaugu agcggucacc caagcugucg acuucagccu 4740
ggaccccacc uucacuauaa ccacacagac ugucccacaa gacgcugucu cacgcaguca 4800
gcgccgcggg cgcacaggua gaggaagaca gggcacuuau agguauguuu ccacugguga 4860
acgagccuca ggaauguuug acaguguagu gcuuugugag ugcuacgacg caggggcugc 4920
gugguacgau cucacaccag cggagaccac cgucaggcuu agagcguauu ucaacacgcc 4980
cggccuaccc gugugucaag accaucuuga auuuugggag gcaguuuuca ccggccucac 5040
acacauagac gcccacuucc ucucccaaac aaagcaagcg gggggagaacu ucgcguaccu 5100 aguagccuac caagcuacgg ugugcgccag agccaaggcc ccucccccgu ccugggacgc 5160
cauguggaag ugccuggccc gacucaagcc uacgcuugcg ggccccacac cucuccugua 5220
ccguuugggc ccuauuacca augaggucac ccucacacac ccugggacga aguacaucgc 5280
cacaugcaug caagcugacc uugaggucau gaccagcacg ugggguccuag cuggaggagu 5340 ccuggcagcc gucgccgcau auugccuggc gacuggaugc guuuccauca ucggccgcuu 5400
gcacgucaac cagcgagucg ucguugcgcc ggauaaggag guccuguaug aggcuuuuga 5460
ugagauggag gaaugcgccu cuagggcggc ucucaucgaa gaggggcagc ggauagccga 5520
gauguugaag uccaagaucc aaggcuugcu gcagcaggcc ucuaagcagg cccaggacau 5580
acaacccgcu augcaggcuu cauggcccaa aguggaacaa uuuugggcca gacacaugug 5640
gaacuucauu agcggcaucc aauaccucgc aggauuguca acacugccag ggaacccccgc 5700 gguggcuucc augauggcau ucagugccgc ccucaccagu ccguugucga ccaguaccac 5760
cauccuucuc aacaucaugg gaggcugguu agcgucccag aucgcaccac ccgcgggggc 5820
caccggcuuu gucgucagug gccugguggg ggcugccgug ggcagcauag gccuggguaa 5880
ggugcuggug gacauccugg caggauaugg ugcgggcauu ucgggggccc ucgucgcauu 5940

-continued caagaucaug ucuggcgaga agcccucuau ggaagauguc aucaaucuac ugccugggau 6000
ccugucuccg ggagcccugg uggugggggu caucugcgcg gccauucugc gccgccacgu 6060
gggaccgggg gagggcgcgg uccaauggau gaacaggcuu auugccuuug cuuccagagg 6120
aaaccacguc gccccuacuc acuacgugac ggagucggau gcgucgcagc gugugaccca 6180
acuacuuggc ucucuuacua uaaccagccu acucagaaga cuccacaauu ggauaacuga 6240
ggacugcccc aucccaugcu ccggauccug gcuccgcgac gugugggacu ggguuugcac 6300
caucuugaca gacuucaaaa auuggcugac cucuaaauug uuccccaagc ugcccggccu 6360
ccccuucauc ucuugucaaa aggggauacaa gggugugugg gccggcacug gcaucaugac 6420
cacgcgcugc ccuugcggcg ccaacaucuc uggcaauguc cgccugggcu cuaugaggau 6480
cacagggccu aaaaccugca ugaacaccug gcaggggacc uuuccuauca auugcuacac 6540
ggagggccag ugcgcgccga aaccccccac gaacuacaag accgccaucu ggagggguggc 6600 ggccucggag uacgcggagg ugacgcagca ugggucguac uccuauguaa caggacugac 6660
cacugacaau cugaaaauuc cuugccaacu accuucucca gaguuuuucu ccugggugga 6720
cggugugcag auccauaggu uugcacccac accaaagccg uuuuuccggg augaggucuc 6780
guucugcguu gggcuuaauu ccuaugcugu cgggucccag cuucccugug aaccugagcc 6840
cgacgcagac guauugaggu ccaugcuaac agauccgccc cacaucacgg cggagacugc 6900
ggcgcggcgc uuggcacggg gaucaccucc aucugaggcg agcuccucag ugagccagcu 6960
aucagcaccg ucgcugcggg ccaccugcac cacccacagc aacaccuaug acguggacau 7020
ggucgaugcc aaccugcuca uggagggcgg uguggcucag acagagccug aguccagggu 7080
gcccguucug gacuuucucg agccaauggc cgaggaagag agcgaccuug agcccucaau 7140
accaucggag ugcaugcucc ccaggagcgg guuuccacgg gccuuaccgg cuugggcacg 7200
gccugacuac aacccgccgc ucguggaauc guggaggagg ccagauuacc aaccgcccac 7260
cguugcuggu ugugcucucc cccccccaa gaaggccccg acgccucccc caaggagacg 7320
ccggacagug ggucugagcg agagcaccau aucagaagcc cuccagcaac uggccaucaa 7380
gaccuuuggc cagccccccu cgagcgguga ugcaggcucg uccacggggg cgggcgccgc 7440
cgaauccggc gguccgacgu ccccugguga gccggccccc ucagagacag guuccgccuc 7500
cucuaugccc ccccucgagg gggagccugg agauccggac cuggagucug aucagguaga 7560
gcuucaaccu ccccccccagg gggggggggu agcucccggu ucgggcucgg ggucuugguc 7620
uacuugcucc gaggaggacg auaccaccgu gugcugcucc augucauacu ccuggaccgg 7680
ggcucuaaua acucccugua gccccgaaga ggaaaaguug ccaaucaacc cuuugaguaa 7740
cucgcuguug cgauaccaua acaaggugua cuguacaaca ucaaagagcg ccucacagag 7800
ggcuaaaaag guaacuuuug acaggacgca agugcucgac gcccauuaug acucagucuu 7860
aaaggacauc aagcuagcgg cuuccaaggu cagcgcaagg cuccucaccu uggaggaggc 7920
gugccaguug acuccacccc auucugcaag auccaaguau ggauucgggg ccaaggaggu 7980
ccgcagcuug uccgggaggg ccguuaacca caucaagucc guguggaagg accuccugga 8040
agacccacaa acaccaauuc ccacaaccau cauggccaaa aaugaggugu ucugcgugga 8100
ccccgccaag ggggguaaga aaccagcucg ccucaucguu uacccugacc ucggcguccg 8160
ggucugcgag aaaauggccc ucuaugacau uacacaaaag cuuccucagg cgguaauggg 8220
agcuuccuau ggcuuccagu acucccccugc ccaacgggug gaguaucucu ugaaagcaug 8280
ggcggaaaag aaggacccca uggguuuuuc guaugauacc cgaugcuucg acucaaccgu 8340

-continued cacugagaga gacaucagga ccgaggaguc cauauaccag gccugcuccc ugcccgagga 8400
ggcccgcacu gccauacacu cgcugacuga gagacuuuac guaggagggc ccauguucaa 8460
cagcaagggu caaaccugcg guuacagacg uugccgcgcc agcggggugc uaaccacuag 8520 caugggguaac accaucacau gcuaugugaa agcccuagcg gccugcaagg cugcggggau 8580
aguugcgccc acaaugcugg uaugcggcga ugaccuagua gucaucucag aaagccaggg 8640
gacugaggag gacgagcgga accugagagc cuucacggag gccaugacca gguacucugc 8700
cccuccuggu gaucccccca gaccggaaua ugaccuggag cuaauaacau ccuguuccuc 8760
aaaugugucu guggcguugg gcccgcgggg ccgccgcaga uacuaccuga ccagagaccc 8820
aaccacucca cucgcccggg cugccuggga aacaguuaga cacuccccua ucaauucaug 8880
gcugggaaac aucauccagu augcuccaac cauaugggguu cgcauggucc uaaugacaca 8940
cuucuucucc auucucaugg uccaagacac ccuggaccag aaccucaacu uugagaugua 9000
uggaucagua uacuccguga auccuuugga ccuuccagcc auaauugaga gguuacacgg 9060
gcuugacgcc uuuucuaugc acacauacuc ucaccacgaa cugacgcggg uggcuucagc 9120
ccucagaaaa cuuggggcgc caccccucag gguguggaag agucgggcuc gcgcagucag 9180
ggcgucccuc aucucccgug gagggaaagc ggccguuugc ggccgauauc ucuucaauug 9240
ggcggugaag accaagcuca aacucacucc auugccggag gcgcgccuac uggacuuauc 9300
caguugguuc accgucggcg ccggcggggg cgacauuuuu cacagcgugu cgcgcgcccg 9360
accccgcuca uuacucuucg gccuacuccu acuuuucgua gggguaggcc ucuuccuacu 9420
ccccgcucgg uagagcggca cacacuaggu acacuccaua gcuaacuguu ccuuuuuuuu 9480
uuuuuuuuuu uuuuuuuuuu uuuuuuuuuu uuuuucuuuu uuuuuuuuuu cccucuuucu 9540
ucccuucuca ucuuauucua cuuucuuucu ugguggcucc aucuuagccc uagucacggc 9600
uagcugugaa agguccguga gccgcaugac ugcagagagu gccguaacug gucucucugc 9660
agaucaugu 9669

<210> SEQ ID NO 4
<211> LENGTH: 9669
<212> TYPE: RNA
<213> ORGANISM: Artificial
<220> FEATURE:
<223> OTHER INFORMATION: pTH/JFH1(PT)

<400> SEQUENCE: 4 accugcccu aauaggggcg acacuccgcc augaaucacu ccccugugag gaacuacugu 60
cuucacgcag aaagcgccua gccauggcgu uaguaugagu gucguacagc cuccaggccc 120
cccccucccg ggagagccau aguggucugc ggaaccggug aguacaccgg aauugccggg 180
aagacugggu ccuuucuugg auaaacccac ucuaugcccg gccauuuggg cgugcccccg 240
caagacugcu agccgaguag cguuggguug cgaaaggccu ugugguacug ccugauaggg 300
cgcuugcgag ugccccggga ggucucguag accgugcacc augagcacga auccuaaacc 360
ucaaagaaaa accaaacgua acaccaaccg ccgcccacag gacgucaagu ucccgggcgg 420
uggccagauc guugguggag uuuaccuguu gccgcgcagg ggccccaggu ugggugugcg 480
cgcgacuagg aagacuuccg agcggucgca accucgugga aggcgacaac cuauccccaa 540
ggaucgccga cccgagggca gggccugggc ucagccuggg uacccuuggc cccucuaugg 600
caacgagggc augggguggg caggauggcu ccugucaccc cguggcuccc ggccuaguug 660
gggccccaau gacccccggc gcaggucgcg uaauuugggu aaagucaucg auacccuuac 720

-continued augcggcuuc gccgaccuca uggggguacau uccgcucguc ggcgcucccu ugggggggcgc 780 ugccagggcc uuggcgcaug gcguccgggu ucuggaggac ggcgugaacu augcaacagg 840
gaaucugccc gguugcucuu ucucuaucuu ccucuuggcu cugcuguccu gucuaaccau 900
cccagcuucc gcuuaugaag ugcgcaacgu guccggggug uaccauguca cgaacgacug 960
cuccaacucg agcauugugu acgagacagg ggacaugauu augcacaccc cugggugcgu 1020
gcccuguguu cgggagaaca acuccucccg cugcugggca gcgcucacuc ccacgcucgc 1080
ggccaggaac gccagcgucc ccaccacgac aauacggcgc cacgucgauu ugcucguugg 1140
ggcggcugcu uucugcuccg cuauguacgu gggggaucuc ugcggaucug uuuuccucgu 1200
cucccaguug uucaccuucu cgccucgccg gcaugagaca gugcaggacu gcaauuguuc 1260
aaucuauccc ggccacguau caggucaccg cauggcuugg gauaugauga ugaacugguc 1320
aacuacaaca gcccuacugg uaucgcaguu acuccggauc ccacaagccg ucguggacau 1380
gguggcgggg gcccacuggg gaguccuggc gggccuugcc uacuauucca uggcggggaa 1440
cugggcuaag guuuugauug ugcugcuacu cuuugccggc guugaugggg cgaccuacgu 1500 gacgggggggg ucggaagcca gaggggccuc uggcuuagca aaccucuuuu cauuuggggc 1560
gucucagaag auccagcuca uaaauaccaa cggcaguugg cacaucaaua gaacugcccu 1620
gaacugcaau gacucccucc acacuggguu ucuugccgcg cuauucuaca cacacaaauu 1680
caacgcgucc ggauguccag agcgcauggc cagcugccgc cccauugaag aguucgcuca 1740
gggguauggu cccaucacuu augcugagcc cuccccccucg gaccagaggc ccuauugcug 1800
gcacuacgcg ccucgaccgu gugguaucau acccgcgucg caggugugug guccagugua 1860
cugcuucacc ccaagcccug uuguggugggg gacgaccgau cgcuccggug cccccacgua 1920
uaauuggggg gcgaaugaga cggacgugcu guaucucaac aacacgcggc cgccgcaagg 1980
caacugguuc ggcugcacau ggaugaaugg caccggguuc accaagacgu gcgggggcccc 2040 cccgugcaac aucggggggg gcggcaacaa caacaccuug accugcccca cggacuguuu 2100
ccggaaacac cccgaggcca ccuacaccaa auguggguucg ggaccuuggu ugacaccuag 2160
gugcaugguc gacuacccau acaggcucug gcacuacccc ugcaccguua acuuuaccau 2220
cuuuaagguu aggauguacg ugggaggugu ggagcacagg cucaacgccg caugcaauug 2280
gacccgagga gagcguugua acuuagagga cagggauaga ucagagcuua gcccgcugcu 2340
gcugucaaca acagaguggc aggugcuacc uuguuccuuc accacccuac cggcucuguc 2400
cacugguuug auccaucucc accagaacau cguggacgug caauaccugu acgguauagg 2460
gucggcgguu gucuccuaug caaucaaaug ggaauauguc uuguugcucu uccuccuccu 2520
ggcagacgcg cgcgucugcg ccugcuugug gaugaugcug cugauagcuc aagcugaggc 2580
cgccuuagag aaccuggugg uccucaaugc ggcgucccug gcuggagcgc auggccuucu 2640
cucuuuccuu guguucuucu gugccgcuug guacaucaag ggcagguuga uccccggggc 2700
ggcguaugcu uuuuacggcg uauggccgcu gcuccuacuc cugcuggcgu uaccaccacg 2760
agcauacgcc auggaccggg agauggcugc aucgugcgga ggcgcgguuu uuguaggucu 2820
ggcauuccug accuugucac cacacuauaa ggcauuccuc gccaagcucc ugugguggguu 2880 gugcuaucuc cugacccugg gggaagccau gauucaggag uggguaccac ccaugcaggu 2940
gcgcggcggc cgcgauggca ucgcgugggc cgucacuaua uucugcccgg guguggugguu 3000 ugacauuacc aaauggcuuu uggcguugcu ugggccugcu uaccucuuaa gggccgcuuu 3060
gacacaugug ccguacuucg ucagagcuca cgcucugaua aggguaugcg cuuuggugaa 3120

-continued

```
gcagcucgcg ggggguaggu auguucaggu ggcgcuauug gcccuuggca gguggacugg   3180
caccuacauc uaugaccacc ucacaccuau gucggacugg gccgcuagcg gccugcgcga   3240
cuuagcgguc gccguggaac ccaucaucuu caguccgaug gagaagaagg ucaucgucug   3300
gggagcggag acggcugcau guggggacau ucuacaugga cuucccgugu ccgcccgacu   3360
cggccaggag auccuccucg gcccagcuga uggcuacacc uccaaggggu ggaagcuccu   3420
ugcucccauc acugcuuaug cccagcaaac acgaggccuc cugggcgcca uaguggugag   3480
uaugacgggg cgugacagga cagaacaggc cggggaaguc caaauccugu ccacagucuc   3540
ucaguccuuc cucggaacaa ccaucucggg gguuuugugg acuguuuacc acggagcugg   3600
caacaagacu cuagccggcu uacggggucc ggucacgcag auguacucga gugcugaggg   3660
ggacuuggua ggcuggccca gcccccccugg gaccaagucu uuggagccgu gcaagugugg   3720
agccgucgac cuauaucugg ucacgcggaa cgcugauguc aucccggcuc ggagacgcgg   3780
ggacaagcgg ggagcauugc ucuccccgag acccauuucg accuugaagg gguccucggg   3840
ggggccggug cucugcccua ggggccacgu cguugggcuc uuccgagcag cugugugcuc   3900
ucggggcgug gccaaaucca ucgauuucau ccccguugag acacucgacg uuguuacaag   3960
gucucccacu uucagugaca acagcacgcc accggcugug ccccagaccu aucaggucgg   4020
guacuugcau gcuccaacug gcaguggaaa gagcaccaag gucccugucg cguaugccgc   4080
ccaggggguac aaaguacuag ugcuuaaccc cucgguagcu gccacccugg gguuuggggc   4140
guaccuaucc aaggcacaug gcaucaaucc caacauuagg acuggaguca ggaccgugau   4200
gaccggggag gccaucacgu acuccacaua uggcaaauuu cucgccgaug ggggcugcgc   4260
uagcggcgcc uaugacauca ucauaugcga ugaaugccac gcuguggaug cuaccuccau   4320
ucucggcauc ggaacggucc uugaucaagc agagacagcc ggggucagac uaacugugcu   4380
ggcuacggcc acaccccccg ggucagugac aacccccccau cccgauauag aagagguagg   4440
ccucgggcgg gagggugaga uccccuucua ugggagggcg auuccccuau ccugcaucaa   4500
gggagggaga caccugauuu ucugccacuc aaagaaaaag ugugacgagc ucgcggcggc   4560
ccuucggggc augggcuuga augccguggc auacuauaga ggguuggacg ucuccauaau   4620
accagcucag ggagaugugg uggucgucgc caccgacgcc cucaugacgg gguacacugg   4680
agacuuugac uccgugaucg acugcaaugu agcggucacc caagcugucg acuucagccu   4740
ggaccccacc uucacuauaa ccacacagac ugucccacaa gacgcugucu cacgcaguca   4800
gcgccgcggg cgcacaggua gaggaagaca gggcacuuau agguauguuu ccacugguga   4860
acgagccuca ggaauguuug acaguguagu gcuuugugag ugcuacgacg caggggcugc   4920
gugguacgau cucacaccag cggagaccac cgucaggcuu agagcguauu ucaacacgcc   4980
cggccuaccc gugugucaag accaucuuga auuugggag gcaguuuuca ccggccucac   5040
acacauagac gcccacuucc ucucccaaac aaagcaagcg gggggagaacu ucgcguaccu   5100
aguagccuac caagcuacgg ugugcgccag agccaaggcc ccucccccgu ccugggacgc   5160
cauguggaag ugccuggccc gacucaagcc uacgcuugcg ggccccacac cucuccugua   5220
ccguuugggc ccuauuacca augaggucac ccucacacac ccugggacga aguacaucgc   5280
cacaugcaug caagcugacc uugaggucau gaccagcacg uggguccuag cuggaggagu   5340
ccuggcagcc gucgccgcau auugccuggc gacuggaugc guuuccauca ucggccgcuu   5400
gcacgucaac cagcgagucg ucguugcgcc ggauaaggag guccuguaug aggcuuuuga   5460
ugagauggag gaaugcgccu cuagggcggc ucucaucgaa gaggggcagc ggauagccga   5520
```

-continued

```
gauguugaag uccaagaucc aaggcuugcu gcagcaggcc ucuaagcagg cccaggacau   5580
acaacccgcu augcaggcuu cauggcccaa aguggaacaa uuuugggcca gacacaugug   5640
gaacuucauu agcggcaucc aauaccucgc aggauuguca acacugccag ggaaccccgc   5700
gguggcuucc augauggcau ucagugccgc ccucaccagu ccguugucga ccaguaccac   5760
cauccuucuc aacaucaugg gaggcugguu agcgucccag aucgcaccac ccgcgggggc   5820
caccggcuuu gucgucagug gccugguggg ggcugccgug ggcagcauag gccuggguaa   5880
ggugcuggug gacauccugg caggauaugg ugcgggcauu ucgggggccc ucgucgcauu   5940
caagaucaug ucuggcgaga agcccucuau ggaagauguc aucaaucuac ugccugggau   6000
ccugucuccg ggagcccugg uggugggggu caucugcgcg gccauucugc gccgccacgu   6060
gggaccgggg gagggcgcgg uccaauggau gaacaggcuu auugccuuug cuuccagagg   6120
aaaccacguc gccccuacuc acuacgugac ggagucggau gcgucgcagc gugugaccca   6180
acuacuuggc ucucuuacua uaaccagccu acucagaaga cuccacaauu ggauaacuga   6240
ggacugcccc aucccaugcu ccggauccug gcuccgcgac gugugggacu ggguuugcac   6300
caucuugaca gacuucaaaa auuggcugac cucuaaauug uuccccaagc ugcccggccu   6360
ccccuucauc ucuugucaaa agggguacaa gggugugugg gccggcacug gcaucaugac   6420
cacgcgcugc ccuugcggcg ccaacaucuc uggcaauguc cgccugggcu cuaugaggau   6480
cacagggccu aaaaccugca ugaacaccug gcaggggacc uuuccuauca auugcuacac   6540
ggagggccag ugcgcgccga aacccccac gaacuacaag accgccaucu ggagggugc   6600
ggccucggag uacgcggagg ugacgcagca ugggucguac ucccuaugua caggacugac   6660
cacugacaau cugaaaauuc cuugccaacu accuucucca gaguuuuucu ccugggugga   6720
cggugugcag auccauaggu uugcacccac accaaagccg uuuuuccggg augaggucuc   6780
guucugcguu gggcuuaauu ccuaugcugu cgggucccag cuucccugug aaccugagcc   6840
cgacgcagac guauugaggu ccaugcuaac agauccgccc cacaucacgg cggagacugc   6900
ggcgcggcgc uuggcacggg gaucaccucc aucugaggcg agcuccucag ugagccagcu   6960
aucagcaccg ucgcugcggg ccaccugcac cacccacagc aacaccuaug acguggacau   7020
ggucgaugcc aaccugcuca uggagggcgg uguggcucag acagagccug aguccagggu   7080
gcccguucug gacuuucucg agccaauggc cgaggaagag agcgaccuug agcccucaau   7140
accaucggag ugcaugcucc ccaggagcgg guuuccacgg gccuuaccgg cuugggcacg   7200
gccugacuac aacccgccgc ucguggaauc guggaggagg ccagauuacc aaccgcccac   7260
cguugcuggu ugugcucucc cccccccaa gaaggccccg acgccucccc caaggagacg   7320
ccggacagug ggucugagcg agagcaccau aucagaagcc cuccagcaac uggccaucaa   7380
gaccuuuggc cagcccccu cgagcgguga ugcaggcucg uccacggggg cgggcgccgc   7440
cgaauccggc gguccgacgu ccccugguga gccggccccc ucagagacag guuccgccuc   7500
cucuaugccc cccucgagg gggagccugg agauccggac cuggagucug aucagguaga   7560
gcuucaaccu cccccccagg ggggggggu agcucccggu ucgggcucgg ggucuugguc   7620
uacuugcucc gaggaggacg auaccaccgu gugcugcucc augucauacu ccuggaccgg   7680
ggcucuaaua acucccugua gccccgaaga ggaaaaguug ccaaucaacc cuuugaguaa   7740
cucgcuguug cgauaccaua acaaggugua cuguacaaca ucaaagagcg ccucacagag   7800
ggcuaaaaag guaacuuuug acaggacgca agugcucgac gcccauuaug acucagucuu   7860
aaaggacauc aagcuagcgg cuuccaaggu cagcgcaagg cuccucaccu uggaggaggc   7920
```

gugccaguug acuccacccc auucugcaag auccaaguau ggauucgggg ccaaggaggu 7980
ccgcagcuug uccgggaggg ccguuaacca caucaagucc guguggaagg accuccugga 8040
agacccacaa acaccaauuc ccacaaccau cauggccaaa aaugaggugu ucugcgugga 8100
ccccgccaag gggguaaga aaccagcucg ccucaucguu uacccugacc ucggcguccg 8160
ggucugcgag aaaauggccc ucuaugacau uacacaaaag cuuccucagg cgguaauggg 8220
agcuuccuau ggcuuccagu acuccccugc ccaacgggug gaguaucucu ugaaagcaug 8280
ggcggaaaag aaggacccca uggguuuuuc guaugauacc cgaugcuucg acucaaccgu 8340
cacugagaga gacaucagga ccgaggaguc cauauaccag gccugcuccc ugcccgagga 8400
ggcccgcacu gccauacacu cgcugacuga gagacuuuac guaggagggc ccauguucaa 8460
cagcaagggu caaaccugcg guuacagacg uugccgcgcc agcggggugc uaaccacuag 8520 caugggguaac accaucacau gcuaugugaa agcccuagcg gccugcaagg cugcggggau 8580
aguugcgccc acaaugcugg uaugcggcga ugaccuagua gucaucucag aaagccaggg 8640
gacugaggag gacgagcgga accugagagc cuucacggag gccaugacca gguacucugc 8700
cccuccuggu gaucccccca gaccggaaua ugaccuggag cuaauaacau ccuguuccuc 8760
aaaugugucu guggcguugg gcccgcgggg ccgccgcaga uacuaccuga ccagagaccc 8820
aaccacucca cucgcccggg cugccuggga aacaguuaga cacuccccua ucaauucaug 8880
gcugggaaac aucauccagu augcuccaac cauaugggu cgcauggucc uaaugacaca 8940
cuucuucucc auucucaugg uccaagacac ccuggaccag aaccucaacu uugagaugua 9000
uggaucagua uacuccguga auccuuugga ccuuccagcc auaauugaga gguuacacgg 9060
gcuugacgcc uuuucuaugc acacauacuc ucaccacgaa cugacgcggg uggcuucagc 9120
ccucagaaaa cuuggggcgc caccccucag gguguggaag agucgggcuc gcgcagucag 9180
ggcgucccuc aucucccgug gagggaaagc ggccguuugc ggccgauauc ucuucaauug 9240
ggcggugaag accaagcuca aacucacucc auugccggag gcgcgccuac uggacuuauc 9300
caguugguuc accgucggcg ccggcggggg cgacauuuuu cacagcgugu cgcgcgcccg 9360
accccgcuca uuacucuucg gccuacuccu acuuuucgua gggguaggcc ucuuccuacu 9420
ccccgcucgg uagagcggca cacacuaggu acacuccaua gcuaacuguu ccuuuuuuuu 9480
uuuuuuuuuu uuuuuuuuuu uuuuuuuuuu uuuuucuuuu uuuuuuuuuu cccucuuucu 9540
ucccuucuca ucuuauucua cuuucuuucu ugguggcucc aucuuagccc uagucacggc 9600
uagcugugaa agguccguga gccgcaugac ugcagagagu gccguaacug gucucucugc 9660
agaucaugu 9669

<210> SEQ ID NO 5
<211> LENGTH: 3030
<212> TYPE: PRT
<213> ORGANISM: Artificial
<220> FEATURE:
<223> OTHER INFORMATION: TH/JFH-1

<400> SEQUENCE: 5

Met Ser Thr Asn Pro Lys Pro Gln Arg Lys Thr Lys Arg Asn Thr Asn
1 5 10 15

Arg Arg Pro Gln Asp Val Lys Phe Pro Gly Gly Gly Gln Ile Val Gly
20 25 30

Gly Val Tyr Leu Leu Pro Arg Arg Gly Pro Arg Leu Gly Val Arg Ala
35 40 45

Thr Arg Lys Thr Ser Glu Arg Ser Gln Pro Arg Gly Arg Arg Gln Pro

-continued

```
    50                  55                  60

Ile Pro Lys Asp Arg Arg Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Val Tyr His Val Thr Asn Asp Cys Ser
        195                 200                 205

Asn Ser Ser Ile Val Tyr Glu Thr Gly Asp Met Ile Met His Thr Pro
    210                 215                 220

Gly Cys Val Pro Cys Val Arg Glu Asn Asn Ser Ser Arg Cys Trp Ala
225                 230                 235                 240

Ala Leu Thr Pro Thr Leu Ala Ala Arg Asn Ala Ser Val Pro Thr Thr
                245                 250                 255

Thr Ile Arg Arg His Val Asp Leu Leu Val Gly Ala Ala Ala Phe Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg His Glu Thr Val Gln Asp Cys
    290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Leu Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Ala Gly Asn Trp
        355                 360                 365

Ala Lys Val Leu Ile Val Leu Leu Leu Phe Ala Gly Val Asp Gly Ala
    370                 375                 380

Thr Tyr Val Thr Gly Gly Ser Glu Ala Arg Gly Ala Ser Gly Leu Ala
385                 390                 395                 400

Asn Leu Phe Ser Phe Gly Ala Ser Gln Lys Ile Gln Leu Ile Asn Thr
                405                 410                 415

Asn Gly Ser Trp His Ile Asn Arg Thr Ala Leu Asn Cys Asn Asp Ser
            420                 425                 430

Leu His Thr Gly Phe Leu Ala Ala Leu Phe Tyr Thr His Lys Phe Asn
        435                 440                 445

Ala Ser Gly Cys Pro Glu Arg Met Ala Ser Cys Arg Pro Ile Glu Glu
    450                 455                 460

Phe Ala Gln Gly Tyr Gly Pro Ile Thr Tyr Ala Glu Pro Ser Pro Ser
465                 470                 475                 480
```

-continued

```
Asp Gln Arg Pro Tyr Cys Trp His Tyr Ala Pro Arg Pro Cys Gly Ile
                485                 490                 495

Ile Pro Ala Ser Gln Val Cys Gly Pro Val Tyr Cys Phe Thr Pro Ser
            500                 505                 510

Pro Val Val Val Gly Thr Thr Asp Arg Ser Gly Ala Pro Thr Tyr Asn
        515                 520                 525

Trp Gly Ala Asn Glu Thr Asp Val Leu Tyr Leu Asn Asn Thr Arg Pro
    530                 535                 540

Pro Gln Gly Asn Trp Phe Gly Cys Thr Trp Met Asn Gly Thr Gly Phe
545                 550                 555                 560

Thr Lys Thr Cys Gly Gly Pro Pro Cys Asn Ile Gly Gly Gly Gly Asn
                565                 570                 575

Asn Asn Thr Leu Thr Cys Pro Thr Asp Cys Phe Arg Lys His Pro Glu
            580                 585                 590

Ala Thr Tyr Thr Lys Cys Gly Ser Gly Pro Trp Leu Thr Pro Arg Cys
        595                 600                 605

Met Val Asp Tyr Pro Tyr Arg Leu Trp His Tyr Pro Cys Thr Val Asn
    610                 615                 620

Phe Thr Ile Phe Lys Val Arg Met Tyr Val Gly Gly Val Glu His Arg
625                 630                 635                 640

Leu Asn Ala Ala Cys Asn Trp Thr Arg Gly Glu Arg Cys Asn Leu Glu
                645                 650                 655

Asp Arg Asp Arg Ser Glu Leu Ser Pro Leu Leu Leu Ser Thr Thr Glu
            660                 665                 670

Trp Gln Val Leu Pro Cys Ser Phe Thr Thr Leu Pro Ala Leu Ser Thr
        675                 680                 685

Gly Leu Ile His Leu His Gln Asn Ile Val Asp Val Gln Tyr Leu Tyr
    690                 695                 700

Gly Ile Gly Ser Ala Val Val Ser Tyr Ala Ile Lys Trp Glu Tyr Val
705                 710                 715                 720

Leu Leu Leu Phe Leu Leu Leu Ala Asp Ala Arg Val Cys Ala Cys Leu
                725                 730                 735

Trp Met Met Leu Leu Ile Ala Gln Ala Glu Ala Ala Leu Glu Asn Leu
            740                 745                 750

Val Val Leu Asn Ala Ala Ser Leu Ala Gly Ala His Gly Leu Leu Ser
        755                 760                 765

Phe Leu Val Phe Phe Cys Ala Ala Trp Tyr Ile Lys Gly Arg Leu Ile
    770                 775                 780

Pro Gly Ala Ala Tyr Ala Phe Tyr Gly Val Trp Pro Leu Leu Leu Leu
785                 790                 795                 800

Leu Leu Ala Leu Pro Pro Arg Ala Tyr Ala Met Asp Arg Glu Met Ala
                805                 810                 815

Ala Ser Cys Gly Gly Ala Val Phe Val Gly Leu Ala Phe Leu Thr Leu
            820                 825                 830

Ser Pro His Tyr Lys Ala Phe Leu Ala Lys Leu Leu Trp Trp Leu Cys
        835                 840                 845

Tyr Leu Leu Thr Leu Gly Glu Ala Met Ile Gln Glu Trp Val Pro Pro
    850                 855                 860

Met Gln Val Arg Gly Gly Arg Asp Gly Ile Ala Trp Ala Val Thr Ile
865                 870                 875                 880

Phe Cys Pro Gly Val Val Phe Asp Ile Thr Lys Trp Leu Leu Ala Leu
                885                 890                 895

Leu Gly Pro Ala Tyr Leu Leu Arg Ala Ala Leu Thr His Val Pro Tyr
            900                 905                 910
```

-continued

```
Phe Val Arg Ala His Ala Leu Ile Arg Val Cys Ala Leu Val Lys Gln
        915                 920                 925

Leu Ala Gly Gly Arg Tyr Val Gln Val Ala Leu Leu Ala Leu Gly Arg
    930                 935                 940

Trp Thr Gly Thr Tyr Ile Tyr Asp His Leu Thr Pro Met Ser Asp Trp
945                 950                 955                 960

Ala Ala Ser Gly Leu Arg Asp Leu Ala Val Ala Val Glu Pro Ile Ile
                965                 970                 975

Phe Ser Pro Met Glu Lys Lys Val Ile Val Trp Gly Ala Glu Thr Ala
            980                 985                 990

Ala Cys Gly Asp Ile Leu His Gly  Leu Pro Val Ser Ala  Arg Leu Gly
        995                 1000                1005

Gln Glu  Ile Leu Leu Gly Pro  Ala Asp Gly Tyr Thr  Ser Lys Gly
    1010                 1015                 1020

Trp Lys  Leu Leu Ala Pro Ile  Thr Ala Tyr Ala Gln  Gln Thr Arg
    1025                 1030                 1035

Gly Leu  Leu Gly Ala Ile Val  Val Ser Met Thr Gly  Arg Asp Arg
    1040                 1045                 1050

Thr Glu  Gln Ala Gly Glu Val  Gln Ile Leu Ser Thr  Val Ser Gln
    1055                 1060                 1065

Ser Phe  Leu Gly Thr Thr Ile  Ser Gly Val Leu Trp  Thr Val Tyr
    1070                 1075                 1080

His Gly  Ala Gly Asn Lys Thr  Leu Ala Gly Leu Arg  Gly Pro Val
    1085                 1090                 1095

Thr Gln  Met Tyr Ser Ser Ala  Glu Gly Asp Leu Val  Gly Trp Pro
    1100                 1105                 1110

Ser Pro  Pro Gly Thr Lys Ser  Leu Glu Pro Cys Lys  Cys Gly Ala
    1115                 1120                 1125

Val Asp  Leu Tyr Leu Val Thr  Arg Asn Ala Asp Val  Ile Pro Ala
    1130                 1135                 1140

Arg Arg  Arg Gly Asp Lys Arg  Gly Ala Leu Leu Ser  Pro Arg Pro
    1145                 1150                 1155

Ile Ser  Thr Leu Lys Gly Ser  Ser Gly Gly Pro Val  Leu Cys Pro
    1160                 1165                 1170

Arg Gly  His Val Val Gly Leu  Phe Arg Ala Ala Val  Cys Ser Arg
    1175                 1180                 1185

Gly Val  Ala Lys Ser Ile Asp  Phe Ile Pro Val Glu  Thr Leu Asp
    1190                 1195                 1200

Val Val  Thr Arg Ser Pro Thr  Phe Ser Asp Asn Ser  Thr Pro Pro
    1205                 1210                 1215

Ala Val  Pro Gln Thr Tyr Gln  Val Gly Tyr Leu His  Ala Pro Thr
    1220                 1225                 1230

Gly Ser  Gly Lys Ser Thr Lys  Val Pro Val Ala Tyr  Ala Ala Gln
    1235                 1240                 1245

Gly Tyr  Lys Val Leu Val Leu  Asn Pro Ser Val Ala  Ala Thr Leu
    1250                 1255                 1260

Gly Phe  Gly Ala Tyr Leu Ser  Lys Ala His Gly Ile  Asn Pro Asn
    1265                 1270                 1275

Ile Arg  Thr Gly Val Arg Thr  Val Met Thr Gly Glu  Ala Ile Thr
    1280                 1285                 1290

Tyr Ser  Thr Tyr Gly Lys Phe  Leu Ala Asp Gly Gly  Cys Ala Ser
    1295                 1300                 1305

Gly Ala  Tyr Asp Ile Ile Ile  Cys Asp Glu Cys His  Ala Val Asp
```

```
    1310                1315                1320

Ala Thr Ser Ile Leu Gly Ile Gly Thr Val Leu Asp Gln Ala Glu
    1325                1330                1335

Thr Ala Gly Val Arg Leu Thr Val Leu Ala Thr Ala Thr Pro Pro
    1340                1345                1350

Gly Ser Val Thr Thr Pro His Pro Asp Ile Glu Glu Val Gly Leu
    1355                1360                1365

Gly Arg Glu Gly Glu Ile Pro Phe Tyr Gly Arg Ala Ile Pro Leu
    1370                1375                1380

Ser Cys Ile Lys Gly Gly Arg His Leu Ile Phe Cys His Ser Lys
    1385                1390                1395

Lys Lys Cys Asp Glu Leu Ala Ala Ala Leu Arg Gly Met Gly Leu
    1400                1405                1410

Asn Ala Val Ala Tyr Tyr Arg Gly Leu Asp Val Ser Ile Ile Pro
    1415                1420                1425

Ala Gln Gly Asp Val Val Val Val Ala Thr Asp Ala Leu Met Thr
    1430                1435                1440

Gly Tyr Thr Gly Asp Phe Asp Ser Val Ile Asp Cys Asn Val Ala
    1445                1450                1455

Val Thr Gln Ala Val Asp Phe Ser Leu Asp Pro Thr Phe Thr Ile
    1460                1465                1470

Thr Thr Gln Thr Val Pro Gln Asp Ala Val Ser Arg Ser Gln Arg
    1475                1480                1485

Arg Gly Arg Thr Gly Arg Gly Arg Gln Gly Thr Tyr Arg Tyr Val
    1490                1495                1500

Ser Thr Gly Glu Arg Ala Ser Gly Met Phe Asp Ser Val Val Leu
    1505                1510                1515

Cys Glu Cys Tyr Asp Ala Gly Ala Ala Trp Tyr Asp Leu Thr Pro
    1520                1525                1530

Ala Glu Thr Thr Val Arg Leu Arg Ala Tyr Phe Asn Thr Pro Gly
    1535                1540                1545

Leu Pro Val Cys Gln Asp His Leu Glu Phe Trp Glu Ala Val Phe
    1550                1555                1560

Thr Gly Leu Thr His Ile Asp Ala His Phe Leu Ser Gln Thr Lys
    1565                1570                1575

Gln Ala Gly Glu Asn Phe Ala Tyr Leu Val Ala Tyr Gln Ala Thr
    1580                1585                1590

Val Cys Ala Arg Ala Lys Ala Pro Pro Pro Ser Trp Asp Ala Met
    1595                1600                1605

Trp Lys Cys Leu Ala Arg Leu Lys Pro Thr Leu Ala Gly Pro Thr
    1610                1615                1620

Pro Leu Leu Tyr Arg Leu Gly Pro Ile Thr Asn Glu Val Thr Leu
    1625                1630                1635

Thr His Pro Gly Thr Lys Tyr Ile Ala Thr Cys Met Gln Ala Asp
    1640                1645                1650

Leu Glu Val Met Thr Ser Thr Trp Val Leu Ala Gly Gly Val Leu
    1655                1660                1665

Ala Ala Val Ala Ala Tyr Cys Leu Ala Thr Gly Cys Val Ser Ile
    1670                1675                1680

Ile Gly Arg Leu His Val Asn Gln Arg Val Val Val Ala Pro Asp
    1685                1690                1695

Lys Glu Val Leu Tyr Glu Ala Phe Asp Glu Met Glu Glu Cys Ala
    1700                1705                1710
```

```
Ser Arg Ala Ala Leu Ile Glu Glu Gly Gln Arg Ile Ala Glu Met
    1715                1720                1725

Leu Lys Ser Lys Ile Gln Gly Leu Leu Gln Gln Ala Ser Lys Gln
    1730                1735                1740

Ala Gln Asp Ile Gln Pro Ala Met Gln Ala Ser Trp Pro Lys Val
    1745                1750                1755

Glu Gln Phe Trp Ala Arg His Met Trp Asn Phe Ile Ser Gly Ile
    1760                1765                1770

Gln Tyr Leu Ala Gly Leu Ser Thr Leu Pro Gly Asn Pro Ala Val
    1775                1780                1785

Ala Ser Met Met Ala Phe Ser Ala Ala Leu Thr Ser Pro Leu Ser
    1790                1795                1800

Thr Ser Thr Thr Ile Leu Leu Asn Ile Met Gly Gly Trp Leu Ala
    1805                1810                1815

Ser Gln Ile Ala Pro Pro Ala Gly Ala Thr Gly Phe Val Val Ser
    1820                1825                1830

Gly Leu Val Gly Ala Ala Val Gly Ser Ile Gly Leu Gly Lys Val
    1835                1840                1845

Leu Val Asp Ile Leu Ala Gly Tyr Gly Ala Gly Ile Ser Gly Ala
    1850                1855                1860

Leu Val Ala Phe Lys Ile Met Ser Gly Glu Lys Pro Ser Met Glu
    1865                1870                1875

Asp Val Ile Asn Leu Leu Pro Gly Ile Leu Ser Pro Gly Ala Leu
    1880                1885                1890

Val Val Gly Val Ile Cys Ala Ala Ile Leu Arg Arg His Val Gly
    1895                1900                1905

Pro Gly Glu Gly Ala Val Gln Trp Met Asn Arg Leu Ile Ala Phe
    1910                1915                1920

Ala Ser Arg Gly Asn His Val Ala Pro Thr His Tyr Val Thr Glu
    1925                1930                1935

Ser Asp Ala Ser Gln Arg Val Thr Gln Leu Leu Gly Ser Leu Thr
    1940                1945                1950

Ile Thr Ser Leu Leu Arg Arg Leu His Asn Trp Ile Thr Glu Asp
    1955                1960                1965

Cys Pro Ile Pro Cys Ser Gly Ser Trp Leu Arg Asp Val Trp Asp
    1970                1975                1980

Trp Val Cys Thr Ile Leu Thr Asp Phe Lys Asn Trp Leu Thr Ser
    1985                1990                1995

Lys Leu Phe Pro Lys Leu Pro Gly Leu Pro Phe Ile Ser Cys Gln
    2000                2005                2010

Lys Gly Tyr Lys Gly Val Trp Ala Gly Thr Gly Ile Met Thr Thr
    2015                2020                2025

Arg Cys Pro Cys Gly Ala Asn Ile Ser Gly Asn Val Arg Leu Gly
    2030                2035                2040

Ser Met Arg Ile Thr Gly Pro Lys Thr Cys Met Asn Thr Trp Gln
    2045                2050                2055

Gly Thr Phe Pro Ile Asn Cys Tyr Thr Glu Gly Gln Cys Ala Pro
    2060                2065                2070

Lys Pro Pro Thr Asn Tyr Lys Thr Ala Ile Trp Arg Val Ala Ala
    2075                2080                2085

Ser Glu Tyr Ala Glu Val Thr Gln His Gly Ser Tyr Ser Tyr Val
    2090                2095                2100

Thr Gly Leu Thr Thr Asp Asn Leu Lys Ile Pro Cys Gln Leu Pro
    2105                2110                2115
```

```
Ser Pro  Glu Phe Phe Ser Trp  Val Asp Gly Val Gln  Ile His Arg
    2120                 2125                 2130

Phe Ala  Pro Thr Pro Lys Pro  Phe Phe Arg Asp Glu  Val Ser Phe
    2135                 2140                 2145

Cys Val  Gly Leu Asn Ser Tyr  Ala Val Gly Ser Gln  Leu Pro Cys
    2150                 2155                 2160

Glu Pro  Glu Pro Asp Ala Asp  Val Leu Arg Ser Met  Leu Thr Asp
    2165                 2170                 2175

Pro Pro  His Ile Thr Ala Glu  Thr Ala Ala Arg Arg  Leu Ala Arg
    2180                 2185                 2190

Gly Ser  Pro Pro Ser Glu Ala  Ser Ser Ser Val Ser  Gln Leu Ser
    2195                 2200                 2205

Ala Pro  Ser Leu Arg Ala Thr  Cys Thr Thr His Ser  Asn Thr Tyr
    2210                 2215                 2220

Asp Val  Asp Met Val Asp Ala  Asn Leu Leu Met Glu  Gly Gly Val
    2225                 2230                 2235

Ala Gln  Thr Glu Pro Glu Ser  Arg Val Pro Val Leu  Asp Phe Leu
    2240                 2245                 2250

Glu Pro  Met Ala Glu Glu Glu  Ser Asp Leu Glu Pro  Ser Ile Pro
    2255                 2260                 2265

Ser Glu  Cys Met Leu Pro Arg  Ser Gly Phe Pro Arg  Ala Leu Pro
    2270                 2275                 2280

Ala Trp  Ala Arg Pro Asp Tyr  Asn Pro Pro Leu Val  Glu Ser Trp
    2285                 2290                 2295

Arg Arg  Pro Asp Tyr Gln Pro  Pro Thr Val Ala Gly  Cys Ala Leu
    2300                 2305                 2310

Pro Pro  Pro Lys Lys Ala Pro  Thr Pro Pro Pro Arg  Arg Arg Arg
    2315                 2320                 2325

Thr Val  Gly Leu Ser Glu Ser  Thr Ile Ser Glu Ala  Leu Gln Gln
    2330                 2335                 2340

Leu Ala  Ile Lys Thr Phe Gly  Gln Pro Pro Ser Ser  Gly Asp Ala
    2345                 2350                 2355

Gly Ser  Ser Thr Gly Ala Gly  Ala Ala Glu Ser Gly  Gly Pro Thr
    2360                 2365                 2370

Ser Pro  Gly Glu Pro Ala Pro  Ser Glu Thr Gly Ser  Ala Ser Ser
    2375                 2380                 2385

Met Pro  Pro Leu Glu Gly Glu  Pro Gly Asp Pro Asp  Leu Glu Ser
    2390                 2395                 2400

Asp Gln  Val Glu Leu Gln Pro  Pro Pro Gln Gly Gly  Gly Val Ala
    2405                 2410                 2415

Pro Gly  Ser Gly Ser Gly Ser  Trp Ser Thr Cys Ser  Glu Glu Asp
    2420                 2425                 2430

Asp Thr  Thr Val Cys Cys Ser  Met Ser Tyr Ser Trp  Thr Gly Ala
    2435                 2440                 2445

Leu Ile  Thr Pro Cys Ser Pro  Glu Glu Glu Lys Leu  Pro Ile Asn
    2450                 2455                 2460

Pro Leu  Ser Asn Ser Leu Leu  Arg Tyr His Asn Lys  Val Tyr Cys
    2465                 2470                 2475

Thr Thr  Ser Lys Ser Ala Ser  Gln Arg Ala Lys Lys  Val Thr Phe
    2480                 2485                 2490

Asp Arg  Thr Gln Val Leu Asp  Ala His Tyr Asp Ser  Val Leu Lys
    2495                 2500                 2505

Asp Ile  Lys Leu Ala Ala Ser  Lys Val Ser Ala Arg  Leu Leu Thr
```

-continued

```
    2510                2515                2520

Leu Glu  Glu Ala Cys Gln Leu  Thr Pro Pro His Ser  Ala Arg Ser
    2525                2530                2535

Lys Tyr  Gly Phe Gly Ala Lys  Glu Val Arg Ser Leu  Ser Gly Arg
    2540                2545                2550

Ala Val  Asn His Ile Lys Ser  Val Trp Lys Asp Leu  Leu Glu Asp
    2555                2560                2565

Pro Gln  Thr Pro Ile Pro Thr  Thr Ile Met Ala Lys  Asn Glu Val
    2570                2575                2580

Phe Cys  Val Asp Pro Ala Lys  Gly Gly Lys Lys Pro  Ala Arg Leu
    2585                2590                2595

Ile Val  Tyr Pro Asp Leu Gly  Val Arg Val Cys Glu  Lys Met Ala
    2600                2605                2610

Leu Tyr  Asp Ile Thr Gln Lys  Leu Pro Gln Ala Val  Met Gly Ala
    2615                2620                2625

Ser Tyr  Gly Phe Gln Tyr Ser  Pro Ala Gln Arg Val  Glu Tyr Leu
    2630                2635                2640

Leu Lys  Ala Trp Ala Glu Lys  Lys Asp Pro Met Gly  Phe Ser Tyr
    2645                2650                2655

Asp Thr  Arg Cys Phe Asp Ser  Thr Val Thr Glu Arg  Asp Ile Arg
    2660                2665                2670

Thr Glu  Glu Ser Ile Tyr Gln  Ala Cys Ser Leu Pro  Glu Glu Ala
    2675                2680                2685

Arg Thr  Ala Ile His Ser Leu  Thr Glu Arg Leu Tyr  Val Gly Gly
    2690                2695                2700

Pro Met  Phe Asn Ser Lys Gly  Gln Thr Cys Gly Tyr  Arg Arg Cys
    2705                2710                2715

Arg Ala  Ser Gly Val Leu Thr  Thr Ser Met Gly Asn  Thr Ile Thr
    2720                2725                2730

Cys Tyr  Val Lys Ala Leu Ala  Ala Cys Lys Ala Ala  Gly Ile Val
    2735                2740                2745

Ala Pro  Thr Met Leu Val Cys  Gly Asp Asp Leu Val  Val Ile Ser
    2750                2755                2760

Glu Ser  Gln Gly Thr Glu Glu  Asp Glu Arg Asn Leu  Arg Ala Phe
    2765                2770                2775

Thr Glu  Ala Met Thr Arg Tyr  Ser Ala Pro Pro Gly  Asp Pro Pro
    2780                2785                2790

Arg Pro  Glu Tyr Asp Leu Glu  Leu Ile Thr Ser Cys  Ser Ser Asn
    2795                2800                2805

Val Ser  Val Ala Leu Gly Pro  Arg Gly Arg Arg Arg  Tyr Tyr Leu
    2810                2815                2820

Thr Arg  Asp Pro Thr Thr Pro  Leu Ala Arg Ala Ala  Trp Glu Thr
    2825                2830                2835

Val Arg  His Ser Pro Ile Asn  Ser Trp Leu Gly Asn  Ile Ile Gln
    2840                2845                2850

Tyr Ala  Pro Thr Ile Trp Val  Arg Met Val Leu Met  Thr His Phe
    2855                2860                2865

Phe Ser  Ile Leu Met Val Gln  Asp Thr Leu Asp Gln  Asn Leu Asn
    2870                2875                2880

Phe Glu  Met Tyr Gly Ser Val  Tyr Ser Val Asn Pro  Leu Asp Leu
    2885                2890                2895

Pro Ala  Ile Ile Glu Arg Leu  His Gly Leu Asp Ala  Phe Ser Met
    2900                2905                2910
```

-continued

His Thr Tyr Ser His His Glu Leu Thr Arg Val Ala Ser Ala Leu
2915 2920 2925

Arg Lys Leu Gly Ala Pro Pro Leu Arg Val Trp Lys Ser Arg Ala
2930 2935 2940

Arg Ala Val Arg Ala Ser Leu Ile Ser Arg Gly Gly Lys Ala Ala
2945 2950 2955

Val Cys Gly Arg Tyr Leu Phe Asn Trp Ala Val Lys Thr Lys Leu
2960 2965 2970

Lys Leu Thr Pro Leu Pro Glu Ala Arg Leu Leu Asp Leu Ser Ser
2975 2980 2985

Trp Phe Thr Val Gly Ala Gly Gly Gly Asp Ile Phe His Ser Val
2990 2995 3000

Ser Arg Ala Arg Pro Arg Ser Leu Leu Phe Gly Leu Leu Leu Leu
3005 3010 3015

Phe Val Gly Val Gly Leu Phe Leu Leu Pro Ala Arg
3020 3025 3030

<210> SEQ ID NO 6
<211> LENGTH: 3030
<212> TYPE: PRT
<213> ORGANISM: Artificial
<220> FEATURE:
<223> OTHER INFORMATION: TH/JFH-1(PA)

<400> SEQUENCE: 6

Met Ser Thr Asn Pro Lys Pro Gln Arg Lys Thr Lys Arg Asn Thr Asn
1 5 10 15

Arg Arg Pro Gln Asp Val Lys Phe Pro Gly Gly Gly Gln Ile Val Gly
20 25 30

Gly Val Tyr Leu Leu Pro Arg Arg Gly Pro Arg Leu Gly Val Arg Ala
35 40 45

Thr Arg Lys Thr Ser Glu Arg Ser Gln Pro Arg Gly Arg Arg Gln Pro
50 55 60

Ile Pro Lys Asp Arg Arg Pro Glu Gly Arg Ala Trp Ala Gln Pro Gly
65 70 75 80

Tyr Pro Trp Pro Leu Tyr Gly Asn Glu Gly Met Gly Trp Ala Gly Trp
85 90 95

Leu Leu Ser Pro Arg Gly Ser Arg Pro Ser Trp Gly Pro Asn Asp Pro
100 105 110

Arg Arg Arg Ser Arg Asn Leu Gly Lys Val Ile Asp Thr Leu Thr Cys
115 120 125

Gly Phe Ala Asp Leu Met Gly Tyr Ile Pro Leu Val Gly Ala Pro Leu
130 135 140

Gly Gly Ala Ala Arg Ala Leu Ala His Gly Val Arg Val Leu Glu Asp
145 150 155 160

Gly Val Asn Tyr Ala Thr Gly Asn Leu Pro Gly Cys Ser Phe Ser Ile
165 170 175

Phe Leu Leu Ala Leu Leu Ser Cys Leu Thr Ile Pro Ala Ser Ala Tyr
180 185 190

Glu Val Arg Asn Val Ser Gly Val Tyr His Val Thr Asn Asp Cys Ser
195 200 205

Asn Ser Ser Ile Val Tyr Glu Thr Gly Asp Met Ile Met His Thr Pro
210 215 220

Gly Cys Val Pro Cys Val Arg Glu Asn Asn Ser Ser Arg Cys Trp Ala
225 230 235 240

Ala Leu Thr Pro Thr Leu Ala Ala Arg Asn Ala Ser Val Pro Thr Thr

```
                245                 250                 255

Thr Ile Arg Arg His Val Asp Leu Leu Val Gly Ala Ala Ala Phe Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg His Glu Thr Val Gln Asp Cys
    290                 295                 300

Asn Cys Ser Ile Tyr Pro Gly His Val Ser Gly His Arg Met Ala Trp
305                 310                 315                 320

Asp Met Met Met Asn Trp Ser Ala Thr Thr Ala Leu Leu Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Ala Gly Asn Trp
        355                 360                 365

Ala Lys Val Leu Ile Val Leu Leu Leu Phe Ala Gly Val Asp Gly Ala
    370                 375                 380

Thr Tyr Val Thr Gly Gly Ser Glu Ala Arg Gly Ala Ser Gly Leu Ala
385                 390                 395                 400

Asn Leu Phe Ser Phe Gly Ala Ser Gln Lys Ile Gln Leu Ile Asn Thr
                405                 410                 415

Asn Gly Ser Trp His Ile Asn Arg Thr Ala Leu Asn Cys Asn Asp Ser
            420                 425                 430

Leu His Thr Gly Phe Leu Ala Ala Leu Phe Tyr Thr His Lys Phe Asn
        435                 440                 445

Ala Ser Gly Cys Pro Glu Arg Met Ala Ser Cys Arg Pro Ile Glu Glu
    450                 455                 460

Phe Ala Gln Gly Tyr Gly Pro Ile Thr Tyr Ala Glu Pro Ser Pro Ser
465                 470                 475                 480

Asp Gln Arg Pro Tyr Cys Trp His Tyr Ala Pro Arg Pro Cys Gly Ile
                485                 490                 495

Ile Pro Ala Ser Gln Val Cys Gly Pro Val Tyr Cys Phe Thr Pro Ser
            500                 505                 510

Pro Val Val Val Gly Thr Thr Asp Arg Ser Gly Ala Pro Thr Tyr Asn
        515                 520                 525

Trp Gly Ala Asn Glu Thr Asp Val Leu Tyr Leu Asn Asn Thr Arg Pro
    530                 535                 540

Pro Gln Gly Asn Trp Phe Gly Cys Thr Trp Met Asn Gly Thr Gly Phe
545                 550                 555                 560

Thr Lys Thr Cys Gly Gly Pro Pro Cys Asn Ile Gly Gly Gly Gly Asn
                565                 570                 575

Asn Asn Thr Leu Thr Cys Pro Thr Asp Cys Phe Arg Lys His Pro Glu
            580                 585                 590

Ala Thr Tyr Thr Lys Cys Gly Ser Gly Pro Trp Leu Thr Pro Arg Cys
        595                 600                 605

Met Val Asp Tyr Pro Tyr Arg Leu Trp His Tyr Pro Cys Thr Val Asn
    610                 615                 620

Phe Thr Ile Phe Lys Val Arg Met Tyr Val Gly Gly Val Glu His Arg
625                 630                 635                 640

Leu Asn Ala Ala Cys Asn Trp Thr Arg Gly Glu Arg Cys Asn Leu Glu
                645                 650                 655

Asp Arg Asp Arg Ser Glu Leu Ser Pro Leu Leu Leu Ser Thr Thr Glu
            660                 665                 670
```

-continued

```
Trp Gln Val Leu Pro Cys Ser Phe Thr Thr Leu Pro Ala Leu Ser Thr
        675                 680                 685

Gly Leu Ile His Leu His Gln Asn Ile Val Asp Val Gln Tyr Leu Tyr
    690                 695                 700

Gly Ile Gly Ser Ala Val Val Ser Tyr Ala Ile Lys Trp Glu Tyr Val
705                 710                 715                 720

Leu Leu Leu Phe Leu Leu Leu Ala Asp Ala Arg Val Cys Ala Cys Leu
                725                 730                 735

Trp Met Met Leu Leu Ile Ala Gln Ala Glu Ala Ala Leu Glu Asn Leu
            740                 745                 750

Val Val Leu Asn Ala Ala Ser Leu Ala Gly Ala His Gly Leu Leu Ser
        755                 760                 765

Phe Leu Val Phe Phe Cys Ala Ala Trp Tyr Ile Lys Gly Arg Leu Ile
    770                 775                 780

Pro Gly Ala Ala Tyr Ala Phe Tyr Gly Val Trp Pro Leu Leu Leu Leu
785                 790                 795                 800

Leu Leu Ala Leu Pro Pro Arg Ala Tyr Ala Met Asp Arg Glu Met Ala
                805                 810                 815

Ala Ser Cys Gly Gly Ala Val Phe Val Gly Leu Ala Phe Leu Thr Leu
            820                 825                 830

Ser Pro His Tyr Lys Ala Phe Leu Ala Lys Leu Leu Trp Trp Leu Cys
        835                 840                 845

Tyr Leu Leu Thr Leu Gly Glu Ala Met Ile Gln Glu Trp Val Pro Pro
    850                 855                 860

Met Gln Val Arg Gly Gly Arg Asp Gly Ile Ala Trp Ala Val Thr Ile
865                 870                 875                 880

Phe Cys Pro Gly Val Val Phe Asp Ile Thr Lys Trp Leu Leu Ala Leu
                885                 890                 895

Leu Gly Pro Ala Tyr Leu Leu Arg Ala Ala Leu Thr His Val Pro Tyr
            900                 905                 910

Phe Val Arg Ala His Ala Leu Ile Arg Val Cys Ala Leu Val Lys Gln
        915                 920                 925

Leu Ala Gly Gly Arg Tyr Val Gln Val Ala Leu Leu Ala Leu Gly Arg
    930                 935                 940

Trp Thr Gly Thr Tyr Ile Tyr Asp His Leu Thr Pro Met Ser Asp Trp
945                 950                 955                 960

Ala Ala Ser Gly Leu Arg Asp Leu Ala Val Ala Val Glu Pro Ile Ile
                965                 970                 975

Phe Ser Pro Met Glu Lys Lys Val Ile Val Trp Gly Ala Glu Thr Ala
            980                 985                 990

Ala Cys Gly Asp Ile Leu His Gly  Leu Pro Val Ser Ala  Arg Leu Gly
        995                 1000                 1005

Gln Glu  Ile Leu Leu Gly Pro  Ala Asp Gly Tyr Thr  Ser Lys Gly
    1010                 1015                 1020

Trp Lys  Leu Leu Ala Pro Ile  Thr Ala Tyr Ala Gln  Gln Thr Arg
    1025                 1030                 1035

Gly Leu  Leu Gly Ala Ile Val  Val Ser Met Thr Gly  Arg Asp Arg
    1040                 1045                 1050

Thr Glu  Gln Ala Gly Glu Val  Gln Ile Leu Ser Thr  Val Ser Gln
    1055                 1060                 1065

Ser Phe  Leu Gly Thr Thr Ile  Ser Gly Val Leu Trp  Thr Val Tyr
    1070                 1075                 1080

His Gly  Ala Gly Asn Lys Thr  Leu Ala Gly Leu Arg  Gly Pro Val
    1085                 1090                 1095
```

```
Thr Gln  Met Tyr Ser Ser Ala  Glu Gly Asp Leu Val  Gly Trp Pro
    1100                 1105                 1110

Ser Pro  Pro Gly Thr Lys Ser  Leu Glu Pro Cys Lys  Cys Gly Ala
    1115                 1120                 1125

Val Asp  Leu Tyr Leu Val Thr  Arg Asn Ala Asp Val  Ile Pro Ala
    1130                 1135                 1140

Arg Arg  Arg Gly Asp Lys Arg  Gly Ala Leu Leu Ser  Pro Arg Pro
    1145                 1150                 1155

Ile Ser  Thr Leu Lys Gly Ser  Ser Gly Gly Pro Val  Leu Cys Pro
    1160                 1165                 1170

Arg Gly  His Val Val Gly Leu  Phe Arg Ala Ala Val  Cys Ser Arg
    1175                 1180                 1185

Gly Val  Ala Lys Ser Ile Asp  Phe Ile Pro Val Glu  Thr Leu Asp
    1190                 1195                 1200

Val Val  Thr Arg Ser Pro Thr  Phe Ser Asp Asn Ser  Thr Pro Pro
    1205                 1210                 1215

Ala Val  Pro Gln Thr Tyr Gln  Val Gly Tyr Leu His  Ala Pro Thr
    1220                 1225                 1230

Gly Ser  Gly Lys Ser Thr Lys  Val Pro Val Ala Tyr  Ala Ala Gln
    1235                 1240                 1245

Gly Tyr  Lys Val Leu Val Leu  Asn Pro Ser Val Ala  Ala Thr Leu
    1250                 1255                 1260

Gly Phe  Gly Ala Tyr Leu Ser  Lys Ala His Gly Ile  Asn Pro Asn
    1265                 1270                 1275

Ile Arg  Thr Gly Val Arg Thr  Val Met Thr Gly Glu  Ala Ile Thr
    1280                 1285                 1290

Tyr Ser  Thr Tyr Gly Lys Phe  Leu Ala Asp Gly Gly  Cys Ala Ser
    1295                 1300                 1305

Gly Ala  Tyr Asp Ile Ile Ile  Cys Asp Glu Cys His  Ala Val Asp
    1310                 1315                 1320

Ala Thr  Ser Ile Leu Gly Ile  Gly Thr Val Leu Asp  Gln Ala Glu
    1325                 1330                 1335

Thr Ala  Gly Val Arg Leu Thr  Val Leu Ala Thr Ala  Thr Pro Pro
    1340                 1345                 1350

Gly Ser  Val Thr Thr Pro His  Pro Asp Ile Glu Glu  Val Gly Leu
    1355                 1360                 1365

Gly Arg  Glu Gly Glu Ile Pro  Phe Tyr Gly Arg Ala  Ile Pro Leu
    1370                 1375                 1380

Ser Cys  Ile Lys Gly Gly Arg  His Leu Ile Phe Cys  His Ser Lys
    1385                 1390                 1395

Lys Lys  Cys Asp Glu Leu Ala  Ala Ala Leu Arg Gly  Met Gly Leu
    1400                 1405                 1410

Asn Ala  Val Ala Tyr Tyr Arg  Gly Leu Asp Val Ser  Ile Ile Pro
    1415                 1420                 1425

Ala Gln  Gly Asp Val Val Val  Val Ala Thr Asp Ala  Leu Met Thr
    1430                 1435                 1440

Gly Tyr  Thr Gly Asp Phe Asp  Ser Val Ile Asp Cys  Asn Val Ala
    1445                 1450                 1455

Val Thr  Gln Ala Val Asp Phe  Ser Leu Asp Pro Thr  Phe Thr Ile
    1460                 1465                 1470

Thr Thr  Gln Thr Val Pro Gln  Asp Ala Val Ser Arg  Ser Gln Arg
    1475                 1480                 1485

Arg Gly  Arg Thr Gly Arg Gly  Arg Gln Gly Thr Tyr  Arg Tyr Val
```

```
    1490                1495                1500

Ser Thr  Gly Glu Arg Ala Ser  Gly Met Phe Asp Ser  Val Val Leu
    1505                1510                1515

Cys Glu  Cys Tyr Asp Ala Gly  Ala Ala Trp Tyr Asp  Leu Thr Pro
    1520                1525                1530

Ala Glu  Thr Thr Val Arg Leu  Arg Ala Tyr Phe Asn  Thr Pro Gly
    1535                1540                1545

Leu Pro  Val Cys Gln Asp His  Leu Glu Phe Trp Glu  Ala Val Phe
    1550                1555                1560

Thr Gly  Leu Thr His Ile Asp  Ala His Phe Leu Ser  Gln Thr Lys
    1565                1570                1575

Gln Ala  Gly Glu Asn Phe Ala  Tyr Leu Val Ala Tyr  Gln Ala Thr
    1580                1585                1590

Val Cys  Ala Arg Ala Lys Ala  Pro Pro Pro Ser Trp  Asp Ala Met
    1595                1600                1605

Trp Lys  Cys Leu Ala Arg Leu  Lys Pro Thr Leu Ala  Gly Pro Thr
    1610                1615                1620

Pro Leu  Leu Tyr Arg Leu Gly  Pro Ile Thr Asn Glu  Val Thr Leu
    1625                1630                1635

Thr His  Pro Gly Thr Lys Tyr  Ile Ala Thr Cys Met  Gln Ala Asp
    1640                1645                1650

Leu Glu  Val Met Thr Ser Thr  Trp Val Leu Ala Gly  Gly Val Leu
    1655                1660                1665

Ala Ala  Val Ala Ala Tyr Cys  Leu Ala Thr Gly Cys  Val Ser Ile
    1670                1675                1680

Ile Gly  Arg Leu His Val Asn  Gln Arg Val Val Val  Ala Pro Asp
    1685                1690                1695

Lys Glu  Val Leu Tyr Glu Ala  Phe Asp Glu Met Glu  Glu Cys Ala
    1700                1705                1710

Ser Arg  Ala Ala Leu Ile Glu  Glu Gly Gln Arg Ile  Ala Glu Met
    1715                1720                1725

Leu Lys  Ser Lys Ile Gln Gly  Leu Leu Gln Gln Ala  Ser Lys Gln
    1730                1735                1740

Ala Gln  Asp Ile Gln Pro Ala  Met Gln Ala Ser Trp  Pro Lys Val
    1745                1750                1755

Glu Gln  Phe Trp Ala Arg His  Met Trp Asn Phe Ile  Ser Gly Ile
    1760                1765                1770

Gln Tyr  Leu Ala Gly Leu Ser  Thr Leu Pro Gly Asn  Pro Ala Val
    1775                1780                1785

Ala Ser  Met Met Ala Phe Ser  Ala Ala Leu Thr Ser  Pro Leu Ser
    1790                1795                1800

Thr Ser  Thr Thr Ile Leu Leu  Asn Ile Met Gly Gly  Trp Leu Ala
    1805                1810                1815

Ser Gln  Ile Ala Pro Pro Ala  Gly Ala Thr Gly Phe  Val Val Ser
    1820                1825                1830

Gly Leu  Val Gly Ala Ala Val  Gly Ser Ile Gly Leu  Gly Lys Val
    1835                1840                1845

Leu Val  Asp Ile Leu Ala Gly  Tyr Gly Ala Gly Ile  Ser Gly Ala
    1850                1855                1860

Leu Val  Ala Phe Lys Ile Met  Ser Gly Glu Lys Pro  Ser Met Glu
    1865                1870                1875

Asp Val  Ile Asn Leu Leu Pro  Gly Ile Leu Ser Pro  Gly Ala Leu
    1880                1885                1890
```

-continued

```
Val Val Gly Val Ile Cys Ala Ala Ile Leu Arg Arg His Val Gly
    1895                1900                1905

Pro Gly Glu Gly Ala Val Gln Trp Met Asn Arg Leu Ile Ala Phe
    1910                1915                1920

Ala Ser Arg Gly Asn His Val Ala Pro Thr His Tyr Val Thr Glu
    1925                1930                1935

Ser Asp Ala Ser Gln Arg Val Thr Gln Leu Leu Gly Ser Leu Thr
    1940                1945                1950

Ile Thr Ser Leu Leu Arg Arg Leu His Asn Trp Ile Thr Glu Asp
    1955                1960                1965

Cys Pro Ile Pro Cys Ser Gly Ser Trp Leu Arg Asp Val Trp Asp
    1970                1975                1980

Trp Val Cys Thr Ile Leu Thr Asp Phe Lys Asn Trp Leu Thr Ser
    1985                1990                1995

Lys Leu Phe Pro Lys Leu Pro Gly Leu Pro Phe Ile Ser Cys Gln
    2000                2005                2010

Lys Gly Tyr Lys Gly Val Trp Ala Gly Thr Gly Ile Met Thr Thr
    2015                2020                2025

Arg Cys Pro Cys Gly Ala Asn Ile Ser Gly Asn Val Arg Leu Gly
    2030                2035                2040

Ser Met Arg Ile Thr Gly Pro Lys Thr Cys Met Asn Thr Trp Gln
    2045                2050                2055

Gly Thr Phe Pro Ile Asn Cys Tyr Thr Glu Gly Gln Cys Ala Pro
    2060                2065                2070

Lys Pro Pro Thr Asn Tyr Lys Thr Ala Ile Trp Arg Val Ala Ala
    2075                2080                2085

Ser Glu Tyr Ala Glu Val Thr Gln His Gly Ser Tyr Ser Tyr Val
    2090                2095                2100

Thr Gly Leu Thr Thr Asp Asn Leu Lys Ile Pro Cys Gln Leu Pro
    2105                2110                2115

Ser Pro Glu Phe Phe Ser Trp Val Asp Gly Val Gln Ile His Arg
    2120                2125                2130

Phe Ala Pro Thr Pro Lys Pro Phe Phe Arg Asp Glu Val Ser Phe
    2135                2140                2145

Cys Val Gly Leu Asn Ser Tyr Ala Val Gly Ser Gln Leu Pro Cys
    2150                2155                2160

Glu Pro Glu Pro Asp Ala Asp Val Leu Arg Ser Met Leu Thr Asp
    2165                2170                2175

Pro Pro His Ile Thr Ala Glu Thr Ala Ala Arg Arg Leu Ala Arg
    2180                2185                2190

Gly Ser Pro Pro Ser Glu Ala Ser Ser Ser Val Ser Gln Leu Ser
    2195                2200                2205

Ala Pro Ser Leu Arg Ala Thr Cys Thr Thr His Ser Asn Thr Tyr
    2210                2215                2220

Asp Val Asp Met Val Asp Ala Asn Leu Leu Met Glu Gly Gly Val
    2225                2230                2235

Ala Gln Thr Glu Pro Glu Ser Arg Val Pro Val Leu Asp Phe Leu
    2240                2245                2250

Glu Pro Met Ala Glu Glu Glu Ser Asp Leu Glu Pro Ser Ile Pro
    2255                2260                2265

Ser Glu Cys Met Leu Pro Arg Ser Gly Phe Pro Arg Ala Leu Pro
    2270                2275                2280

Ala Trp Ala Arg Pro Asp Tyr Asn Pro Pro Leu Val Glu Ser Trp
    2285                2290                2295
```

-continued

```
Arg Arg  Pro Asp Tyr Gln Pro  Pro Thr Val Ala Gly  Cys Ala Leu
    2300                 2305                 2310

Pro Pro  Pro Lys Lys Ala Pro  Thr Pro Pro Pro Arg  Arg Arg Arg
    2315                 2320                 2325

Thr Val  Gly Leu Ser Glu Ser  Thr Ile Ser Glu Ala  Leu Gln Gln
    2330                 2335                 2340

Leu Ala  Ile Lys Thr Phe Gly  Gln Pro Pro Ser Ser  Gly Asp Ala
    2345                 2350                 2355

Gly Ser  Ser Thr Gly Ala Gly  Ala Ala Glu Ser Gly  Gly Pro Thr
    2360                 2365                 2370

Ser Pro  Gly Glu Pro Ala Pro  Ser Glu Thr Gly Ser  Ala Ser Ser
    2375                 2380                 2385

Met Pro  Pro Leu Glu Gly Glu  Pro Gly Asp Pro Asp  Leu Glu Ser
    2390                 2395                 2400

Asp Gln  Val Glu Leu Gln Pro  Pro Pro Gln Gly Gly  Gly Val Ala
    2405                 2410                 2415

Pro Gly  Ser Gly Ser Gly Ser  Trp Ser Thr Cys Ser  Glu Glu Asp
    2420                 2425                 2430

Asp Thr  Thr Val Cys Cys Ser  Met Ser Tyr Ser Trp  Thr Gly Ala
    2435                 2440                 2445

Leu Ile  Thr Pro Cys Ser Pro  Glu Glu Glu Lys Leu  Pro Ile Asn
    2450                 2455                 2460

Pro Leu  Ser Asn Ser Leu Leu  Arg Tyr His Asn Lys  Val Tyr Cys
    2465                 2470                 2475

Thr Thr  Ser Lys Ser Ala Ser  Gln Arg Ala Lys Lys  Val Thr Phe
    2480                 2485                 2490

Asp Arg  Thr Gln Val Leu Asp  Ala His Tyr Asp Ser  Val Leu Lys
    2495                 2500                 2505

Asp Ile  Lys Leu Ala Ala Ser  Lys Val Ser Ala Arg  Leu Leu Thr
    2510                 2515                 2520

Leu Glu  Glu Ala Cys Gln Leu  Thr Pro Pro His Ser  Ala Arg Ser
    2525                 2530                 2535

Lys Tyr  Gly Phe Gly Ala Lys  Glu Val Arg Ser Leu  Ser Gly Arg
    2540                 2545                 2550

Ala Val  Asn His Ile Lys Ser  Val Trp Lys Asp Leu  Leu Glu Asp
    2555                 2560                 2565

Pro Gln  Thr Pro Ile Pro Thr  Thr Ile Met Ala Lys  Asn Glu Val
    2570                 2575                 2580

Phe Cys  Val Asp Pro Ala Lys  Gly Gly Lys Lys Pro  Ala Arg Leu
    2585                 2590                 2595

Ile Val  Tyr Pro Asp Leu Gly  Val Arg Val Cys Glu  Lys Met Ala
    2600                 2605                 2610

Leu Tyr  Asp Ile Thr Gln Lys  Leu Pro Gln Ala Val  Met Gly Ala
    2615                 2620                 2625

Ser Tyr  Gly Phe Gln Tyr Ser  Pro Ala Gln Arg Val  Glu Tyr Leu
    2630                 2635                 2640

Leu Lys  Ala Trp Ala Glu Lys  Lys Asp Pro Met Gly  Phe Ser Tyr
    2645                 2650                 2655

Asp Thr  Arg Cys Phe Asp Ser  Thr Val Thr Glu Arg  Asp Ile Arg
    2660                 2665                 2670

Thr Glu  Glu Ser Ile Tyr Gln  Ala Cys Ser Leu Pro  Glu Glu Ala
    2675                 2680                 2685

Arg Thr  Ala Ile His Ser Leu  Thr Glu Arg Leu Tyr  Val Gly Gly
```

```
    2690                2695                2700

Pro Met  Phe Asn Ser Lys Gly  Gln Thr Cys Gly Tyr  Arg Arg Cys
    2705                2710                2715

Arg Ala  Ser Gly Val Leu Thr  Thr Ser Met Gly Asn  Thr Ile Thr
    2720                2725                2730

Cys Tyr  Val Lys Ala Leu Ala  Ala Cys Lys Ala Ala  Gly Ile Val
    2735                2740                2745

Ala Pro  Thr Met Leu Val Cys  Gly Asp Asp Leu Val  Val Ile Ser
    2750                2755                2760

Glu Ser  Gln Gly Thr Glu Glu  Asp Glu Arg Asn Leu  Arg Ala Phe
    2765                2770                2775

Thr Glu  Ala Met Thr Arg Tyr  Ser Ala Pro Pro Gly  Asp Pro Pro
    2780                2785                2790

Arg Pro  Glu Tyr Asp Leu Glu  Leu Ile Thr Ser Cys  Ser Ser Asn
    2795                2800                2805

Val Ser  Val Ala Leu Gly Pro  Arg Gly Arg Arg Arg  Tyr Tyr Leu
    2810                2815                2820

Thr Arg  Asp Pro Thr Thr Pro  Leu Ala Arg Ala Ala  Trp Glu Thr
    2825                2830                2835

Val Arg  His Ser Pro Ile Asn  Ser Trp Leu Gly Asn  Ile Ile Gln
    2840                2845                2850

Tyr Ala  Pro Thr Ile Trp Val  Arg Met Val Leu Met  Thr His Phe
    2855                2860                2865

Phe Ser  Ile Leu Met Val Gln  Asp Thr Leu Asp Gln  Asn Leu Asn
    2870                2875                2880

Phe Glu  Met Tyr Gly Ser Val  Tyr Ser Val Asn Pro  Leu Asp Leu
    2885                2890                2895

Pro Ala  Ile Ile Glu Arg Leu  His Gly Leu Asp Ala  Phe Ser Met
    2900                2905                2910

His Thr  Tyr Ser His His Glu  Leu Thr Arg Val Ala  Ser Ala Leu
    2915                2920                2925

Arg Lys  Leu Gly Ala Pro Pro  Leu Arg Val Trp Lys  Ser Arg Ala
    2930                2935                2940

Arg Ala  Val Arg Ala Ser Leu  Ile Ser Arg Gly Gly  Lys Ala Ala
    2945                2950                2955

Val Cys  Gly Arg Tyr Leu Phe  Asn Trp Ala Val Lys  Thr Lys Leu
    2960                2965                2970

Lys Leu  Thr Pro Leu Pro Glu  Ala Arg Leu Leu Asp  Leu Ser Ser
    2975                2980                2985

Trp Phe  Thr Val Gly Ala Gly  Gly Gly Asp Ile Phe  His Ser Val
    2990                2995                3000

Ser Arg  Ala Arg Pro Arg Ser  Leu Leu Phe Gly Leu  Leu Leu Leu
    3005                3010                3015

Phe Val  Gly Val Gly Leu Phe  Leu Leu Pro Ala Arg
    3020                3025                3030
```

<210> SEQ ID NO 7
<211> LENGTH: 3030
<212> TYPE: PRT
<213> ORGANISM: Artificial
<220> FEATURE:
<223> OTHER INFORMATION: TH/JFH-1(PT)

<400> SEQUENCE: 7

```
Met Ser Thr Asn Pro Lys Pro Gln Arg Lys Thr Lys Arg Asn Thr Asn
1               5                   10                  15
```

```
Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Val Tyr His Val Thr Asn Asp Cys Ser
        195                 200                 205

Asn Ser Ser Ile Val Tyr Glu Thr Gly Asp Met Ile Met His Thr Pro
    210                 215                 220

Gly Cys Val Pro Cys Val Arg Glu Asn Asn Ser Ser Arg Cys Trp Ala
225                 230                 235                 240

Ala Leu Thr Pro Thr Leu Ala Ala Arg Asn Ala Ser Val Pro Thr Thr
                245                 250                 255

Thr Ile Arg Arg His Val Asp Leu Leu Val Gly Ala Ala Ala Phe Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg His Glu Thr Val Gln Asp Cys
    290                 295                 300

Asn Cys Ser Ile Tyr Pro Gly His Val Ser Gly His Arg Met Ala Trp
305                 310                 315                 320

Asp Met Met Met Asn Trp Ser Thr Thr Thr Ala Leu Leu Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Ala Gly Asn Trp
        355                 360                 365

Ala Lys Val Leu Ile Val Leu Leu Leu Phe Ala Gly Val Asp Gly Ala
    370                 375                 380

Thr Tyr Val Thr Gly Gly Ser Glu Ala Arg Gly Ala Ser Gly Leu Ala
385                 390                 395                 400

Asn Leu Phe Ser Phe Gly Ala Ser Gln Lys Ile Gln Leu Ile Asn Thr
                405                 410                 415

Asn Gly Ser Trp His Ile Asn Arg Thr Ala Leu Asn Cys Asn Asp Ser
            420                 425                 430

Leu His Thr Gly Phe Leu Ala Ala Leu Phe Tyr Thr His Lys Phe Asn
```

```
        435                 440                 445

Ala Ser Gly Cys Pro Glu Arg Met Ala Ser Cys Arg Pro Ile Glu Glu
    450                 455                 460

Phe Ala Gln Gly Tyr Gly Pro Ile Thr Tyr Ala Glu Pro Ser Pro Ser
465                 470                 475                 480

Asp Gln Arg Pro Tyr Cys Trp His Tyr Ala Pro Arg Pro Cys Gly Ile
                485                 490                 495

Ile Pro Ala Ser Gln Val Cys Gly Pro Val Tyr Cys Phe Thr Pro Ser
            500                 505                 510

Pro Val Val Val Gly Thr Thr Asp Arg Ser Gly Ala Pro Thr Tyr Asn
        515                 520                 525

Trp Gly Ala Asn Glu Thr Asp Val Leu Tyr Leu Asn Asn Thr Arg Pro
    530                 535                 540

Pro Gln Gly Asn Trp Phe Gly Cys Thr Trp Met Asn Gly Thr Gly Phe
545                 550                 555                 560

Thr Lys Thr Cys Gly Gly Pro Pro Cys Asn Ile Gly Gly Gly Gly Asn
                565                 570                 575

Asn Asn Thr Leu Thr Cys Pro Thr Asp Cys Phe Arg Lys His Pro Glu
            580                 585                 590

Ala Thr Tyr Thr Lys Cys Gly Ser Gly Pro Trp Leu Thr Pro Arg Cys
        595                 600                 605

Met Val Asp Tyr Pro Tyr Arg Leu Trp His Tyr Pro Cys Thr Val Asn
    610                 615                 620

Phe Thr Ile Phe Lys Val Arg Met Tyr Val Gly Gly Val Glu His Arg
625                 630                 635                 640

Leu Asn Ala Ala Cys Asn Trp Thr Arg Gly Glu Arg Cys Asn Leu Glu
                645                 650                 655

Asp Arg Asp Arg Ser Glu Leu Ser Pro Leu Leu Leu Ser Thr Thr Glu
            660                 665                 670

Trp Gln Val Leu Pro Cys Ser Phe Thr Thr Leu Pro Ala Leu Ser Thr
        675                 680                 685

Gly Leu Ile His Leu His Gln Asn Ile Val Asp Val Gln Tyr Leu Tyr
    690                 695                 700

Gly Ile Gly Ser Ala Val Val Ser Tyr Ala Ile Lys Trp Glu Tyr Val
705                 710                 715                 720

Leu Leu Leu Phe Leu Leu Leu Ala Asp Ala Arg Val Cys Ala Cys Leu
                725                 730                 735

Trp Met Met Leu Leu Ile Ala Gln Ala Glu Ala Ala Leu Glu Asn Leu
            740                 745                 750

Val Val Leu Asn Ala Ala Ser Leu Ala Gly Ala His Gly Leu Leu Ser
        755                 760                 765

Phe Leu Val Phe Phe Cys Ala Ala Trp Tyr Ile Lys Gly Arg Leu Ile
    770                 775                 780

Pro Gly Ala Ala Tyr Ala Phe Tyr Gly Val Trp Pro Leu Leu Leu Leu
785                 790                 795                 800

Leu Leu Ala Leu Pro Pro Arg Ala Tyr Ala Met Asp Arg Glu Met Ala
                805                 810                 815

Ala Ser Cys Gly Gly Ala Val Phe Val Gly Leu Ala Phe Leu Thr Leu
            820                 825                 830

Ser Pro His Tyr Lys Ala Phe Leu Ala Lys Leu Leu Trp Trp Leu Cys
        835                 840                 845

Tyr Leu Leu Thr Leu Gly Glu Ala Met Ile Gln Glu Trp Val Pro Pro
    850                 855                 860
```

-continued

```
Met Gln Val Arg Gly Gly Arg Asp Gly Ile Ala Trp Ala Val Thr Ile
865                 870                 875                 880

Phe Cys Pro Gly Val Val Phe Asp Ile Thr Lys Trp Leu Leu Ala Leu
                885                 890                 895

Leu Gly Pro Ala Tyr Leu Leu Arg Ala Ala Leu Thr His Val Pro Tyr
            900                 905                 910

Phe Val Arg Ala His Ala Leu Ile Arg Val Cys Ala Leu Val Lys Gln
        915                 920                 925

Leu Ala Gly Gly Arg Tyr Val Gln Val Ala Leu Leu Ala Leu Gly Arg
    930                 935                 940

Trp Thr Gly Thr Tyr Ile Tyr Asp His Leu Thr Pro Met Ser Asp Trp
945                 950                 955                 960

Ala Ala Ser Gly Leu Arg Asp Leu Ala Val Ala Val Glu Pro Ile Ile
                965                 970                 975

Phe Ser Pro Met Glu Lys Lys Val Ile Val Trp Gly Ala Glu Thr Ala
            980                 985                 990

Ala Cys Gly Asp Ile Leu His Gly  Leu Pro Val Ser Ala  Arg Leu Gly
        995                 1000                1005

Gln Glu  Ile Leu Leu Gly Pro  Ala Asp Gly Tyr Thr  Ser Lys Gly
    1010                 1015                 1020

Trp Lys  Leu Leu Ala Pro Ile  Thr Ala Tyr Ala Gln  Gln Thr Arg
    1025                 1030                 1035

Gly Leu  Leu Gly Ala Ile Val  Val Ser Met Thr Gly  Arg Asp Arg
    1040                 1045                 1050

Thr Glu  Gln Ala Gly Glu Val  Gln Ile Leu Ser Thr  Val Ser Gln
    1055                 1060                 1065

Ser Phe  Leu Gly Thr Thr Ile  Ser Gly Val Leu Trp  Thr Val Tyr
    1070                 1075                 1080

His Gly  Ala Gly Asn Lys Thr  Leu Ala Gly Leu Arg  Gly Pro Val
    1085                 1090                 1095

Thr Gln  Met Tyr Ser Ser Ala  Glu Gly Asp Leu Val  Gly Trp Pro
    1100                 1105                 1110

Ser Pro  Pro Gly Thr Lys Ser  Leu Glu Pro Cys Lys  Cys Gly Ala
    1115                 1120                 1125

Val Asp  Leu Tyr Leu Val Thr  Arg Asn Ala Asp Val  Ile Pro Ala
    1130                 1135                 1140

Arg Arg  Arg Gly Asp Lys Arg  Gly Ala Leu Leu Ser  Pro Arg Pro
    1145                 1150                 1155

Ile Ser  Thr Leu Lys Gly Ser  Ser Gly Gly Pro Val  Leu Cys Pro
    1160                 1165                 1170

Arg Gly  His Val Val Gly Leu  Phe Arg Ala Ala Val  Cys Ser Arg
    1175                 1180                 1185

Gly Val  Ala Lys Ser Ile Asp  Phe Ile Pro Val Glu  Thr Leu Asp
    1190                 1195                 1200

Val Val  Thr Arg Ser Pro Thr  Phe Ser Asp Asn Ser  Thr Pro Pro
    1205                 1210                 1215

Ala Val  Pro Gln Thr Tyr Gln  Val Gly Tyr Leu His  Ala Pro Thr
    1220                 1225                 1230

Gly Ser  Gly Lys Ser Thr Lys  Val Pro Val Ala Tyr  Ala Ala Gln
    1235                 1240                 1245

Gly Tyr  Lys Val Leu Val Leu  Asn Pro Ser Val Ala  Ala Thr Leu
    1250                 1255                 1260

Gly Phe  Gly Ala Tyr Leu Ser  Lys Ala His Gly Ile  Asn Pro Asn
    1265                 1270                 1275
```

```
Ile Arg  Thr Gly Val Arg Thr  Val Met Thr Gly Glu  Ala Ile Thr
    1280                 1285                 1290

Tyr Ser  Thr Tyr Gly Lys Phe  Leu Ala Asp Gly Gly  Cys Ala Ser
    1295                 1300                 1305

Gly Ala  Tyr Asp Ile Ile Ile  Cys Asp Glu Cys His  Ala Val Asp
    1310                 1315                 1320

Ala Thr  Ser Ile Leu Gly Ile  Gly Thr Val Leu Asp  Gln Ala Glu
    1325                 1330                 1335

Thr Ala  Gly Val Arg Leu Thr  Val Leu Ala Thr Ala  Thr Pro Pro
    1340                 1345                 1350

Gly Ser  Val Thr Thr Pro His  Pro Asp Ile Glu Glu  Val Gly Leu
    1355                 1360                 1365

Gly Arg  Glu Gly Glu Ile Pro  Phe Tyr Gly Arg Ala  Ile Pro Leu
    1370                 1375                 1380

Ser Cys  Ile Lys Gly Gly Arg  His Leu Ile Phe Cys  His Ser Lys
    1385                 1390                 1395

Lys Lys  Cys Asp Glu Leu Ala  Ala Ala Leu Arg Gly  Met Gly Leu
    1400                 1405                 1410

Asn Ala  Val Ala Tyr Tyr Arg  Gly Leu Asp Val Ser  Ile Ile Pro
    1415                 1420                 1425

Ala Gln  Gly Asp Val Val Val  Val Ala Thr Asp Ala  Leu Met Thr
    1430                 1435                 1440

Gly Tyr  Thr Gly Asp Phe Asp  Ser Val Ile Asp Cys  Asn Val Ala
    1445                 1450                 1455

Val Thr  Gln Ala Val Asp Phe  Ser Leu Asp Pro Thr  Phe Thr Ile
    1460                 1465                 1470

Thr Thr  Gln Thr Val Pro Gln  Asp Ala Val Ser Arg  Ser Gln Arg
    1475                 1480                 1485

Arg Gly  Arg Thr Gly Arg Gly  Arg Gln Gly Thr Tyr  Arg Tyr Val
    1490                 1495                 1500

Ser Thr  Gly Glu Arg Ala Ser  Gly Met Phe Asp Ser  Val Val Leu
    1505                 1510                 1515

Cys Glu  Cys Tyr Asp Ala Gly  Ala Ala Trp Tyr Asp  Leu Thr Pro
    1520                 1525                 1530

Ala Glu  Thr Thr Val Arg Leu  Arg Ala Tyr Phe Asn  Thr Pro Gly
    1535                 1540                 1545

Leu Pro  Val Cys Gln Asp His  Leu Glu Phe Trp Glu  Ala Val Phe
    1550                 1555                 1560

Thr Gly  Leu Thr His Ile Asp  Ala His Phe Leu Ser  Gln Thr Lys
    1565                 1570                 1575

Gln Ala  Gly Glu Asn Phe Ala  Tyr Leu Val Ala Tyr  Gln Ala Thr
    1580                 1585                 1590

Val Cys  Ala Arg Ala Lys Ala  Pro Pro Pro Ser Trp  Asp Ala Met
    1595                 1600                 1605

Trp Lys  Cys Leu Ala Arg Leu  Lys Pro Thr Leu Ala  Gly Pro Thr
    1610                 1615                 1620

Pro Leu  Leu Tyr Arg Leu Gly  Pro Ile Thr Asn Glu  Val Thr Leu
    1625                 1630                 1635

Thr His  Pro Gly Thr Lys Tyr  Ile Ala Thr Cys Met  Gln Ala Asp
    1640                 1645                 1650

Leu Glu  Val Met Thr Ser Thr  Trp Val Leu Ala Gly  Gly Val Leu
    1655                 1660                 1665

Ala Ala  Val Ala Ala Tyr Cys  Leu Ala Thr Gly Cys  Val Ser Ile
```

-continued

```
    1670                1675                1680

Ile Gly  Arg Leu His Val Asn  Gln Arg Val Val Val  Ala Pro Asp
    1685                1690                1695

Lys Glu  Val Leu Tyr Glu Ala  Phe Asp Glu Met Glu  Glu Cys Ala
    1700                1705                1710

Ser Arg  Ala Ala Leu Ile Glu  Glu Gly Gln Arg Ile  Ala Glu Met
    1715                1720                1725

Leu Lys  Ser Lys Ile Gln Gly  Leu Leu Gln Gln Ala  Ser Lys Gln
    1730                1735                1740

Ala Gln  Asp Ile Gln Pro Ala  Met Gln Ala Ser Trp  Pro Lys Val
    1745                1750                1755

Glu Gln  Phe Trp Ala Arg His  Met Trp Asn Phe Ile  Ser Gly Ile
    1760                1765                1770

Gln Tyr  Leu Ala Gly Leu Ser  Thr Leu Pro Gly Asn  Pro Ala Val
    1775                1780                1785

Ala Ser  Met Met Ala Phe Ser  Ala Ala Leu Thr Ser  Pro Leu Ser
    1790                1795                1800

Thr Ser  Thr Thr Ile Leu Leu  Asn Ile Met Gly Gly  Trp Leu Ala
    1805                1810                1815

Ser Gln  Ile Ala Pro Pro Ala  Gly Ala Thr Gly Phe  Val Val Ser
    1820                1825                1830

Gly Leu  Val Gly Ala Ala Val  Gly Ser Ile Gly Leu  Gly Lys Val
    1835                1840                1845

Leu Val  Asp Ile Leu Ala Gly  Tyr Gly Ala Gly Ile  Ser Gly Ala
    1850                1855                1860

Leu Val  Ala Phe Lys Ile Met  Ser Gly Glu Lys Pro  Ser Met Glu
    1865                1870                1875

Asp Val  Ile Asn Leu Leu Pro  Gly Ile Leu Ser Pro  Gly Ala Leu
    1880                1885                1890

Val Val  Gly Val Ile Cys Ala  Ala Ile Leu Arg Arg  His Val Gly
    1895                1900                1905

Pro Gly  Glu Gly Ala Val Gln  Trp Met Asn Arg Leu  Ile Ala Phe
    1910                1915                1920

Ala Ser  Arg Gly Asn His Val  Ala Pro Thr His Tyr  Val Thr Glu
    1925                1930                1935

Ser Asp  Ala Ser Gln Arg Val  Thr Gln Leu Leu Gly  Ser Leu Thr
    1940                1945                1950

Ile Thr  Ser Leu Leu Arg Arg  Leu His Asn Trp Ile  Thr Glu Asp
    1955                1960                1965

Cys Pro  Ile Pro Cys Ser Gly  Ser Trp Leu Arg Asp  Val Trp Asp
    1970                1975                1980

Trp Val  Cys Thr Ile Leu Thr  Asp Phe Lys Asn Trp  Leu Thr Ser
    1985                1990                1995

Lys Leu  Phe Pro Lys Leu Pro  Gly Leu Pro Phe Ile  Ser Cys Gln
    2000                2005                2010

Lys Gly  Tyr Lys Gly Val Trp  Ala Gly Thr Gly Ile  Met Thr Thr
    2015                2020                2025

Arg Cys  Pro Cys Gly Ala Asn  Ile Ser Gly Asn Val  Arg Leu Gly
    2030                2035                2040

Ser Met  Arg Ile Thr Gly Pro  Lys Thr Cys Met Asn  Thr Trp Gln
    2045                2050                2055

Gly Thr  Phe Pro Ile Asn Cys  Tyr Thr Glu Gly Gln  Cys Ala Pro
    2060                2065                2070
```

```
Lys Pro  Pro Thr Asn Tyr Lys  Thr Ala Ile Trp Arg  Val Ala Ala
    2075                 2080                 2085

Ser Glu  Tyr Ala Glu Val Thr  Gln His Gly Ser Tyr  Ser Tyr Val
    2090                 2095                 2100

Thr Gly  Leu Thr Thr Asp Asn  Leu Lys Ile Pro Cys  Gln Leu Pro
    2105                 2110                 2115

Ser Pro  Glu Phe Phe Ser Trp  Val Asp Gly Val Gln  Ile His Arg
    2120                 2125                 2130

Phe Ala  Pro Thr Pro Lys Pro  Phe Phe Arg Asp Glu  Val Ser Phe
    2135                 2140                 2145

Cys Val  Gly Leu Asn Ser Tyr  Ala Val Gly Ser Gln  Leu Pro Cys
    2150                 2155                 2160

Glu Pro  Glu Pro Asp Ala Asp  Val Leu Arg Ser Met  Leu Thr Asp
    2165                 2170                 2175

Pro Pro  His Ile Thr Ala Glu  Thr Ala Ala Arg Arg  Leu Ala Arg
    2180                 2185                 2190

Gly Ser  Pro Pro Ser Glu Ala  Ser Ser Ser Val Ser  Gln Leu Ser
    2195                 2200                 2205

Ala Pro  Ser Leu Arg Ala Thr  Cys Thr Thr His Ser  Asn Thr Tyr
    2210                 2215                 2220

Asp Val  Asp Met Val Asp Ala  Asn Leu Leu Met Glu  Gly Gly Val
    2225                 2230                 2235

Ala Gln  Thr Glu Pro Glu Ser  Arg Val Pro Val Leu  Asp Phe Leu
    2240                 2245                 2250

Glu Pro  Met Ala Glu Glu Glu  Ser Asp Leu Glu Pro  Ser Ile Pro
    2255                 2260                 2265

Ser Glu  Cys Met Leu Pro Arg  Ser Gly Phe Pro Arg  Ala Leu Pro
    2270                 2275                 2280

Ala Trp  Ala Arg Pro Asp Tyr  Asn Pro Pro Leu Val  Glu Ser Trp
    2285                 2290                 2295

Arg Arg  Pro Asp Tyr Gln Pro  Pro Thr Val Ala Gly  Cys Ala Leu
    2300                 2305                 2310

Pro Pro  Pro Lys Lys Ala Pro  Thr Pro Pro Pro Arg  Arg Arg Arg
    2315                 2320                 2325

Thr Val  Gly Leu Ser Glu Ser  Thr Ile Ser Glu Ala  Leu Gln Gln
    2330                 2335                 2340

Leu Ala  Ile Lys Thr Phe Gly  Gln Pro Pro Ser Ser  Gly Asp Ala
    2345                 2350                 2355

Gly Ser  Ser Thr Gly Ala Gly  Ala Ala Glu Ser Gly  Gly Pro Thr
    2360                 2365                 2370

Ser Pro  Gly Glu Pro Ala Pro  Ser Glu Thr Gly Ser  Ala Ser Ser
    2375                 2380                 2385

Met Pro  Pro Leu Glu Gly Glu  Pro Gly Asp Pro Asp  Leu Glu Ser
    2390                 2395                 2400

Asp Gln  Val Glu Leu Gln Pro  Pro Pro Gln Gly Gly  Gly Val Ala
    2405                 2410                 2415

Pro Gly  Ser Gly Ser Gly Ser  Trp Ser Thr Cys Ser  Glu Glu Asp
    2420                 2425                 2430

Asp Thr  Thr Val Cys Cys Ser  Met Ser Tyr Ser Trp  Thr Gly Ala
    2435                 2440                 2445

Leu Ile  Thr Pro Cys Ser Pro  Glu Glu Glu Lys Leu  Pro Ile Asn
    2450                 2455                 2460

Pro Leu  Ser Asn Ser Leu Leu  Arg Tyr His Asn Lys  Val Tyr Cys
    2465                 2470                 2475
```

Thr Thr Ser Lys Ser Ala Ser Gln Arg Ala Lys Lys Val Thr Phe
2480 2485 2490

Asp Arg Thr Gln Val Leu Asp Ala His Tyr Asp Ser Val Leu Lys
2495 2500 2505

Asp Ile Lys Leu Ala Ala Ser Lys Val Ser Ala Arg Leu Leu Thr
2510 2515 2520

Leu Glu Glu Ala Cys Gln Leu Thr Pro Pro His Ser Ala Arg Ser
2525 2530 2535

Lys Tyr Gly Phe Gly Ala Lys Glu Val Arg Ser Leu Ser Gly Arg
2540 2545 2550

Ala Val Asn His Ile Lys Ser Val Trp Lys Asp Leu Leu Glu Asp
2555 2560 2565

Pro Gln Thr Pro Ile Pro Thr Thr Ile Met Ala Lys Asn Glu Val
2570 2575 2580

Phe Cys Val Asp Pro Ala Lys Gly Gly Lys Lys Pro Ala Arg Leu
2585 2590 2595

Ile Val Tyr Pro Asp Leu Gly Val Arg Val Cys Glu Lys Met Ala
2600 2605 2610

Leu Tyr Asp Ile Thr Gln Lys Leu Pro Gln Ala Val Met Gly Ala
2615 2620 2625

Ser Tyr Gly Phe Gln Tyr Ser Pro Ala Gln Arg Val Glu Tyr Leu
2630 2635 2640

Leu Lys Ala Trp Ala Glu Lys Lys Asp Pro Met Gly Phe Ser Tyr
2645 2650 2655

Asp Thr Arg Cys Phe Asp Ser Thr Val Thr Glu Arg Asp Ile Arg
2660 2665 2670

Thr Glu Glu Ser Ile Tyr Gln Ala Cys Ser Leu Pro Glu Glu Ala
2675 2680 2685

Arg Thr Ala Ile His Ser Leu Thr Glu Arg Leu Tyr Val Gly Gly
2690 2695 2700

Pro Met Phe Asn Ser Lys Gly Gln Thr Cys Gly Tyr Arg Arg Cys
2705 2710 2715

Arg Ala Ser Gly Val Leu Thr Thr Ser Met Gly Asn Thr Ile Thr
2720 2725 2730

Cys Tyr Val Lys Ala Leu Ala Ala Cys Lys Ala Ala Gly Ile Val
2735 2740 2745

Ala Pro Thr Met Leu Val Cys Gly Asp Asp Leu Val Val Ile Ser
2750 2755 2760

Glu Ser Gln Gly Thr Glu Glu Asp Glu Arg Asn Leu Arg Ala Phe
2765 2770 2775

Thr Glu Ala Met Thr Arg Tyr Ser Ala Pro Pro Gly Asp Pro Pro
2780 2785 2790

Arg Pro Glu Tyr Asp Leu Glu Leu Ile Thr Ser Cys Ser Ser Asn
2795 2800 2805

Val Ser Val Ala Leu Gly Pro Arg Gly Arg Arg Arg Tyr Tyr Leu
2810 2815 2820

Thr Arg Asp Pro Thr Thr Pro Leu Ala Arg Ala Ala Trp Glu Thr
2825 2830 2835

Val Arg His Ser Pro Ile Asn Ser Trp Leu Gly Asn Ile Ile Gln
2840 2845 2850

Tyr Ala Pro Thr Ile Trp Val Arg Met Val Leu Met Thr His Phe
2855 2860 2865

Phe Ser Ile Leu Met Val Gln Asp Thr Leu Asp Gln Asn Leu Asn

```
    2870                2875                2880

Phe Glu  Met Tyr Gly Ser Val  Tyr Ser Val Asn Pro  Leu Asp Leu
    2885                2890                2895

Pro Ala  Ile Ile Glu Arg Leu  His Gly Leu Asp Ala  Phe Ser Met
    2900                2905                2910

His Thr  Tyr Ser His His Glu  Leu Thr Arg Val Ala  Ser Ala Leu
    2915                2920                2925

Arg Lys  Leu Gly Ala Pro Pro  Leu Arg Val Trp Lys  Ser Arg Ala
    2930                2935                2940

Arg Ala  Val Arg Ala Ser Leu  Ile Ser Arg Gly Gly  Lys Ala Ala
    2945                2950                2955

Val Cys  Gly Arg Tyr Leu Phe  Asn Trp Ala Val Lys  Thr Lys Leu
    2960                2965                2970

Lys Leu  Thr Pro Leu Pro Glu  Ala Arg Leu Leu Asp  Leu Ser Ser
    2975                2980                2985

Trp Phe  Thr Val Gly Ala Gly  Gly Gly Asp Ile Phe  His Ser Val
    2990                2995                3000

Ser Arg  Ala Arg Pro Arg Ser  Leu Leu Phe Gly Leu  Leu Leu Leu
    3005                3010                3015

Phe Val  Gly Val Gly Leu Phe  Leu Leu Pro Ala Arg
    3020                3025                3030
```

<210> SEQ ID NO 8
<211> LENGTH: 18
<212> TYPE: DNA
<213> ORGANISM: Artificial
<220> FEATURE:
<223> OTHER INFORMATION: primer -21M13

<400> SEQUENCE: 8
tgtaaaacga cggccagt 18

<210> SEQ ID NO 9
<211> LENGTH: 40
<212> TYPE: DNA
<213> ORGANISM: Artificial
<220> FEATURE:
<223> OTHER INFORMATION: primer MS98

<400> SEQUENCE: 9
ggtttaggat tcgtgctcat ggtgcacggt ctacgagacc 40

<210> SEQ ID NO 10
<211> LENGTH: 40
<212> TYPE: DNA
<213> ORGANISM: Artificial
<220> FEATURE:
<223> OTHER INFORMATION: primer MS97

<400> SEQUENCE: 10
ggtctcgtag accgtgcacc atgagcacga atcctaaacc 40

<210> SEQ ID NO 11
<211> LENGTH: 40
<212> TYPE: DNA
<213> ORGANISM: Artificial
<220> FEATURE:
<223> OTHER INFORMATION: primer MS96

<400> SEQUENCE: 11
agatagcaca accaccacag gagcttggcg aggaatgcct 40

<210> SEQ ID NO 12
<211> LENGTH: 40
<212> TYPE: DNA
<213> ORGANISM: Artificial
<220> FEATURE:
<223> OTHER INFORMATION: primer MS99

<400> SEQUENCE: 12
agctgttcct cgctaggctc ctgtggtggt tgtgctatct 40

<210> SEQ ID NO 13
<211> LENGTH: 20
<212> TYPE: DNA
<213> ORGANISM: Artificial
<220> FEATURE:
<223> OTHER INFORMATION: primer MS89

<400> SEQUENCE: 13
cagctaccga ggggttaagc 20

<210> SEQ ID NO 14
<211> LENGTH: 24
<212> TYPE: DNA
<213> ORGANISM: Artificial
<220> FEATURE:
<223> OTHER INFORMATION: primer MS151

<400> SEQUENCE: 14
cccgggtacc cttggcccct ctat 24

<210> SEQ ID NO 15
<211> LENGTH: 30
<212> TYPE: DNA
<213> ORGANISM: Artificial
<220> FEATURE:
<223> OTHER INFORMATION: primer MS165

<400> SEQUENCE: 15
gtagggctgt tgtagctgac cagttcatca 30

<210> SEQ ID NO 16
<211> LENGTH: 30
<212> TYPE: DNA
<213> ORGANISM: Artificial
<220> FEATURE:
<223> OTHER INFORMATION: primer MS164

<400> SEQUENCE: 16
tgatgaactg gtcagctaca acagccctac 30

<210> SEQ ID NO 17
<211> LENGTH: 22
<212> TYPE: DNA
<213> ORGANISM: Artificial
<220> FEATURE:
<223> OTHER INFORMATION: primer MS156

<400> SEQUENCE: 17
tgggtggtac ccactcctga at 22

<210> SEQ ID NO 18
<211> LENGTH: 30
<212> TYPE: DNA
<213> ORGANISM: Artificial
<220> FEATURE:
<223> OTHER INFORMATION: primer MS163

-continued

<400> SEQUENCE: 18
gtagggctgt tgtagttgac cagttcatca 30

<210> SEQ ID NO 19
<211> LENGTH: 30
<212> TYPE: DNA
<213> ORGANISM: Artificial
<220> FEATURE:
<223> OTHER INFORMATION: primer MS162

<400> SEQUENCE: 19
tgatgaactg gtcaactaca acagccctac 30

NUCLEIC ACID COMPRISING CHIMERIC GENE DERIVED FROM HEPATITIS C VIRUS

TECHNICAL FIELD

The present invention relates to a nucleic acid comprising a chimeric gene derived from hepatitis C viruses, a chimeric hepatitis C virus particle of the JFH-1 strain and a strain other than the JFH-1 strain (preferably a strain of genotype 1a, 1b, or 2a), a vector used for producing the virus particle, and a cell that produces the virus particle.

The present invention also relates to a method for screening for an anti-HCV drug using the virus particle, a vaccine obtained by inactivating or attenuating the virus particle, and an anti-hepatitis C virus antibody that recognizes the virus particle as an antigen.

BACKGROUND ART

Hepatitis C virus (which may be simply referred to as "HCV" hereinafter) was discovered and identified as a causative virus of non-A and non-B hepatitis by Choo et al. in 1989 (Choo, Q L. et al., Science, 244: 359-362, 1989). HCV infection is a major cause for the progression with persistent infection from chronic hepatitis to cirrhosis and then hepatic cancer. It is said that there are approximately 170,000,000 HCV patients in the world and approximately 2,000,000 HCV patients in Japan. The major route of infection is transmission through blood. Since the screening of blood for transfusion was made available, the number of people newly infected with HCV dramatically decreased in Japan. However, it is considered that many virus carriers still remain.

At present, HCV is mainly treated with the use of PEG-interferon or with the use of PEG-interferon in combination with an antiviral drug (i.e., ribavirin). HCV is currently classified into 6 different genotypes, and HCV of genotype 1b and of genotype 2a are major types in Japan. In the case of HCV of genotype 1b, in particular, viruses cannot be completely eliminated from the body via administration of interferon and ribavirin, and therapeutic effects are insufficient. Accordingly, development of novel antiviral drugs or vaccines aimed at preventing virus carriers from causing the disease to develop or at eliminating viruses has been awaited.

The lack of effective animals that reflect virus infection besides chimpanzees and the lack of an effective in vitro virus culture system had been impediments to the development of therapeutic agents of HCV. In recent years, HCV replicon systems that enable evaluation of HCV-RNA replication have been developed (Lohmann, V. et al., Science., 285: 110-113, 1999), and such systems resulted in important progress as a system for screening for HCV inhibitors associated with the inhibition of virus replication.

HCV is a single-stranded (+) RNA virus having a genome length of approximately 9.6 kb, which has a gene encoding a precursor protein converted into 10 types of virus proteins (i.e., Core, E1, E2, p7, NS2, NS3, NS4A, NS4B, NS5A and NS5B proteins) upon post-translational cleavage by proteases. The replicon system was prepared by recombining the translation region of the HCV structural protein with a drug-resistant gene and inserting IRES of the encephalomyocarditis virus (EMCV) downstream thereof. RNA replication is observed in cells into which such recombinant RNA has been introduced. Even when a full-length genome RNA having the HCV structural protein region has been introduced into cells, however, release of virus particles into the culture solution has not been observed (Pietschmann, T. et al., J. Virol., 76: 4008-4021, 2002).

Recently, the HCV JFH-1 strain of genotype 2a isolated from a patient with fulminant hepatitis was discovered by Wakita et al., and the strain was found to be released as infectious virus particles in a culture medium of Huh-7 cells (hepatic cancer cell lines) (WO 05080575A1 and Wakita, T. et al., Nat. Med., 11: 791-796, 2005). This in vitro culture system for infectious HCV particles is expected to serve as a useful screening tool in the development of anti-HCV agents and to be an effective means for preparation of HCV vaccines. Research on HCV particle production in in vitro culture systems has made progress, and the HCV genome capable of virus particle production was found to be chimeric HCV of the JFH-1 strain and an HCV strain other than the JFH-1 strain. Such chimeric HCV can be prepared by recombining the structural genes of the JFH-1 genome (i.e., Core, E1, E2 and p7 protein coding sections) with structural genes of other HCV strains.

As chimeric HCV of the JFH-1 strain and an HCV strain other than the JFH-1 strain, the chimeric HCV of the J6CF strain (genotype 2a) and the JFH-1 strain (Lindenbach, B. D. et al., Science, 309: 623-626, 2005), the chimeric HCV of the H77 strain (genotype 1a) and the JFH-1 strain (WO 06096459A2 and MinKyung, Y. et al., J. Virol., 81: 629-638, 2007), and the chimeric HCV of the S52 strain (genotype 3a) and the JFH-1 strain (Gottwein, J M et al., Gastroenterology 133: 1614-1626, 2007) are known.

Pietschmann, T. et al. (Proc. Natl. Acad. Sci. U.S.A., 103: 7408-7413, 2006) discloses that the amount of viruses produced from chimeric HCV of the J6CF structural gene and the JFH-1 non-structural gene is the highest and the amount of infectious virus particles produced from chimeric HCV of the Con1 strain of genotype 1b and the JFH-1 strain is one tenth the former amount. As other chimeric HCV of a genotype 1b strain and the JFH-1 strain, WO 06022422A1 discloses that a genome (full-length genome replicon RNA) in which a region encoding the structural proteins of the TH strain is recombined with that of the JFH-1 genome, and a drug-resistant gene is inserted into a site upstream of such coding region was produced, the resulting genome is introduced into the Huh-7 cell, and then a drug-resistant strain is obtained, and infectious virus particles are produced into the culture supernatant, although productivity thereof is not clearly described.

Under such circumstances, concerning genotype 1b for which the possibility of attaining a complete remission with current therapy techniques is small and of which the number of patients is large, there is a need for development of a method for producing HCV particles that can produce large quantities of infectious virus particles with the structure of genotype 1b, and that can be cultured in a persistent infection system.

DISCLOSURE OF THE INVENTION

Problem to Be Solved by the Invention

It is an object of the present invention to provide a method for efficiently producing HCV particles having the structural protein(s) of an HCV strain other than the JFH-1 strain of genotype 1a, 1b, or 2a and vaccines and the like comprising the resulting HCV particles.

Means for Solving the Problem

The present inventors have conducted concentrated studies in order to solve the above problem. They examined the ability to produce HCV particles via cell culture and discovered an adaptive mutation that appears during HCV proliferation. They demonstrated that introduction of such adaptive mutation yields the significantly enhanced ability to produce HCV particles compared with wild-type strains before introduction of such mutation, and that HCV particles having the structural protein of the HCV strain of genotype 1a, 1b, or 2a can be prepared in a persistent infection system. This has led to the completion of the present invention.

Specifically, the present invention relates to (1) to (22) below.

(1) A nucleic acid comprising a chimeric gene derived from hepatitis C viruses comprising regions each encoding, Core protein, E1 protein, E2 protein and p7 protein derived from a hepatitis C virus strain other than JFH-1 strain; NS2 protein derived from JFH-1 strain or a hepatitis C virus strain other than JFH-1 strain, or a chimeric NS2 protein of NS2 protein derived from JFH-1 strain and NS2 protein derived from a hepatitis C virus strain other than JFH-1 strain; and NS3 protein, NS4A protein, NS4B protein, NS5A protein and NS5B protein derived from JFH-1 strain in that order in 5' to 3' direction, wherein the 328th proline residue from the amino acid residue at N-terminus of the Core protein is substituted with an amino acid residue other than proline.

(2) The nucleic acid according to (1) above, which comprises 5'-untranslated region of JFH-1 strain on the 5' side of the Core protein coding region and 3'-untranslated region of JFH-1 strain on the 3' side of the NS5B protein coding region.

(3) The nucleic acid according to (1) or (2) above, wherein the hepatitis C virus strain other than JFH-1 strain is of genotype 1a, 1b, or 2a.

(4) The nucleic acid according to any one of (1) to (3) above, wherein the hepatitis C virus strain other than JFH-1 strain is selected from the group consisting of TH strain, Con1 strain, J1 strain and derivative strains thereof.

(5) The nucleic acid according to any one of (1) to (4) above, wherein the amino acid residue other than proline is selected from the group consisting of Ala, Leu, Ile, Val, Thr and Ser.

(6) The nucleic acid according to any one of (1) to (5) above, wherein the nucleic acid is DNA comprising the nucleotide sequence as shown in SEQ ID NO: 1 of the sequence listing or a nucleotide sequence having 90% or more identity to the nucleotide sequence as shown in SEQ ID NO: 1, or RNA comprising the nucleotide sequence as shown in SEQ ID NO: 3 of the sequence listing or a nucleotide sequence having 90% or more identity to the nucleotide sequence as shown in SEQ ID NO: 3.

(7) The nucleic acid according to any one of (1) to (5) above, wherein the nucleic acid is DNA comprising the nucleotide sequence as shown in SEQ ID NO: 2 of the sequence listing or a nucleotide sequence having 90% or more identity to the nucleotide sequence as shown in SEQ ID NO: 2, or RNA comprising the nucleotide sequence as shown in SEQ ID NO: 4 of the sequence listing or a nucleotide sequence having 90% or more identity to the nucleotide sequence as shown in SEQ ID NO: 4.

(8) A vector comprising the nucleic acid according to any one of (1) to (7) above.

(9) A chimeric hepatitis C virus particle comprising the nucleic acid according to any one of (1) to (7) above as a virus genome.

(10) A cell which produces the chimeric hepatitis C virus particle according to (9) above.

(11) The cell according to (10) above, wherein the cell is of Huh-7 strain or a derivative strain thereof.

(12) A method for screening for an anti-hepatitis C virus substance comprising culturing, in the presence of a test substance:

(a) the cell according to (10) or (11) above; or (b) the chimeric hepatitis C virus particle according to (9) above and a hepatitis C virus-sensitive cell, and detecting replicon RNA or a virus particle derived from above-mentioned nucleic acid in the resulting culture.

(13) A hepatitis C virus vaccine comprising the chimeric hepatitis C virus particle according to (9) above.

(14) The hepatitis C virus vaccine according to (13) above, wherein the chimeric hepatitis C virus particle is inactivated or attenuated.

(15) An anti-hepatitis C virus antibody which recognizes the chimeric hepatitis C virus particle according to (9) above as an antigen.

(16) The nucleic acid according to (4) above, wherein the hepatitis C virus strain other than JFH-1 strain is TH strain or a derivative strain thereof.

(17) The nucleic acid according to (5) above, wherein the amino acid residue other than proline is Ala or Thr.

(18) A method for producing a chimeric hepatitis C virus particle comprising steps of:

culturing the cell according to (10) or (11) above; and recovering the chimeric hepatitis C virus particle according to (9) above.

(19) A method for producing a hepatitis C virus vaccine comprising steps of:

inactivating or attenuating the chimeric hepatitis C virus particle according to (9) above to prepare an inactivated or attenuated chimeric hepatitis C virus particle; and formulating the inactivated or attenuated chimeric hepatitis C virus particle into a hepatitis C virus vaccine.

(20) A method for producing an anti-hepatitis C virus antibody comprising a step of immunizing an animal (excluding a human) with the chimeric hepatitis C virus particle according to (9) above that is or is not inactivated or attenuated.

(21) The method according to (20) above, wherein the anti-hepatitis C virus antibody is a polyclonal or monoclonal antibody.

(22) The method according to (20) above, wherein the anti-hepatitis C virus antibody is a humanized antibody.

Effects of the Invention

The nucleic acid comprising a chimeric gene derived from hepatitis C viruses of the present invention can be used for producing chimeric HCV particles exhibiting significantly higher productivity than wild-type HCV particles. The chimeric HCV particles of the present invention are advantageous over wild-type HCV particles in terms of their significantly high ability to be produced and their high infectivity with cells. Thus, the utility value thereof is high for a vaccine for HCV prevention or treatment or as a tool used for inducing an antibody reacting with HCV.

This description includes the contents of the description and/or drawings of Japanese Patent Application No. 2008-116193, which is a priority document of the present application.

Figure 5A:
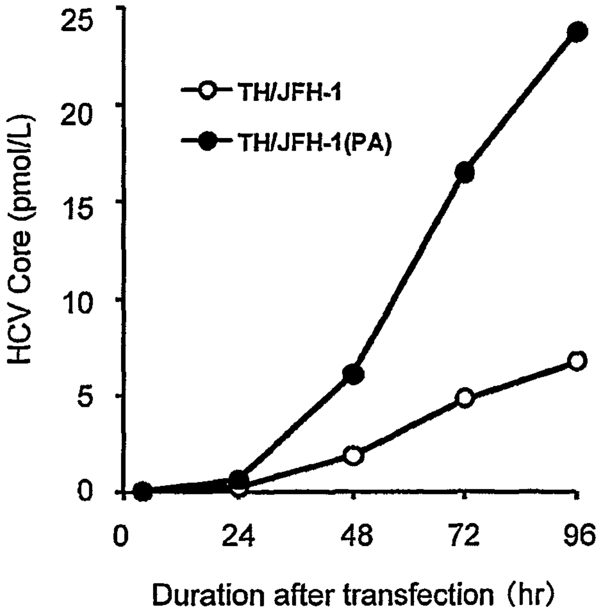
FIG. 5A shows changes in concentrations of the HCV Core protein in the culture supernatant until 96 hours had passed since RNAs synthesized from pTH/JFH1 and pTH/JFH1(PA) had been introduced into the Huh-7 cells. The amount of Core protein produced in the culture supernatant of TH/JFH-1(PA) became greater 48 hours after RNA introduction and later, than that of TH/JFH-1.
Figure 5B:
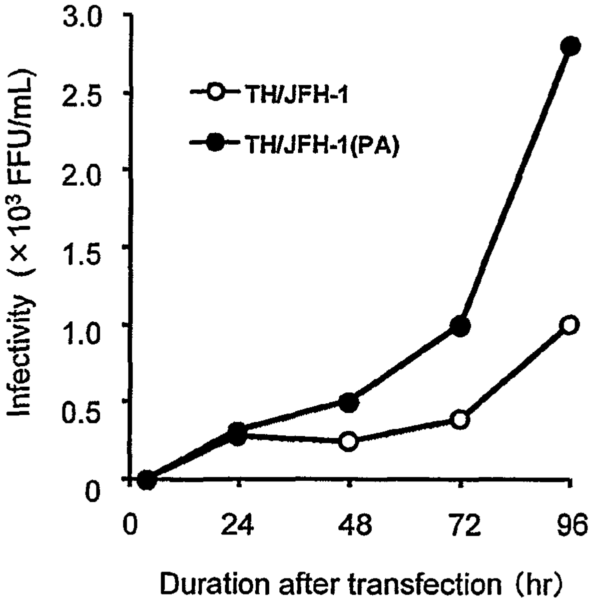
FIG. 5B shows the infectious titer attained when uninfected Huh-7 cells are inoculated with the culture supernatants obtained in FIG. 5A. The infectious titer in the culture supernatant of TH/JFH-1(PA) became greater 48 hours after RNA introduction and later, than that of TH/JFH-1.

The table shown in FIG. 6 shows the results of quantification of concentrations of HCV Core protein in the culture supernatants obtained by the experiments shown in FIG. 5, the infectious titers for the Huh-7 cells, and concentrations of HCV Core protein in the cells. The proportion of Core protein after 96 hours relative to that of Core proteins in the cells after 4 hours represents the degree of autonomous replication of RNAs of TH/JFH-1 and of TH/JFH-1(PA) in the cells. The efficiency of HCV Core secretion serves as an indicator of the efficiency of HCV particle secretion in the culture supernatant. Such efficiency was calculated by dividing the amount of Core protein in the culture supernatant after 96 hours by the sum of the amount of Core protein in the culture supernatant after 96 hours and the amount of Core protein in the cell after 96 hours. The efficiency of HCV particle secretion in the culture supernatant in the cells into which RNA of TH/JFH-1(PA) had been introduced was higher than that of TH/JFH-1.

BEST MODES FOR CARRYING OUT THE INVENTION

In general, the nucleic acid of the present invention comprises a chimeric gene of HCV comprising a nucleotide sequence encoding non-structural proteins of the JFH-1 strain and a nucleotide sequence encoding structural proteins of an HCV strain other than the JFH-1 strain. In addition, the nucleic acid of the present invention comprises a nucleotide sequence encoding the E1 protein having a given amino acid mutation.

Specifically, the nucleic acid of the present invention comprises:

(1) a chimeric gene derived from the hepatitis C viruses comprising regions each encoding the Core protein, the E1 protein, the E2 protein and the p7 protein derived from a hepatitis C virus strain other than the JFH-1 strain, the NS2 protein derived from the JFH-1 strain or a hepatitis C virus strain other than the JFH-1 strain, or the chimeric NS2 protein of the NS2 protein derived from the JFH-1 strain and the NS2 protein derived from a hepatitis C virus strain other than the JFH-1 strain, and the NS3 protein, the NS4A protein, the NS4B protein, the NS5A protein, and the NS5B protein derived from the JFH-1 strain in that order in the 5' to 3' direction; and (2) a nucleotide sequence encoding a combined protein (i.e., a precursor protein) in which the amino acid residue 328 when an amino acid residue at the N terminus of the Core protein; i.e., a methionine residue, is designated as amino acid residue 1 (or amino acid residue 137 when the amino acid residue at the N terminus of the E1 protein is designated as amino acid residue 1); i.e., the proline residue is substituted with an amino acid residue other than proline.

The NS2 protein of the nucleic acid of the present invention may be derived from the JFH-1 strain, it may be derived from an HCV strain other than the JFH-1 strain, and it may be a chimeric protein comprising part of the NS2 protein derived from an HCV strain other than the JFH-1 strain and remaining part of the NS2 protein derived from the JFH-1 strain. In such a case, such chimeric protein has functions similar to those of the wild-type NS2 protein. When part of the NS2 protein derived from an HCV strain other than the JFH-1 strain is composed of an amino acid sequence from the N-terminus to amino acid 33 of the NS2 protein, for example, the remaining part of the NS2 protein derived from the JFH-1 strain consists of an amino acid sequence from amino acid 34 to the C terminus.

Examples of the chimeric gene derived from hepatitis C viruses include DNA consisting of nucleotides 341 to 9433 of SEQ ID NO: 1 or 2 of the sequence listing and RNA consisting of nucleotides 341 to 9433 of SEQ ID NO: 3 or 4 of the sequence listing.

According to an embodiment of the present invention, the nucleic acid of the present invention can further comprise the 5'-untranslated region of the JFH-1 strain on the 5' side of the Core protein coding region and the 3'-untranslated region of the JFH-1 strain on the 3' side of the NS5B protein coding region.

According to an embodiment of the present invention, the HCV strain other than the JFH-1 strain is of genotype 1a, 1b, or 2a. Examples of strains of genotype 1b include the TH strain, the Con1 strain, the J1 strain and derivative strains thereof. An example of a strain of genotype 1a is the H77 strain. An example of a strain of genotype 2a is the J6CF strain. Examples of preferable strains are those of genotype 1b as exemplified above. The TH strain or a derivative strain thereof is more preferable. In the present invention, the 328th amino acid residue from the amino acid residue at the N terminus of the Core protein derived from the exemplified strain must be mutated into an amino acid residue other than proline.

According to another embodiment of the present invention, the amino acid residue other than proline is, for example, Ala, Leu, Ile, Val, Thr, or Ser, and it is preferably Ala or Thr.

According to an embodiment of the present invention, the nucleic acid is DNA comprising the nucleotide sequence as shown in SEQ ID NO: 1 or RNA comprising the nucleotide sequence as shown in SEQ ID NO: 3. According to another embodiment, the nucleic acid is DNA comprising the nucleotide sequence as shown in SEQ ID NO: 2 or RNA comprising the nucleotide sequence as shown in SEQ ID NO: 4. Such nucleic acids are chimeric nucleic acids derived from the JFH-1 strain and the TH strain. The nucleic acid as shown in SEQ ID NO: 1 or 3 has a nucleotide sequence identical to that of the nucleic acid as shown in SEQ ID NO: 2 or 4, except that the former sequence comprises a codon (nucleotides 1322 to 1324) encoding Ala as the 328th amino acid residue from the amino acid residue at the N terminus of the Core protein while the nucleic acid as shown in SEQ ID NO: 2 or 4 comprises a codon (nucleotides 1322 to 1324) encoding Thr as the 328th amino acid residue from the amino acid residue at the N terminus of the Core protein.

Further, the amino acid sequence encoded by the nucleotide sequence corresponding to ORF of DNA as shown in SEQ ID NO: 1 (i.e., the sequence from the N terminus of Core to the C terminus of NS5B) is shown in SEQ ID NO: 6. The amino acid sequence encoded by the nucleotide sequence corresponding to ORF of DNA as shown in SEQ ID NO: 2 (i.e., the sequence from the N terminus of Core to the C terminus of NS5B) is shown in SEQ ID NO: 7.

The nucleotide sequence of the present invention may comprise a nucleotide sequence having 90% or more, preferably 95% or more, and more preferably 98% to 99% or more identity to the nucleotide sequence as shown in SEQ ID NO: 1, 2, 3, or 4. In such a case, the 1,322nd to 1,324th residues from the 5' terminus of the nucleotide sequence as shown in SEQ ID NO: 1, 2, 3, or 4 encode amino acid residues other than proline (see above).

The amino acid sequence of the present invention may comprise an amino acid sequence having 90% or more, preferably 95% or more, and more preferably 98% to 99% or more identity to the amino acid sequence as shown in SEQ ID NO: 5 or 6. In such a case, the 328th residue from the amino acid residue at the N terminus of the Core protein encodes an amino acid residue other than proline (see above).

This is because, as several genotypes of HCV, which is an RNA virus, are known, the structural region, the non-structural region, and/or the (5'- or 3'-) untranslated region of HCV are likely to undergo mutation.

In the present invention, the term "the 328th amino acid residue from the amino acid residue at the N terminus of the Core protein" used above refers to an amino acid residue that is aligned at the same position as that of the 328th amino acid residue of the sequence as shown in SEQ ID NO: 5, 6, or 7 in the amino acid sequence comprising a region from the N terminus of HCV Core to the C terminus of NS5B that is aligned with the amino acid sequence as shown in SEQ ID NO: 5, 6, or 7 of the sequence listing (i.e., the sequence from the N terminus of Core to the C terminus of NS5B). Also, the condition in which "the 328th amino acid residue from the amino acid residue at the N terminus of the Core protein derived from the exemplified strain is substituted with an amino acid residue other than proline" is a condition in which an amino acid residue in a given amino acid sequence that is aligned at the same position as that of the 328th amino acid residue of the sequence as shown in SEQ ID NO: 5 is an amino acid residue other than proline.

The term "% identity" used with reference to two sequences herein refers to a function of the number of positions that two nucleotide or amino acid sequences share, and it refers to a percentage of the number of matched positions relative to the total number of positions when two sequences are aligned with or without the introduction of a gap. % identity can be determined with the use of mathematical algorithms, such as BLASTN, BLASTX, or Gapped BLAST (e.g., Karlin and Altschul, Proc. Natl. Acad. Sci. U.S.A., 90: 5873-5877, 1993; Altschul et al., Nucleic Acids Res., 25: 3389-3402, 1997).

The present invention provides a vector or a chimeric HCV particle comprising the above nucleic acid. Such chimeric HCV particle can be produced with higher efficiency in a cell culture system, compared with a wild-type particle, and it has higher infectivity. Advantages such as high-efficiency production or high infectivity result from mutation of the 328th amino acid residue from the amino acid residue at the N terminus of the Core protein with an amino acid residue other than Pro (preferably Ala or Thr), which are apparent from the results shown in FIGS. 4 and 5.

The nucleic acid, the vector, and the chimeric HCV particle of the present invention can be prepared via conventional molecular biological, virological, or other techniques within the scope of the technology of the relevant field. Such techniques are described in academic documents, patent documents, specialized books, and the like. Examples of such documents include Sambrook et al., Molecular Cloning: A Laboratory Manual (vol. 3, 2001, CSHL PRESS), Mahy et al., Virology: a practical approach (1985, IRL PRESS), Ausubel et al., Current Protocols in Molecular Biology (vol. 3, 1995, John Wiley & Sons), and U.S. Pat. No. 4,683,202 (Cetus Corporation; PCR).

Figure 1:
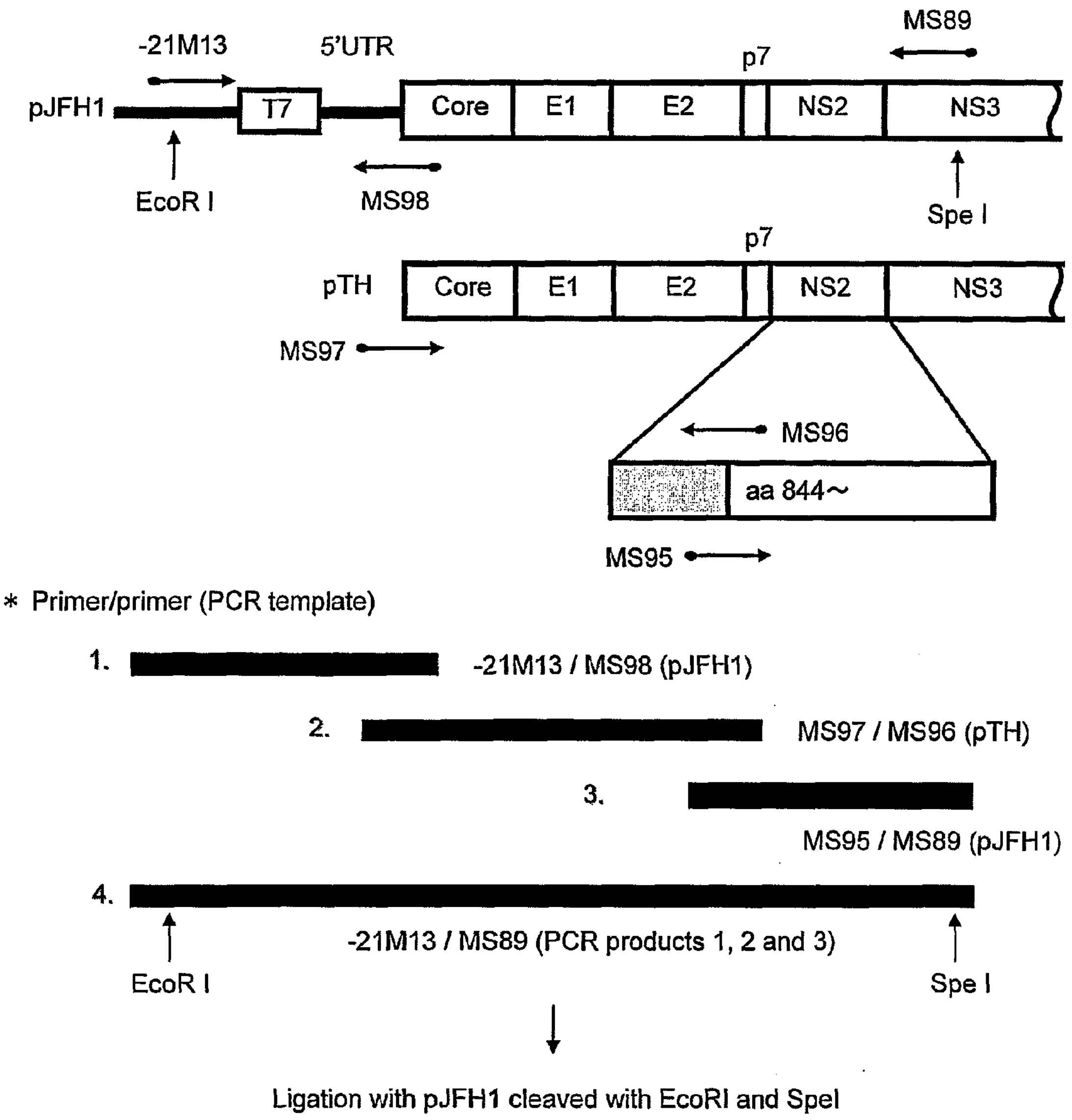
FIG. 1 shows a method for preparing the pTH/JFH1 plasmid. In the pJFH1 sequence, a nucleotide sequence encoding amino acid residues 1 to 846 of the amino acid sequence of the JFH-1 Core protein when the amino acid residue at the N-terminus of the JFH-1 is designated as amino acid residue 1 is substituted with a nucleotide sequence encoding amino acid residues 1 to 843 of the amino acid sequence of the Core protein of the TH strain when the amino acid residue at the N terminus of the TH strain is designated as amino acid 1.

In order to produce the nucleic acid or infectious HCV particles of the present invention, a polymerase chain reaction (PCR) is carried out with the use of a vector prepared via cloning of cDNA of genome RNA derived from the JFH-1 strain or an HCV strain other than the JFH-1 strain as a template and the forward and the reverse primers designed based on the sequence of the cDNA, so that the target sequence portion can be amplified. As shown in FIG. 1 or 3, specifically, a plurality of different PCR products having overlapping sequences are synthesized, such PCR products are mixed, the resultant is used as a template, and PCR is carried out using a forward primer comprising the 5' end of the target nucleic acid and a reverse primer comprising the 5' end of a complementary strand of such nucleic acid, so that the target nucleic acid can be amplified. The ends of the synthesized nucleic acids are cleaved with restriction enzymes and ligated to the pJFH1 plasmid that was cleaved with the same enzyme (Wakita, T. et al., Nat. Med., 11: 791-796, 2005; WO 2004/104198). The basic technique of such procedure is also described in, for example, WO 04104198 A1, WO 06022422 A1, Wakita, T. et al., Nat. Med., 11: 791-796, 2005, and Lindenbach, B. D. et al., Science, 309: 623-626, 2005.

PCR is carried out in the presence of a template, primers, dNTPs, heat-resistant polymerase, and $Mg^{2+}$-containing buffer, and a step of 94° C. to 98° C. for about 10 to 60 seconds, 55° C. to 58° C. for about 10 to 60 seconds, and 72° C. for about 30 to 60 seconds is repeated 20 to 40 times, although PCR conditions are not limited thereto.

In general, the HCV genome is RNA comprising the 5'-untranslated region, the Core protein coding region, the E1 protein coding region, the E2 protein coding region, the p7 protein coding region, the NS2 protein coding region, the NS3 protein coding region, the NS4A protein coding region, the NS4B protein coding region, the NS5A protein coding region, the NS5B protein coding region, and the 3'-untranslated region. In contrast, the nucleic acid of the present invention capable of producing infectious HCV particles is composed of virus genome RNA of two or more types of HCV strains or DNA encoding such RNA.

The nucleic acid of the present invention comprises, for example, the 5'-untranslated region, the region encoding part of the NS2 protein, the NS3 protein coding region, the NS4A protein coding region, the NS4B protein coding region, the NS5A protein coding region, the NS5B protein coding region, and the 3'-untranslated region, which are derived from the JFH-1 strain, and the Core protein coding region, the E1 protein coding region, the E2 protein coding region, the p7 protein coding region, and the region encoding remaining part of the NS2 protein, which are derived from an HCV strain other than the JFH-1 strain. The 5' untranslated region may be derived from an HCV strain other than the JFH-1 strain.

According to another embodiment of the present invention, the chimeric nucleic acid of the present invention comprises the 5'-untranslated region, the Core protein coding region, the E1 protein coding region, the E2 protein coding region, the p7 protein coding region and the NS2 protein coding region, which are derived from an HCV strain other than the JFH-1 strain and the NS3 protein coding region, the NS4A protein coding region, the NS4B protein coding region, the NS5A protein coding region, the NS5B protein coding region and the 3'-untranslated region, which are derived from the JFH-1 strain.

According to another embodiment of the present invention, the nucleic acid of the present invention comprises the 5'-untranslated region derived from the JFH-1 strain; the Core protein coding region, the E1 protein coding region, the E2 protein coding region, the p7 protein coding region and the region encoding part of the NS2 protein derived from the TH strain; and the region encoding another part of the NS2 protein, NS3 protein coding region, the NS4A protein coding region, the NS4B protein coding region, the NS5A protein coding region, the NS5B protein coding region, and the 3'-untranslated region derived from the JFH-1 strain. As long as the Core protein coding region, the E1 protein coding region, the E2 protein coding region, and the p7 protein coding region are derived from the TH strain, however, the chimeric nucleic acid is not limited thereto.

Hereafter, use of the vector, the infectious HCV particles, HCV particle-producing cells, and HCV particles of the present invention are described in greater detail.

(1) Vector Preparation

The hepatitis C virus (HCV) genome is a single-stranded (+) RNA comprising approximately 9,600 nucleotides. This genomic RNA comprises a 5'-untranslated region (also referred to as "5' NTR" or "5' UTR"), a translational region composed of structural regions and non-structural regions, and a 3'-untranslated region (also referred to as "3' NTR" or "3' UTR"). In the structural regions, HCV structural proteins are encoded and, in the non-structural regions, a plurality of non-structural proteins are encoded.

Such HCV structural proteins (Core, E1, E2 and p7) and non-structural proteins (NS2, NS3, NS4A, NS4B, NS5A and NS5B) are first translated as a continuous polyprotein (i.e., precursor protein) from the translational region, subjected to limited degradation by protease in infected cells, and released and produced. Among such structural and non-structural proteins (i.e., HCV virus proteins), Core is a core protein, and E1 and E2 are envelope proteins. It is known that non-structural proteins are associated with replication of the virus itself, NS2 has metalloprotease activity, and NS3 has serine protease activity (one-third of the N-terminal side) and helicase activity (two-thirds of the C-terminal side). Further, it is reported that NS4A is a cofactor for protease activity of NS3, and NS5B has RNA-dependent RNA polymerase activity.

HCV is coated with a coat referred to as an envelope. The envelope comprises a component derived from the membrane of a host cell and proteins derived from the virus. The proteins that constitute the HCV envelope comprise envelope protein 1 (referred to as "E1"), envelope protein 2 (referred to as "E2") and p7. In particular, E1 and E2 each have a transmembrane region at the C terminus, and E1 and E2 are anchored to the HCV membrane through such transmembrane region. Thus, the E1 and the E2 proteins of HCV are exposed to the outside, and HCV adheres to and infects cells via E1 and/or E2.

According to phylogenetic analysis using nucleotide sequences of the HCV strain, HCV is classified into 6 types (i.e., genotypes 1 to 6) and such genotypes are further classified into several subtypes. In addition, the nucleotide sequences of the full-length genomes of a plurality of HCV genotypes are determined (Simmonds, P. et al., Hepatology, 10: 1321-1324, 1994; Choo, Q. L. et al., Science, 244: 359-362, 1989; Okamoto, H. et al., J. Gen. Virol., 73: 673-679, 1992; and Mori, S. et al., Biochem. Biophys. Res. Commun. 183: 334-342, 1992). Specific examples of known strains are as follows: the HCV strain of genotype 1a (e.g., the H77 strain (GenBank Accession No. AF011751)); the HCV strains of genotype 1b (e.g., the J1 strain (GenBank Accession No. D89815), the Con1 strain (GenBank Accession No. AJ238799; it may be referred to as the Con-1 or con1 strain), and the TH strain (Wakita, T. et al., J. Biol. Chem., 269, 14205-14210, 1994, JP Patent Publication (kokai) No. 2004-179 A)); and the HCV strains of genotype 2a (e.g., the JFH-1 strain (GenBank Accession No. AB047639); it may be referred to as the JFH1 strain), the J6CF strain (GenBank Accession No. AF177036), the JCH-1 strain (GenBank Accession No. AB047640), the JCH-2 strain (GenBank Accession No. AB047641), the JCH-3 strain (GenBank Accession No. AB047642), the JCH-4 strain (GenBank Accession No. AB047643), the JCH-5 strain (GenBank Accession No. AB047644), and the JCH-6 strain (GenBank Accession No. AB047645)). In addition, the HC-J8 strain (GenBank Accession. No. D01221) is known as the HCV strain of genotype 2b, the NZL1 strain (GenBank Accession No. D17763) and the S52 strain (GenBank Accession No.) are known as the HCV strains of genotype 3a, the Tr-Kj strain (GenBank Accession No. D49374) is known as the HCV strain of genotype 3b, and the ED43 strain (GenBank Accession No.) is known as the HCV strain of genotype 4a, for example. The list of the GenBank Accession numbers of other strains has already been reported (Tokita, T. et al., J. Gen. Virol., 79: 1847-1857, 1998; Cristina, J. & Colina, R., Virol. J., 3: 1-8, 2006).

The genomic nucleotide sequences of the JFH-1 strain and HCV strains other than the JFH-1 strain of the present invention are available from the above documents or GenBank, HCV strains other than the JFH-1 strain of the aforementioned genotypes may be selected, and a strain of genotype 1a, 1b, or 2a is preferable.

The chimeric HCV gene can be prepared by performing PCR using the vector prepared via cloning of cDNA of HCV genome RNA as a template and synthesized DNA as a primer, amplifying necessary regions of the HCV genes, and ligating the resultants.

Further, cDNA of the chimeric HCV gene is ligated to an adequate restriction site located downstream of a promoter (e.g., the T7 promoter) of the pJFH1 plasmid (Wakita, T. et al., Nat. Med., 11:791-796, 2005, WO 2004/104198) to prepare a vector used for synthesizing HCV genome RNA. Upon introduction of RNA transcribed from such vector into a cell such as the Huh-7 cell, virus replication and packaging take place, and infectious HCV particles can then be produced.

(2) HCV Particle Preparation

RNA may be synthesized from HCV cDNA cloned under the control of a promoter, and the resulting RNA may be introduced into a cell to prepare a chimeric HCV particle.

Specifically, chimeric HCV particles can be prepared by a method comprising a step of culturing a cell that produces such HCV particles and a step of recovering such HCV particles. The cell that produces HCV particles can be obtained by infecting an HCV-sensitive cell (i.e., a cell capable of producing HCV particles) with the chimeric HCV particles of the present invention.

Examples of the promoter include, but are not limited to, T7 promoter, SP6 promoter, and T3 promoter, with T7 promoter being preferable.

A method for preparing the RNA in vitro using, as a template, a nucleic acid into which HCV cDNA has been cloned under the control of T7 promoter can be carried out with the use of, for example, the MEGAscript T7 kit (Ambion).

Cells into which RNA is introduced may be any cells that are capable of producing HCV particles, and examples include Huh-7, HepG2, IMY-N9, HeLa, 293 and 293T cells or cells derived from any thereof. Examples of preferable cells include Huh-7 cells or Huh7.5 cells derived therefrom and Huh7.5.1 cells. In addition, cells which express CD81 and/or Claudin 1 genes in Huh-7, HepG2, IMY-N9, HeLa, 293, or 293T cells may also be used (Lindenbach, B. D. et al., Science, 309: 623-626, 2005; Evans, M. J. et al., Nature, 446: 801-805, 2007; and Akazawa, D. et al., J. Virol., 81: 5036-5045, 2007).

Examples of methods for introducing RNA into cells include calcium phosphate coprecipitation, a DEAE-dextran method, lipofection, microinjection, and electroporation. Lipofection and electroporation are preferable, and electroporation is more preferable.

When cDNA is introduced into cells, HCV cDNA may be expressed in a system involving the use of an RNA polymerase I promoter and a terminator (WO 27037428 A1).

The capacity of the cells for virus particle production can be detected with the use of antibodies to proteins that constitute an HCV particle released in culture solution, such as a Core protein, an E1 protein and an E2 protein. Also, HCV genome RNA contained in the HCV virus particles in a culture medium may be amplified via RT-PCR using specific primers to detect the HCV genome RNA of interest, so that the presence of HCV virus particles can be indirectly detected.

Whether or not the prepared viruses are infectious can be evaluated by culturing cells into which HCV RNA has been introduced, bringing the resulting supernatant into contact with HCV permissive cells (e.g., Huh-7 cells or derivative strains thereof), and immunologically staining the cells with an anti-Core antibody, for example, after 48 hours to count the number of infected cells. Alternatively, the evaluation can be carried out by subjecting a cell extract to electrophoresis on SDS-polyacrylamide gel and detecting core proteins via Western blotting.

(3) Acquisition of Particle-Producing Cell Line

For efficient replication of the HCV genome, it is necessary that a mutation occur in the nucleotide sequence of the genome (Lohmann, V. et al., J. Virol. 75: 1437-1449, 2001). A mutation that enhances replication is referred to as an "adaptive mutation." The cells into which the HCV genome RNA has been introduced as prepared in (2) above may be subjected to subculture to obtain cell lines that continuously produce HCV particles. By continuing such culture, an adaptive mutation may occasionally take place in the HCV genome, and the production of HCV particles may be significantly enhanced.

A typical example of the use of such phenomenon is a technique in which genomic RNA of the chimeric HCV is introduced into a cell and a mutant exhibiting the improved ability to produce the virus is selected. An example of such mutation is permissive mutation of chimeric HCV particles of the H77 strain and the JFH-1 strain (MinKyung Y. et al., J. Virol., 81: 629-638, 2007). Permissive mutation randomly takes place depending on the virus strain, design of the chimeric HCV genome (the construct), and conditions of experimentation. Accordingly, such mutation is not necessarily applicable to genotype 1b. This necessitates the performance of an experiment for each construct of interest to obtain permissive mutants.

A mutation of a single amino acid residue significantly changes the replication capacity of HCV and the ability to produce the HCV particle. Mutations vary depending on the HCV genotype, the type of cell used for culture, and the experiment. Since nucleic acid mutation that is necessary for a mutation of a single amino acid residue cannot be detected via hybridization, the HCV gene sequence must be subjected to sequencing in order to detect such mutation.

Thus, an HCV genome sequence that is capable of producing a large quantity of HCV particles can be found by isolating HCV genome RNA from such cells and determining the nucleotide sequence.

In order to inspect whether or not such mutation is associated with the capacity for HCV replication or ability to produce the HCV particle, further, it is necessary to introduce a mutation into the original HCV genome and inspect whether or not the capacity for HCV replication or ability to produce the HCV particle is reproduced. In order to introduce a mutation into the original HCV genome, PCR may be carried out, or a commercially available mutagenesis kit (e.g., KOD-Plus-Mutagenesis Kit, Toyobo Co., Ltd.) may be used.

In addition, whether or not such mutation is specific for the HCV genome used or is effective for other HCV genomes can also be confirmed by reintroducing a mutation into an HCV genome that has not experienced mutation.

In the present invention, when the amino acid residue at the N terminus of the Core protein of the TH/JFH-1 strain (Example 1 below) was designated as amino acid residue 1, a mutation from proline residue, the 328th amino acid residue (amino acid 328) (or the 137th amino acid (amino acid 137) when the amino acid residue at the N terminus of the E1 protein was designated as amino acid residue 1) into alanine or threonine is found. The 328th amino acid residue from the amino acid residue at the N terminus of the Core protein is the same in the Con1 strain (GenBank Accession No. AJ238799) and the J1 strain (GenBank Accession No. D89815) of genotype 1b, the H77 strain of genotype 1a (GenBank Accession No. AF011751), the JFH-1 strain of genotype 2a (GenBank Accession No. AB047639), and the J6CF strain (GenBank Accession No. AF177036), in addition to the TH strain. It is suggested that a mutation of proline into another amino acid, and preferably a mutation thereof into alanine or threonine, would be effective for any HCV strain having proline as the 328th amino acid residue from the amino acid residue at the N terminus of the Core protein, in addition to the TH strain.

(4) Use of HCV Particles

HCV particles are preferable for applications as vaccines and antigens used for preparing anti-HCV antibodies.

Specifically, HCV particles can be used as vaccines without modification, but HCV particles can be attenuated or inactivated via a method known in the art. The virus can be inactivated by adding and mixing an inactivator such as formalin, β-propiolactone, or glutardialdehyde in, for example, a virus suspension and allowing the inactivator to react with the virus (Appaiahgari, M. B. & Vrati, S., Vaccine, 22: 3669-3675, 2004). Attenuated vaccines can be obtained by infecting cultured animal cells or animals (excluding humans) with chimeric HCV particles and repeating subculture to attenuate the pathogenicity. Alternatively, pathogenicity can be attenuated by negatively modifying a region associated with HCV proliferation or infection, for example, the Core-NS5B region, via genetic engineering.

Thus, the HCV vaccine of the present invention can be produced by a method comprising a step of inactivating or attenuating the chimeric HCV particles of the present invention to prepare the inactivated or attenuated chimeric HCV particles and a step of preparing the inactivated or attenuated chimeric HCV particles into the form of HCV vaccines.

The vaccine of the present invention can be formulated into a dosage form of, for example, a solution or suspension. The vaccine can be prepared in a solid state (e.g., a lyophilized preparation) that is suitable for dissolution or suspension it in a solution, so that the vaccine can be reconstituted immediately before use. Alternatively, such solid or preparation can be emulsified in the presence of a pharmaceutical surfactant or encapsulated in liposomes.

Active immunogenic ingredients, such as HCV particles, are often mixed with excipients that are pharmaceutically acceptable and compatible with the active ingredients. Examples of adequate excipients include water, physiological saline, dextrose, glycerol, ethanol, and mixtures thereof.

Further, the vaccine can contain a minor amount of an auxiliary agent (e.g., a humidifier or emulsifier), a pH buffer, and/or an adjuvant that enhances vaccine efficacy, where needed.

Examples of the effective adjuvant include, but are not limited to, aluminum hydroxide, N-acetyl-muramyl-L-threonyl-D-isoglutamine (thr-MDP), N-acetyl-nor-muramyl-L-alanyl-D-isoglutamine (referred to as CGP11637 or nor-MDP), N-acetylmuramyl-L-alanyl-D-isoglutaminyl-L-alanine-2-(1'-2'-dipalmitoyl-sn-glycero-3-hydr oxyphosphoryloxy)-ethylamine (referred to as CGP19835A or MTP-PE), and RIBI. RIBI contains three components extracted from bacteria; i.e. monophosphoryl lipid A, trehalose dimycolate, and a cell wall skeleton (HPL+TDM+CWS), in 2% squalene/Tween® 80 emulsion.

Efficacy of an adjuvant can be determined by assaying the amount of antibodies resulting from administration of a vaccine comprising HCV particles to a mammalian animal.

The vaccine of the present invention is generally administered parenterally, by injection such as subcutaneous injection or intramuscular injection, for example. Examples of other formulations that are suitable as other forms of dosage include suppositories and, optionally, oral preparations.

Optionally, one or more compounds having adjuvant activity can be added to the HCV vaccine. An adjuvant is a nonspecific stimulant to the immune system. Such substance enhances the immune response of a host against HCV vaccines. Specific examples of adjuvants that are known in the art include Freund's complete and incomplete adjuvants, vitamin E, a nonionic block copolymer, muramyl dipeptide, saponin, mineral oil, vegetable oil, and Carbopol. Examples of adjuvants that are particularly suitable for mucosal application include *E. coli* thermolabile toxin (LT) and Cholera toxin (CT). Examples of other adequate adjuvants include aluminum hydroxide, aluminum phosphate or aluminum oxide, an oil emulsion (e.g., Bayol® or Marcol 52®), saponin, and a vitamin E solubilizate. Accordingly, the vaccine of a preferable embodiment of the present invention comprises an adjuvant.

Concerning an injectable solution for subcutaneous, intracutaneous, intramuscular, or intravenous administration, other specific examples of a pharmaceutically acceptable carrier or diluent that is used for administration in combination with the HCV vaccine of the present invention in the injectable solution include a stabilizer, a carbohydrate (e.g., sorbitol, mannitol, starch, sucrose, glucose, or dextran), a protein (e.g., albumin or casein), a protein-containing substance (e.g., bovine serum or skimmed milk), and buffer (e.g., phosphate buffer).

Examples of conventional binders and carriers that are used for suppositories include polyalkylene glycol and triglyceride. Such suppositories can be prepared from a mixture comprising 0.5% to 50%, and preferably 1% to 20% active ingredients by weight. Oral preparations comprise excipients that are generally used. Examples of excipients include mannitol, lactose, starch, magnesium stearate, saccharin sodium, cellulose, and magnesium carbonate of pharmaceutical grade.

The vaccine of the present invention can be in the form of a solution, suspension, tablet, pill, capsule, sustained-release preparation, or powder, and its active ingredients (virus particles or part thereof) account for 10% to 95%, and preferably 25% to 70% thereof by weight.

The vaccine of the present invention is administered in a manner suitable for a dosage form and in an amount that can exert preventive and/or therapeutic effects. The amount to be administered is generally 0.01 μg to 100,000 μg antigen per dose. Such amount varies depending on the patient to be treated, the capacity of the patient for antibody synthesis in the immune system, and the desired degree of protection. Also, the amount varies depending on the route of administration, such as oral, subcutaneous, intracutaneous, intramuscular, or intravenous administration.

The vaccine of the present invention can be administered according to a single-administration schedule, and preferably according to a multiple-administration schedule. In the case of a multiple-administration schedule, 1 to 10 separate administrations are performed at the time of initiation of inoculation, and another administration can then be performed with a time interval that is necessary for maintaining and/or enhancing the immune response. For example, the second administration can be performed 1 to 4 months after the first. Where needed, administration may be subsequently performed several months after the first. The administration regimen is, at least partially, determined according to the needs of individual, and the regimen depends on the judgment made by a doctor.

Further, the vaccine comprising the HCV particles of the present invention may be administered with another immunosuppressant agent (e.g., immunoglobulin).

Further, the present invention provides a method in which the vaccine comprising the HCV particles of the present invention is administered to a healthy individual to induce an immune response to HCV in such healthy individual, and the vaccine is used for preventing new HCV infection. The present invention also provides a method in which the vaccine comprising the HCV particles of the present invention is administered to a patient infected with HCV to induce a potent immune response to HCV in vivo, and the vaccine is thus used as a therapeutic vaccine that eliminates HCV.

The HCV particles of the present invention are also useful as antigens used for preparing antibodies. The antibodies that recognize the HCV particles of the present invention used as antigens can be used for preventing or treating HCV infection as passive immunotherapeutic agents. Any antibodies can be used without limitation, and examples thereof include polyclonal antibodies, monoclonal antibodies, human antibodies, humanized antibodies, chimeric antibodies, fragments of any thereof (e.g., Fc, Fab and $(Fab')_2$), single-stranded antibodies (e.g., scFv), camel antibodies, and polyvalent antibodies (e.g., divalent and trivalent antibodies). Any antibodies can be used, and examples include IgG, IgE, IgM, IgD, IgA and IgY antibodies. Examples of the classes thereof include IgG1 to IgG4 and IgA1 to IgA2. Further, antibodies may involve chemical modification, such as glycosylation, PEG-modification, acetylation, phosphorylation, or amidation.

The anti-HCV antibodies can be prepared by a method comprising a step of administering the chimeric HCV particles, which are or are not inactivated or attenuated, of the present invention to animals (excluding humans), and preferably to mammalians or birds.

Examples of mammalians include mice, rats, rabbits, goats, sheep, horses, cattle, guinea pigs, dromedaries, Bactrian camels, and lamas. Dromedaries, Bactrian camels, and lamas are suitable for preparing an antibody consisting of the H chain. Examples of birds include chickens, geese and ostriches.

The blood serum may be taken from an animal to which the HCV particles of the present invention have been administered, in order to obtain antibodies of interest by well-known methods. Examples of such methods include ammonium sulfate fractionation, ion exchange chromatography, Protein A or Protein G-binding affinity chromatography, and gel filtration chromatography.

In addition, hybridomas that produce monoclonal antibody-producing cells can be prepared with the use of cells or tissue (e.g., B cells, spleen cells and lymph nodes) of the animals immunized with the HCV particles of the present invention and myeloma cells (e.g., myeloma cells derived from mice or rats). Methods for producing hybridomas are well-known in the art, and the method described in, for example, Antibodies: A Laboratory Manual (Cold Spring Harbor Laboratory, 1988) or *Tan Kuron Kotai Jikken Manual* (Manual of Monoclonal Antibody Experiments), Toyama and Ando (ed.), Kodansha Ltd., 1987) can be employed.

Monoclonal antibody-producing cells may be prepared via cell fusion or via other methods involving introduction of DNA of a cancer gene or infection with Epstein-Barr for immobilization of B lymphocytes.

Humanized antibodies and human antibodies can be prepared via phage display (e.g., Brinkman et al., J. Immunol. Methods, 182: 41-50, 1995; Ames et al., J. Immunol. Methods, 184: 177-186, 1995; WO 98/46645; WO 98/50433; and WO 98/24893) or with the use of human antibody-producing mice (e.g., KM mice (Kirin Pharma Co., Ltd.) or Xeno mice (Abgenix/Amgen)).

The monoclonal, polyclonal, human, or humanized antibodies obtained by such techniques are useful for diagnosis, therapy, and prevention of HCV.

The antibodies prepared with the use of the HCV particles of the present invention are administered with pharmaceutically acceptable solubilizers, additives, stabilizers, buffers, or the like. Such antibodies may be administered via any route. Subcutaneous, intracutaneous, or intramuscular administration is preferable, and intravenous administration is more preferable.

A preferable example of an antibody prepared with the use of the HCV particles of the present invention is an anti-hepatitis C virus antibody that recognizes the chimeric hepatitis C virus (HCV) particles of the present invention (i.e., the chimeric HCV particles comprising the nucleic acid of the present invention as the virus genome) as antigens. Such anti-hepatitis C virus antibodies can be prepared so as to react with the chimeric HCV particles of the present invention. Such anti-hepatitis C virus antibodies can bind to (react with) not only the chimeric HCV particles of the present invention, but they can also bind to (react with) a wide variety of other hepatitis C virus particles to inhibit the functions thereof, regardless of the process for producing the same.

In addition, the HCV particles of the present invention (i.e., the chimeric HCV particles) or cells that produce such particles can be used for screening for anti-HCV substances.

Specifically, this method for screening for an anti-hepatitis C virus substance comprises culturing, in the presence of a test substance:

(a) the cell that produces chimeric HCV particles; or (b) the chimeric HCV particle and hepatitis C virus-sensitive cell, and detecting replicon RNA or a virus particle derived from the above-mentioned nucleic acid contained in the chimeric HCV particles of the present invention in the culture product.

According to the above method, anti-HCV substances are selected as those capable of inhibiting virus infection or proliferation. In the present invention, the term "replicon RNA" mainly refers to RNA capable of autonomous replication, which is prepared via modification of the HCV virus genome. The term "capable of autonomous replication" used herein refers to the capacity for autonomously reproducing (i.e., replicating) a nucleic acid copy in a cell, as with plasmid DNA. An example of a known subgenome replicon RNA is recombinant RNA prepared via recombination of the translational region of the HCV structural protein with a drug-resistant gene and insertion of IRES of EMCV (encephalomyocarditis virus) into a site downstream of such recombined region. RNA replication is observed in cells into which such recombinant RNA has been introduced. The term "full-length genome replicon RNA" refers to RNA capable of autonomous replication of RNA derived from the full-length HCV genome when it has been introduced into cells. A typical example is recombinant RNA prepared by inserting a drug resistant gene (or a reporter gene) and IRES into a space between the 5'-untranslated region and the gene encoding the HCV core protein of RNA derived from the full-length HCV genome. The term "replicon RNA derived from a nucleic acid" used in the above method refers to replicon RNA transcribed from such nucleic acid. Examples of hepatitis C virus-sensitive cells include, but are not limited to, cells exemplified as cells into which HCV-derived RNA is to be introduced in the section "(2) HCV particle preparation" above (e.g., Huh-7, HepG2, IMY-N9, HeLa, 293 and 293T cells or derivative cells thereof).

EXAMPLES

Hereafter, the present invention is described in greater detail with reference to the examples, although the technical scope of the present invention is not limited thereto. In the examples below, the TH strain is exemplified as an HCV strain other than the JFH-1 strain, and strains other than the designated strain can also be prepared.

Example 1

Construction of TH/JFH-1 Plasmid

As cDNA of HCV genome RNA, cDNA of the TH/JFH-1 chimera comprising 5' UTR that is from the JFH-1 strain of genotype 2a (GenBank Accession No. AB047639, Kato, T. et al., Gastroenterology, 125: 1808-1817, 2003), a region from the Core protein to the N terminal 33 amino acids of the NS2 protein that is from the TH strain of genotype 1b (Wakita, T. et al., J. Biol. Chem., 269: 14205-14210, 1994; Moradpour, D. et al., Biochem. Biophys. Res. Commun., 246: 920-924, 1998; and WO 2006/022422), and a region from the N-terminal amino acid 34 of NS2 to 3' UTR that is from the JFH-1 strain of genotype 2a, was prepared.

SEQ ID NO: 5 shows the amino acid sequence of a protein encoded by TH/JFH-1. FIG. 1 shows a method for preparing such plasmid.

Specifically, cDNA corresponding to the entire genome RNA region derived from the JFH-1 strain was cloned into the pUC19 plasmid, and the resulting plasmid DNA, pJFH1 (Wakita, T. et al., Nat. Med., 11: 791-796, 2005; WO 2004/104198), and pTH comprising part of the virus genome TH strain isolated from a hepatitis C patient (WO 2006/022422) were used.

pJFH1 was used as a template, 10 μl of 5× buffer and 1 μl of the 10 mM dNTP mixture attached to the Phusion High-Fidelity DNA Polymerase kit (FINNZYMES), and 2.5 μl each of 10 μM primers -21M13 (SEQ ID NO: 8) and MS98 (SEQ ID NO: 9) were added, and deionized water was added to bring the total amount to 49.5 μl in the end. Thereafter, 0.5 μl of Phusion DNA Polymerase (FINNZYMES) was added thereto, and PCR was carried out. PCR was carried out by repeating a cycle of 98° C. for 10 seconds, 58° C. for 30 seconds, and 72° C. for 45 seconds 30 times. The resulting PCR product was designated as PCR product No. 1.

Subsequently, pTH was used as a template, 10 μl of 5× buffer and 1 μl of the 10 mM dNTP mixture attached to the Phusion High-Fidelity DNA Polymerase kit (FINNZYMES), and 2.5 μl each of 10 μM primers MS97 (SEQ ID NO: 10) and MS96 (SEQ ID NO: 11) were added, and deionized water was added to bring the total amount to 49.5 μl in the end. Thereafter, 0.5 μl of Phusion DNA Polymerase (FINNZYMES) was added thereto, and PCR was carried out. PCR was carried out by repeating a cycle of 98° C. for 10 seconds, 58° C. for 30 seconds, and 72° C. for 45 seconds 30 times. The resulting PCR product was designated as PCR product No. 2.

Subsequently, pJFH1 was used as a template, 10 μl of 5× buffer and 1 μl of the 10 mM dNTP mixture attached to the Phusion High-Fidelity DNA Polymerase kit (FINNZYMES), and 2.5 μl each of 10 μM primers MS99 (SEQ ID NO: 12) and MS89 (SEQ ID NO: 13) were added, and deionized water was added to bring the total amount to 49.5 μl in the end. Thereafter, 0.5 μl of Phusion DNA Polymerase (FINNZYMES) was added thereto, and PCR was carried out. PCR was carried out by repeating a cycle of 98° C. for 10 seconds, 58° C. for 30 seconds, and 72° C. for 45 seconds 30 times. The resulting PCR product was designated as PCR product No. 3.

PCR products were purified from agarose gel and eluted with the use of 50 μl of EB buffer attached to the QIAquick Gel Extraction kit (QIAGEN). DNAs of PCR product No. 1, PCR product No. 2, and PCR product No. 3 were mixed in amounts of 1 μl each, the resultant was used as a template, 10 μl of 5× buffer and 1 μl of the 10 mM dNTP mixture attached to the Phusion High-Fidelity DNA Polymerase kit (FINNZYMES), and 2.5 μl each of 10 μM primers -21M13 (SEQ ID NO: 8) and MS89 (SEQ ID NO: 13) were added, and deionized water was added to bring the total amount to 49.5 μl in the end. Thereafter, 0.5 μl of Phusion DNA Polymerase (FINNZYMES) was added thereto, and PCR was carried out. PCR was carried out by repeating a cycle of 98° C. for 10 seconds, 58° C. for 30 seconds, and 72° C. for 2 minutes 30 times. The resulting PCR product was designated as PCR product No. 4.

pJFH1 and the purified PCR product No. 4 were digested with the restriction enzymes, EcoRI and SpeI, and the DNA fragments were separated via agarose gel electrophoresis, followed by purification. These two DNA fragments were mixed with Ligation high (New England Biolabs), and the two DNA fragments were ligated to each other. The vector was designated as pTH/JFH1. This pTH/JFH1 vector is a nucleotide sequence encoding a chimeric gene having the 5'-untranslated region derived from the JFH-1 strain; a region encoding the Core, E1, E2, and p7 proteins and the N-terminal 33 amino acid residues of NS2 protein derived from the TH strain; a region encoding the NS2 protein starting at amino acid residue 34 at the N-terminus and the NS3, NS4A, NS4B, NS5A and NS5B proteins and the 3'-untranslated region of the JFH-1 strain.

Example 2

In Vitro RNA Synthesis and Introduction Thereof Into Cell pTH/JFH1 was cleaved with XbaI, and the resultant was then subjected to phenol/chloroform extraction and ethanol precipitation. Subsequently, the XbaI cleavage fragment was treated with Mung Bean Nuclease, and an 3' terminal extra nucleotide sequence derived from the XbaI recognition sequence was removed. Further, proteinase K treatment, phenol/chloroform extraction, and ethanol precipitation were carried out to purify the DNA fragments. The cleaved plasmids were used as templates, and the reaction was allowed to proceed at 37° C. for 3 hours using the MEGAscript T7 kit (Ambion) to synthesize HCV RNA. After the reaction, the synthesized RNA was treated with DNaseI and extracted with acidic phenol, followed by purification via ethanol precipitation.

The Huh7 cells ($3\times10^6$ cells) and 10 μg of HCV RNA were suspended in 400 μl of the Cytomix solution (120 mM KCl, 0.15 mM $CaCl_2$, 10 mM $K_2HPO_4/KH_2PO_4$, 25 mM Hepes, 2 mM EGTA, 5 mM $MgCl_2$, 20 mM ATP, and 50 mM Glutathione), the suspension was transferred to a 4-mm cuvette, and electroporation was carried out using the Gene Pulser (BioRad) at 260 V and 950 μF. Thereafter, the cells into which HCV RNA had been introduced were seeded on a 10 $cm^2$ dish and then subcultured.

Example 3

Figure 2:
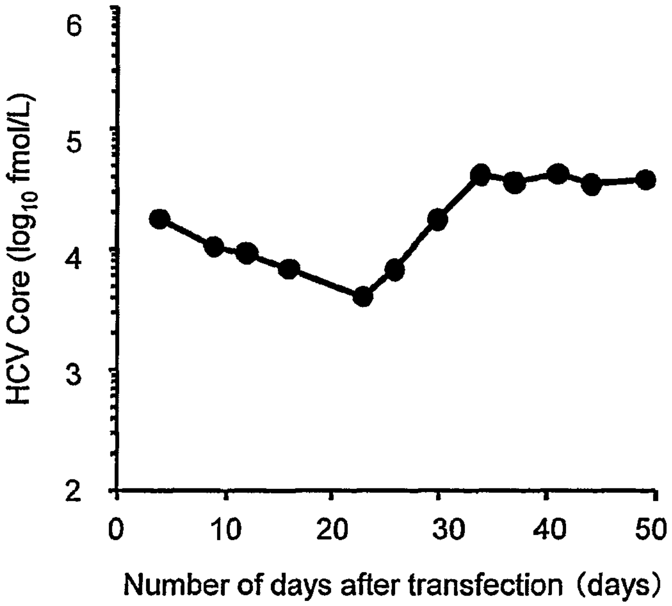
FIG. 2 shows changes in concentrations of the HCV Core protein in the culture supernatant assayed during each passage in repetitive subcultures conducted after introducing RNA synthesized from pTH/JFH1 into the Huh-7 cell. The amount of the Core protein in the culture supernatant continued to decrease until day 23, and it increased thereafter and maintained a constantly high level after day 34.

Production of HCV Particles with Cells into which Th/Jfh-1 RNA Had been Introduced At the time of subculture of cells into which TH/JFH-1 RNA had been introduced, the HCV Core protein contained in the culture supernatants was quantified using the HCV antigen ELISA test kit (Ortho) to confirm the production of HCV particles. As a result, the amount of HCV Core protein in the culture supernatant continued to decrease until 23 days after the introduction with the elapse of time, such amount began to increase 26 days after the introduction, and a constantly high amount of production was observed 34 days after the introduction (FIG. 2). Thus, it was considered that TH/JFH-1 RNA did not have the high capacity for virus production when it was introduced into Huh7 cell but it would acquire a high capacity for virus production upon introduction of an adaptive mutation necessary for virus production into the virus genome.

Example 4

Analysis of HCV Genome Sequence in Cell Infected with TH/JFH-1 Virus, which Had Undergone Subculture In order to inspect an adaptive mutation that is necessary for the THIJFH-1 virus to be produced in high amounts, total RNA was extracted from infected cells 34 days after RNA introduction, and the sequence of the HCV genome contained therein was analyzed.

Total RNA was extracted using Trizol (Invitrogen) and transcribed into cDNA. This cDNA was divided into 5 DNA fragments via PCR, ligated to the pGEM-T Easy vector (Promega), and transformed into *E. coli* DH5a to obtain colonies. Plasmids were extracted from 10 colonies using the QIAprep Mini kit (QIAGEN), and the nucleotide sequences of the DNA fragments were confirmed.

As a result, proline CCU (P) in the E1 region of the TH strain was found to have been substituted with alanine ACU (A) or threonine GCU (T). Proline corresponds to amino acid 328 when methionine; i.e., the amino acid residue at the N terminus of the Core protein of the TH strain (Wakita, T. et al., J. Biol. Chem., 269, 1994, pp. 14205-14210; Moradpour et al., Biochem. Biophys. Res. Commun., 246, 1998, pp. 920-924; and WO 2006/022422) was designated as amino acid residue 1 or amino acid residue 137 when the amino acid residue at the N terminus of the E1 protein was designated as amino acid residue 1.

SEQ ID NO: 6 shows the amino acid sequence of TH/JFH-1 (PA) and SEQ ID NO: 7 shows the amino acid sequence of TH/JFH-1 (PT).

Example 5

Construction of TH/JFH-1 Mutant Plasmid

A plasmid having an adaptive mutation necessary for the TH/JFH-1 virus to be produced in high amounts described in Example 4 was constructed. FIG. 3 shows a method for preparing a plasmid.

Specifically, pTH/JFH1 was used as a template, 10 µl of 5× buffer and 1 µl of the 10 mM dNTP mixture attached to the Phusion High-Fidelity DNA Polymerase kit (FINNZYMES), and 2.5 µl each of 10 µM primers MS151 (SEQ ID NO: 14) and MS165 (SEQ ID NO: 15) were added, and deionized water was added to bring the total amount to 49.5 µl in the end. Thereafter, 0.5 µl of Phusion DNA Polymerase (FINNZYMES) was added thereto, and PCR was carried out. PCR was carried out by repeating a cycle of 98° C. for 10 seconds, 58° C. for 30 seconds, and 72° C. for 1 minute 30 times. The resulting PCR product was designated as PCR product No. 5.

Subsequently, pTH/JFH1 was used as a template, 10 µl of 5× buffer and 1 µl of the 10 mM dNTP mixture attached to the Phusion High-Fidelity DNA Polymerase kit (FINNZYMES), and 2.5 µl each of 10 µM primers MS164 (SEQ ID NO: 16) and MS156 (SEQ ID NO: 17) were added, and deionized water was added to bring the total amount to 49.5 µl in the end. Thereafter, 0.5 µl of Phusion DNA Polymerase (FINNZYMES) was added thereto, and PCR was carried out. PCR was carried out by repeating a cycle of 98° C. for 10 seconds, 58° C. for 30 seconds, and 72° C. for 1 minute 30 times. The resulting PCR product was designated as PCR product No. 6.

Figure 3A:
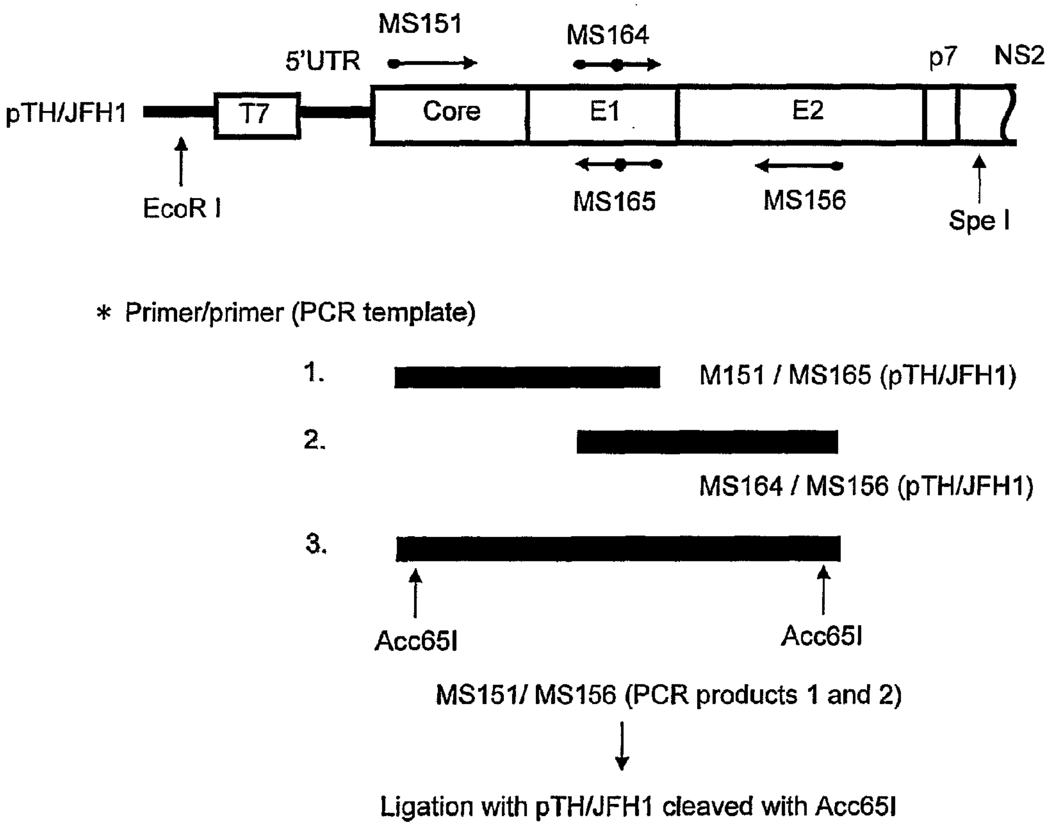
FIG. 3A shows a method for preparing the pTH/JFH1(PA) plasmid.

PCR products were purified from agarose gel and eluted with the use of 50 µl of EB buffer attached to the QIAquick Gel Extraction kit (QIAGEN). DNAs of PCR product No. 5 and PCR product No. 6 were mixed in amounts of 1 µl each, the resultant was used as a template, 10 µl of 5× buffer and 1 µl of the 10 mM dNTP mixture attached to the Phusion High-Fidelity DNA Polymerase kit (FINNZYMES), and 2.5 µl each of 10 µM primers MS151 (SEQ ID NO: 14) and MS156 (SEQ ID NO: 17) were added, and deionized water was added to bring the total amount to 49.5 µl in the end. Thereafter, 0.5 µl of Phusion DNA Polymerase (FINNZYMES) was added thereto, and PCR was carried out. PCR was carried out by repeating a cycle of 98° C. for 10 seconds, 58° C. for 30 seconds, and 72° C. for 1 minute and 30 seconds 30 times. The resulting PCR product was designated as PCR product No. 7 (FIG. 3A).

Subsequently, pTH/JFH 1 was used as a template, 10 µl of 5× buffer and 1 µl of the 10 mM dNTP mixture attached to the Phusion High-Fidelity DNA Polymerase kit (FINNZYMES), and 2.5 µl each of 10 µM primers MS151 (SEQ ID NO: 14) and MS163 (SEQ ID NO: 18) were added, and deionized water was added to bring the total amount to 49.5 µl in the end. Thereafter, 0.5 µl of Phusion DNA Polymerase (FINNZYMES) was added thereto, and PCR was carried out. PCR was carried out by repeating a cycle of 98° C. for 10 seconds, 58° C. for 30 seconds, and 72° C. for 1 minute 30 times. The resulting PCR product was designated as PCR product No. 8.

Subsequently, pTH/JFH1 was used as a template, 10 µl of 5× buffer and 1 µl of the 10 mM dNTP mixture attached to the Phusion High-Fidelity DNA Polymerase kit (FINNZYMES), and 2.5 µl each of 10 µM primers MS162 (SEQ ID NO: 19) and MS156 (SEQ ID NO: 17) were added, and deionized water was added to bring the total amount to 49.5 µl in the end. Thereafter, 0.5 µl of Phusion DNA Polymerase (FINNZYMES) was added thereto, and PCR was carried out. PCR was carried out by repeating a cycle of 98° C. for 10 seconds, 58° C. for 30 seconds, and 72° C. for 1 minute 30 times. The resulting PCR product was designated as PCR product No. 9.

Figure 3B:
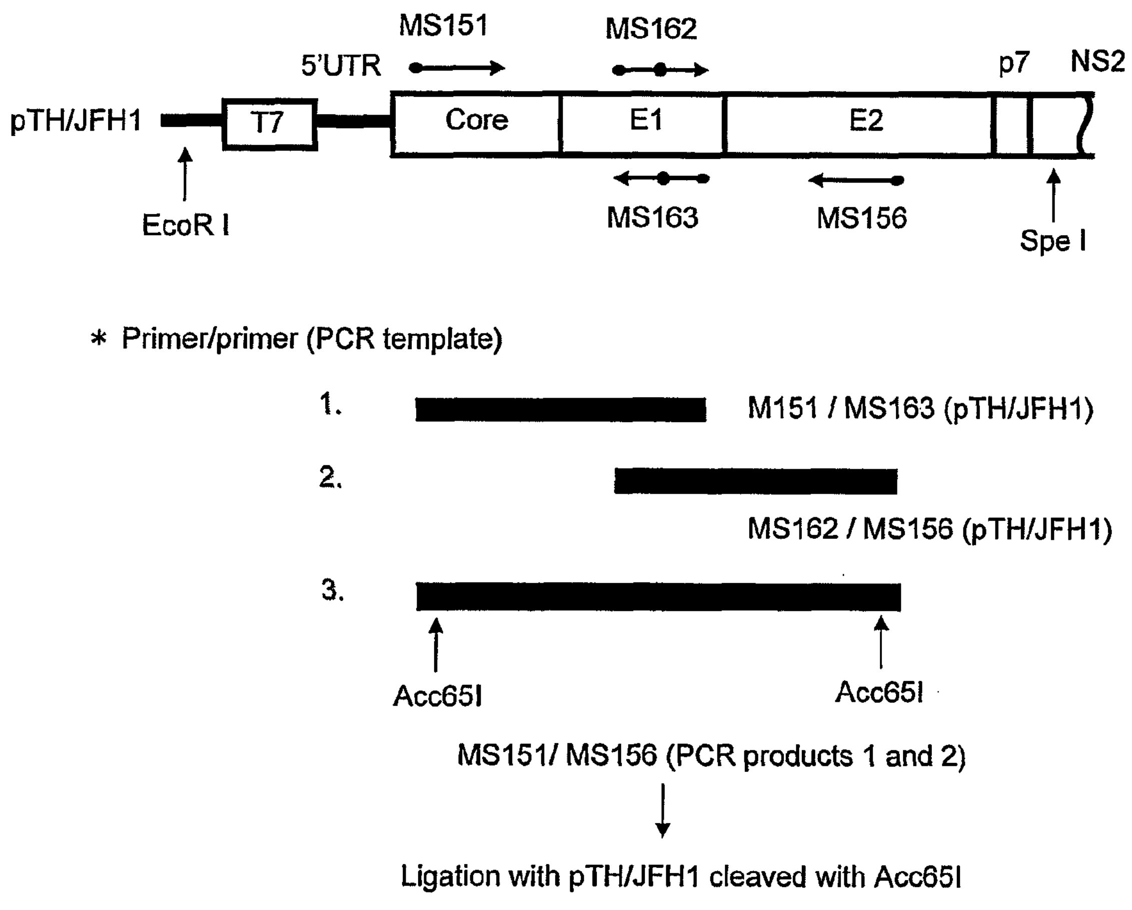
FIG. 3B shows a method for preparing the pTH/JFH1(PT) plasmid.

PCR products were purified from agarose gel and eluted with the use of 50 µl of EB buffer attached to the QIAquick Gel Extraction kit (QIAGEN). DNAs of PCR product No. 8 and PCR product No. 9 were mixed in amounts of 1 µl each, the resultant was used as a template, 10 µl of 5× buffer and 1 µl of the 10 mM dNTP mixture attached to the Phusion High-Fidelity DNA Polymerase kit (FINNZYMES), and 2.5 µl each of 10 µM primers MS151 (SEQ ID NO: 14) and MS156 (SEQ ID NO: 17) were added, and deionized water was added to bring the total amount to 49.5 µl in the end. Thereafter, 0.5 µl of Phusion DNA Polymerase (FINNZYMES) was added thereto, and PCR was carried out. PCR was carried out by repeating a cycle of 98° C. for 10 seconds, 58° C. for 30 seconds, and 72° C. for 1 minute and 30 seconds 30 times. The resulting PCR product was designated as PCR product No. 10 (FIG. 3B).

pTH/JFH1 and the purified PCR product No. 7 were digested with the Acc65I restriction enzyme and the DNA fragments were separated via agarose gel electrophoresis, followed by purification. These two DNA fragments were mixed with Ligation high (New England Biolabs), and the two DNA fragments were ligated to each other. The vector was designated as pTH/JFH-1(PA). This pTH/JFH1 (PA) vector comprises a nucleotide sequence encoding a chimeric gene having the 5'-untranslated region derived from the JFH-1 strain; a region encoding the Core, E1, E2 and p7 proteins and the N-terminal 33 amino acid residues of NS2 protein derived from the TH strain; a region encoding the NS2 protein starting at amino acid residue 34 at the N-terminus and the NS3, NS4A, NS4B, NS5A and NS5B proteins, and the 3'-untranslated region of the JFH-1 strain, wherein amino acid 328, when methionine as the amino acid at the N terminus of the Core protein is designated as amino acid 1, is alanine.

Subsequently, pTH/JFH1 and the purified PCR product No. 10 were digested with the Acc65I restriction enzyme and the DNA fragments were separated via agarose gel electrophoresis, followed by purification. These two DNA fragments were mixed with Ligation high (New England Biolabs), and the two DNA fragments were ligated to each other. The vector was designated as pTH/JFH1(PT). This pTH/JFH1 (PT) vector comprises a nucleotide sequence encoding a chimeric gene having the 5'-untranslated region derived from the JFH-1 strain; a region encoding the Core, E1, E2, and p7 proteins and the N-terminal 33 amino acid residues of NS2 protein derived from the TH strain; a region encoding the NS2 protein starting at amino acid residue 34 at the N-terminus and the NS3, NS4A, NS4B, NS5A and NS5B proteins, and the 3'-untranslated region of the JFH-1 strain, wherein amino acid 328, when methionine as the amino acid at the N terminus of the Core protein is designated as amino acid 1, is threonine.

The nucleotide sequences of pTH/JFH1 (PA) and pTH/JFH1 (PT) are shown in SEQ ID NOs: 1 and 2, respectively, in the sequence listings.

Example 6

Preparation of TH/JFH-1 (PA) and TH/JFH-1 (PT) Viruses

Plasmids prepared in Example 5 were cleaved with XbaI, and the resultants were then subjected to phenol/chloroform extraction and ethanol precipitation. Subsequently, the XbaI cleavage fragments were treated with Mung Bean Nuclease, and the 3'-terminal extra nucleotide sequences derived from the XbaI recognition sequence were removed. Further, proteinase K treatment, phenol/chloroform extraction, and ethanol precipitation were carried out to purify the DNA fragments. The cleaved plasmids were used as templates to synthesize HCV RNAs using the MEGAscript T7 kit (Ambion).

The Huh-7 cells ($3\times10^6$ cells) and 10 μg of HCV RNA were suspended in 400 μl of the Cytomix solution (120 mM KCl, 0.15 mM $CaCl_2$, 10 mM $K_2HPO_4/KH_2PO_4$, 25 mM Hepes, 2 mM EGTA, 5 mM $MgCl_2$, 20 mM ATP, and 50 mM Glutathione), the suspension was transferred to a 4-mm cuvette, and electroporation was carried out using the Gene Pulser (BioRad) at 260 V and 950 μF. Thereafter, the cells into which HCV RNA had been introduced were seeded on a 10 $cm^2$ dish and then subcultured.

Figure 4:
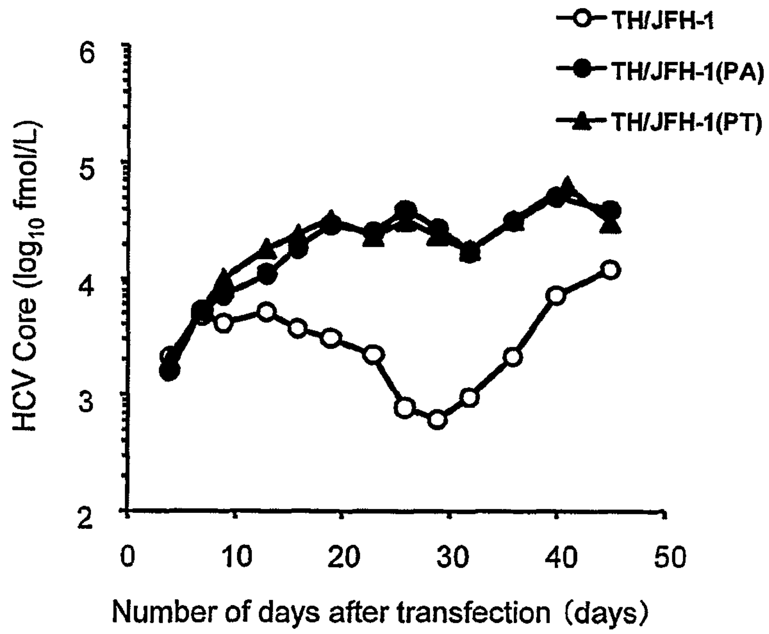
FIG. 4 shows changes in concentrations of the HCV Core protein in the culture supernatant assayed during each passage in repetitive subcultures conducted after introducing RNAs synthesized from pTH/JFH1, pTH/JFH1(PA) and pTH/JFH1(PT) into the Huh-7 cells. As with the case shown in FIG. 2, the Core protein amount of TH/JFH-1 continued to decrease until 29 days after introduction but it increased thereafter. In the case of the cells into which TH/JFH-1 (PA) and TH/JFH-1 (PT) had been introduced, however, a large quantity of Core protein was observed in the culture supernatant from the initial stage after the introduction, and the quantities of both core proteins were maintained at higher levels than that of TH/JFH-1.

At the time of subculture of cells into which TH/JFH-1 RNA, TH/JFH-1 (PA) RNA (SEQ ID NO: 3), and TH/JFH-1 (PT) RNA (SEQ ID NO: 4) prepared in Example 2 had been introduced, the HCV Core protein contained in the culture supernatants were quantified using the HCV antigen ELISA test kit (Ortho) to confirm the production of HCV particles. From the initial stage to the late stage of culture, the amount of HCV Core protein contained in the culture supernatant of cells into which RNA without mutation had been introduced was compared with that into which RNA with mutation had been introduced. As a result, the latter amount was found to be higher (FIG. 4).

Example 7

Evaluation of Infectivity of Virus into which Mutation Had been Introduced

The infectivity of viruses produced from cells into which TH/JFH-1(PA) RNA had been introduced was compared with that of wild-type TH/JFH-1. Changes in the amount of HCV Core protein in the cells and in the culture supernatants 4, 24, 48, 72 and 96 hours after RNA introduction were analyzed, and the infectivity of the culture supernatant was analyzed.

Specifically, TH/JFH-1 and TH/JFH-1(PA) RNA were synthesized in the same manner as in Example 6, $3\times10^6$ Huh-7 cells and 10 μg of HCV RNA were suspended in 400 μl of the Cytomix solution (120 mM KCl, 0.15 mM $CaCl_2$, 10 mM $K_2HPO_4/KH_2PO_4$, 25 mM Hepes, 2 mM EGTA, 5 mM $MgCl_2$, 20 mM ATP, and 50 mM glutathione), the suspension was transferred to a 4-mm cuvette, and electroporation was carried out using the Gene Pulser (BioRad) at 260 V and 950 μF. Thereafter, the cells into which HCV RNA had been introduced were seeded on a 10 $cm^2$ dish, the culture supernatant was collected 4, 24, 48, 72, and 96 hours later, the collected culture supernatant was filtered through a 0.45-μm filter (Millipore), and the HCV Core proteins were quantified using the HCV antigen ELISA test kit (Ortho). The 10 $cm^2$ dish from which the culture supernatant had been removed was washed with PBS, cells were scraped off using 500 μl of PBS and a scraper (Sumitomo Bakelite Co., Ltd.), and the cells were recovered via centrifugation. Passive Lysis Buffer (100 μl Promega) was added to the recovered cells to prepare a lysate, and the HCV Core proteins contained therein were quantified using the HCV antigen ELISA test kit (Ortho) as in the case of the culture supernatant.

The culture supernatant was serially diluted with a culture medium to quantify the infectious titer thereof in the following manner. The Huh-7 cells were seeded on a 96-well polylysine-coated plate (Corning) at $1\times10^4$ cells/well, culture was conducted for a whole day, the culture medium was exchanged with the culture supernatant which had been serially diluted with a culture medium, and culture was conducted for an additional 3 days. Thereafter, the culture medium was discarded, the cells were washed 3 times with PBS, and the cells were immobilized with methanol for 15 minutes. Subsequently, the wells were blocked with the use of Block Ace (Dainippon Sumitomo Pharma Co., Ltd.) containing 0.3% Triton-X 100 and allowed to react with the anti-HCV Core-specific antibodies (clone 2H9). Subsequently, the wells were washed with PBS and the cells were allowed to react with the Alexa488-labeled anti-mouse IgG antibodies (Invitrogen). Thereafter, the wells were washed with PBS, the number of infectious foci of each well was counted under a fluorescent microscope (Olympus Corporation), and the infectious titer of each culture supernatant was calculated in terms of the focus-forming unit (FFU).

As a result, the rate of the HCV Core protein secretion into the culture supernatant and the infectious titer of the culture supernatant were found to be higher in the cells into which TH/JFH-1(PA) RNA had been introduced than in cells into which wild-type TH/JFH-1 had been introduced (FIGS. 5 and 6). It was demonstrated that a mutation of proline 328 in TH/JFH-1 (SEQ ID NO: 5) would enhance HCV particle production.

INDUSTRIAL APPLICABILITY

HCV particles that are provided by the method of the present invention exhibit high levels of expression, ability to be produced, and infectivity. Thus, such HCV particles can be preferably used for preventive or therapeutic vaccines for HCV. In addition, the HCV particles of the present invention can be used as tools for inducing antibodies reacting with HCV.

All publications, patents, and patent applications cited herein are incorporated herein by reference in their entirety.

The invention claimed is:

1. A nucleic acid comprising a chimeric gene derived from hepatitis C viruses comprising regions each encoding, Core protein, E1 protein, E2 protein and p7 protein derived from a hepatitis C virus strain other than JFH-1 strain; NS2 protein derived from JFH-1 strain or a hepatitis C virus strain other than JFH-1 strain, or a chimeric NS2 protein of NS2 protein derived from JFH-1 strain and NS2 protein derived from a hepatitis C virus strain other than JFH-1 strain; and NS3 protein, NS4A protein, NS4B protein, NS5A protein and NS5B protein derived from JFH-1 strain in that order in 5' to 3' direction, wherein the residue at position 137 of the E1 protein from a hepatitis C virus strain other than JFH-1 strain is substituted with an amino acid residue other than proline; and wherein residue 137 in the E1 protein corresponds to residue 328 of SEQ ID NO: 5.

2. The nucleic acid according to claim 1, which comprises 5'-untranslated region of JFH-1 strain on the 5' side of the Core protein coding region and 3'-untranslated region of JFH-1 strain on the 3' side of the NS5B protein coding region.

3. The nucleic acid according to claim 1 or 2, wherein the hepatitis C virus strain other than JFH-1 strain is of genotype 1a, 1b, or 2a.

4. The nucleic acid according to claim 1, wherein the hepatitis C virus strain other than JFH-1 strain is selected from the group consisting of TH strain, Con1 strain, J1 strain and derivative strains thereof.

5. The nucleic acid according to claim 1, wherein the amino acid residue other than proline is selected from the group consisting of Ala, Leu, Ile, Val, Thr and Ser.

6. The nucleic acid according to claim 1, wherein the nucleic acid is DNA comprising the nucleotide sequence as shown in SEQ ID NO: 1 of the sequence listing or a nucleotide sequence having 90% or more identity to the nucleotide sequence as shown in SEQ ID NO: 1, or RNA comprising the nucleotide sequence as shown in SEQ ID NO: 3 of the sequence listing or a nucleotide sequence having 90% or more identity to the nucleotide sequence as shown in SEQ ID NO: 3.

7. The nucleic acid according to claim 1, wherein the nucleic acid is DNA comprising the nucleotide sequence as shown in SEQ ID NO: 2 of the sequence listing or a nucleotide sequence having 90% or more identity to the nucleotide sequence as shown in SEQ ID NO: 2, or RNA comprising the nucleotide sequence as shown in SEQ ID NO: 4 of the sequence listing or a nucleotide sequence having 90% or more identity to the nucleotide sequence as shown in SEQ ID NO: 4.

8. A vector comprising the nucleic acid according to claim 1.

9. A chimeric hepatitis C virus particle comprising the nucleic acid according to claim 1 as a virus genome.

10. A cell which produces the chimeric hepatitis C virus particle according to claim 9.

11. The cell according to claim 10, wherein the cell is of Huh-7 strain or a derivative strain thereof.

12. A method for screening for an anti-hepatitis C virus substance comprising, culturing, in the presence of a test substance:

(a) a cell which produces the chimeric hepatitis C virus particle according to claim 9; or (b) a hepatitis C virus-sensitive cell and the chimeric hepatitis C virus particle according to claim 9, and detecting replicon RNA or a virus particle derived from the nucleic acid of claim 9 in the resulting culture.

13. An immunogenic composition comprising the chimeric hepatitis C virus particle according to claim 9.

14. The immunogenic composition according to claim 13, wherein the chimeric hepatitis C virus particle is inactivated or attenuated.

15. A method for producing an anti-hepatitis C virus antibody, comprising administering to a non-human animal as an antigen a chimeric hepatitis C virus particle comprising:

a nucleic acid comprising a chimeric gene derived from hepatitis C virus comprising regions each encoding, Core protein, E1 protein, E2 protein and p7 protein derived from a hepatitis C virus strain other than JFH-1 strain; NS2 protein derived from JFH-1 strain or a hepatitis C virus strain other than JFH-1 strain, or a chimeric NS2 protein of NS2 protein derived from JFH-1 strain and NS2 protein derived from a hepatitis C virus strain other than JFH-1 strain; and NS3 protein, NS4A protein, NS4B protein, NS5A protein and NSSB protein derived from JFH-1 strain in that order in 5' to 3' direction, wherein the residue at position 137 of the E1 protein from a hepatitis C virus strain other than JFH-1 strain is substituted with an amino acid residue other than proline; and wherein residue 137 in the E1 protein corresponds to residue 328 of SEQ ID NO: 5.

* * * * *